(12) United States Patent
Spence et al.

(10) Patent No.: US 11,779,508 B2
(45) Date of Patent: Oct. 10, 2023

(54) THERAPEUTIC PRESSURE, THERMAL, AND/OR OTHER TREATMENT MODALITY SYSTEMS AND METHODS

(71) Applicant: Aquilo Sports LLC, Louisville, KY (US)

(72) Inventors: John-Paul Spence, Louisville, KY (US); Christian Buckley, Louisville, KY (US); Paul A. Spence, Aventura, FL (US)

(73) Assignee: Aquilo Sports LLC, Louisville, KY (US)

( * ) Notice: Subject to any disclaimer, the term of this patent is extended or adjusted under 35 U.S.C. 154(b) by 0 days.

(21) Appl. No.: 17/883,122

(22) Filed: Aug. 8, 2022

(65) Prior Publication Data

US 2023/0011693 A1   Jan. 12, 2023

Related U.S. Application Data

(63) Continuation of application No. PCT/US2022/034911, filed on Jun. 24, 2022.
(Continued)

(51) Int. Cl.
*A61H 9/00* (2006.01)
*A61F 7/00* (2006.01)

(52) U.S. Cl.
CPC ... *A61H 9/0078* (2013.01); *A61H 2201/0221* (2013.01); *A61H 2201/5002* (2013.01); *A61H 2201/5005* (2013.01); *A61H 2205/10* (2013.01)

(58) Field of Classification Search
CPC ...... A61H 9/00; A61H 9/0078; A61H 9/0092; A61F 7/00; A61F 2007/00; A61F 5/012; A61F 5/05816
See application file for complete search history.

(56) References Cited

U.S. PATENT DOCUMENTS 2,250,325 A   7/1941   Barnes
2,397,232 A   3/1946   Barnes et al.
(Continued)

FOREIGN PATENT DOCUMENTS

CN   101496643 A   8/2009
WO   WO-9504508 A1   2/1995
(Continued)

OTHER PUBLICATIONS

International Search Report and Written Opinion for International Application No. PCT/US2022/034911, dated Nov. 16, 2022, 19 pages.
(Continued)

*Primary Examiner* — Justine R Yu
*Assistant Examiner* — Christopher E Miller
(74) *Attorney, Agent, or Firm* — Cooley LLP

(57) ABSTRACT

Systems and methods described herein include a pressure delivery component that has a pressure applicator configured to selectively apply therapeutic pressure to a treatment portion of a user body, and also includes a thermal delivery component that has a thermal applicator that is a configured to apply thermal treatment to the treatment portion. The thermal applicator may be removably disposable in operative relationship with the pressure delivery component in a use configuration of the treatment delivery component such that the thermal applicator is disposable between the treatment portion and the pressure applicator when the treatment delivery component is disposed on the treatment portion in the use configuration. Moreover, the pressure applicator is operable to apply pressure to the thermal applicator to enhance apposition of the thermal applicator to the treatment portion.

23 Claims, 61 Drawing Sheets

Related U.S. Application Data

(60) Provisional application No. 63/215,129, filed on Jun. 25, 2021.

(56) References Cited

U.S. PATENT DOCUMENTS

| | | | |
|---|---|---|---|
| 2,726,658 A | 12/1955 | Chessey | |
| 2,823,668 A * | 2/1958 | Van Court | A61F 5/05816 |
| | | | 128/DIG. 20 |
| 3,074,410 A | 1/1963 | Foster | |
| 3,091,242 A | 5/1963 | Johnson, Jr. et al. | |
| 3,610,323 A | 10/1971 | Troyer et al. | |
| 3,738,367 A | 6/1973 | Hardy et al. | |
| 3,744,053 A | 7/1973 | Parker et al. | |
| 3,867,939 A | 2/1975 | Moore et al. | |
| 3,995,621 A | 12/1976 | Fletcher et al. | |
| 4,095,593 A | 6/1978 | Webbon et al. | |
| 4,108,146 A | 8/1978 | Golden | |
| 4,114,620 A | 9/1978 | Moore et al. | |
| 4,118,946 A | 10/1978 | Tubin | |
| 4,149,529 A | 4/1979 | Copeland et al. | |
| 4,149,541 A | 4/1979 | Gammons et al. | |
| 4,154,245 A | 5/1979 | Daily | |
| 4,190,054 A * | 2/1980 | Brennan | F25D 3/08 |
| | | | 607/109 |
| 4,470,263 A | 9/1984 | Lehovec et al. | |
| 4,517,972 A | 5/1985 | Finch, Jr. | |
| 4,523,594 A | 6/1985 | Kuznetz | |
| 4,586,506 A * | 5/1986 | Nangle | A61F 13/06 |
| | | | 607/112 |
| 4,691,762 A | 9/1987 | Elkins et al. | |
| 4,741,338 A | 5/1988 | Miyamae | |
| 4,919,134 A | 4/1990 | Streeter | |
| 4,962,761 A | 10/1990 | Golden | |
| 4,972,832 A * | 11/1990 | Trapini | A61F 7/02 |
| | | | 607/108 |
| 5,062,414 A | 11/1991 | Grim | |
| 5,097,829 A | 3/1992 | Quisenberry | |
| 5,133,348 A | 7/1992 | Mayn | |
| 5,172,689 A * | 12/1992 | Wright | A61F 7/10 |
| | | | 607/104 |
| 5,190,032 A | 3/1993 | Zacoi | |
| 5,230,335 A | 7/1993 | Johnson, Jr. et al. | |
| 5,271,239 A | 12/1993 | Rockenfeller et al. | |
| 5,304,213 A | 4/1994 | Berke et al. | |
| 5,320,164 A | 6/1994 | Szczesuil et al. | |
| 5,383,919 A | 1/1995 | Kelly et al. | |
| 5,407,421 A * | 4/1995 | Goldsmith | A61F 7/02 |
| | | | 602/5 |
| 5,411,541 A | 5/1995 | Bell et al. | |
| 5,411,542 A | 5/1995 | Jensen | |
| 5,466,250 A | 11/1995 | Johnson, Jr. et al. | |
| 5,470,353 A | 11/1995 | Jensen | |
| 5,486,207 A | 1/1996 | Mahawili | |
| 5,514,169 A | 5/1996 | Dickerhoff et al. | |
| 5,534,021 A * | 7/1996 | Dvoretzky | A61F 7/02 |
| | | | 607/114 |
| 5,545,194 A | 8/1996 | Augustine | |
| 5,609,620 A | 3/1997 | Daily | |
| 5,658,325 A | 8/1997 | Augustine | |
| 5,662,695 A | 9/1997 | Mason et al. | |
| 5,733,318 A | 3/1998 | Augustine | |
| 5,755,275 A | 5/1998 | Rose et al. | |
| 5,800,490 A | 9/1998 | Patz et al. | |
| 5,806,335 A | 9/1998 | Herbert et al. | |
| 5,887,437 A | 3/1999 | Maxim | |
| 5,895,418 A | 4/1999 | Saringer | |
| 5,913,849 A | 6/1999 | Sundstroem et al. | |
| 5,980,561 A | 11/1999 | Kolen et al. | |
| 6,109,338 A | 8/2000 | Butzer | |
| 6,117,164 A | 9/2000 | Gildersleeve et al. | |
| 6,197,045 B1 | 3/2001 | Carson | |
| 6,238,427 B1 | 5/2001 | Matta | |
| 6,349,558 B1 | 2/2002 | Ichikawa et al. | |
| 6,416,534 B1 * | 7/2002 | Montagnino | A61F 7/007 |
| | | | 602/14 |
| 6,438,964 B1 | 8/2002 | Giblin | |
| 6,554,785 B1 * | 4/2003 | Sroufe | A61F 5/0111 |
| | | | 128/882 |
| 6,620,187 B2 | 9/2003 | Carson et al. | |
| 6,648,905 B2 | 11/2003 | Hoglund et al. | |
| 6,695,872 B2 | 2/2004 | Elkins | |
| 6,871,878 B2 | 3/2005 | Miros | |
| 6,945,988 B1 * | 9/2005 | Jones | A61F 7/10 |
| | | | 607/108 |
| 7,000,682 B2 | 2/2006 | Chambers | |
| 7,089,995 B2 | 8/2006 | Koscheyev et al. | |
| 7,107,629 B2 | 9/2006 | Miros et al. | |
| 7,198,093 B1 | 4/2007 | Elkins | |
| 7,394,655 B1 | 7/2008 | O'Keeffe | |
| 7,837,638 B2 | 11/2010 | Miros et al. | |
| 7,896,910 B2 | 3/2011 | Schirrmacher et al. | |
| 8,032,951 B1 * | 10/2011 | Nestberg | A41D 27/20 |
| | | | 2/69 |
| 8,043,242 B2 | 10/2011 | McSpadden et al. | |
| 8,485,995 B1 | 7/2013 | Maxon-Maldonado | |
| 8,715,330 B2 | 5/2014 | Lowe et al. | |
| 8,753,383 B2 | 6/2014 | Parish et al. | |
| 9,943,437 B2 | 4/2018 | Lowe et al. | |
| 2002/0019657 A1 | 2/2002 | Elkins | |
| 2002/0032473 A1 | 3/2002 | Kushnir et al. | |
| 2003/0163180 A1 | 8/2003 | Hoglund et al. | |
| 2004/0068309 A1 | 4/2004 | Edelman | |
| 2005/0096714 A1 | 5/2005 | Freedman et al. | |
| 2005/0143797 A1 | 6/2005 | Parish et al. | |
| 2005/0159690 A1 | 7/2005 | Barak et al. | |
| 2005/0256556 A1 | 11/2005 | Schirrmacher et al. | |
| 2007/0161932 A1 * | 7/2007 | Pick | A61F 7/08 |
| | | | 602/5 |
| 2007/0162096 A1 | 7/2007 | Zakuto et al. | |
| 2008/0077202 A1 | 3/2008 | Levinson | |
| 2008/0195012 A1 | 8/2008 | Miros et al. | |
| 2008/0195185 A1 | 8/2008 | Krempel et al. | |
| 2009/0020521 A1 * | 1/2009 | Blaszczykiewicz | H05B 3/342 |
| | | | 219/529 |
| 2009/0228082 A1 | 9/2009 | Ross, III et al. | |
| 2009/0240216 A1 | 9/2009 | Hannigan et al. | |
| 2010/0210982 A1 * | 8/2010 | Balachandran | A61H 9/0078 |
| | | | 601/152 |
| 2010/0211122 A1 * | 8/2010 | Hensley | A61F 7/02 |
| | | | 607/3 |
| 2010/0268130 A1 | 10/2010 | Khan | |
| 2011/0004133 A1 * | 1/2011 | Viner | A61F 7/10 |
| | | | 602/14 |
| 2011/0098793 A1 | 4/2011 | Lowe et al. | |
| 2011/0306910 A1 * | 12/2011 | Siegner | A61F 13/046 |
| | | | 602/13 |
| 2012/0238924 A1 | 9/2012 | Avni | |
| 2012/0323152 A1 * | 12/2012 | Schubert | A61H 9/0092 |
| | | | 601/149 |
| 2013/0013033 A1 | 1/2013 | Lowe | |
| 2013/0253383 A1 * | 9/2013 | Maxon-Maldonado | A61H 1/00 |
| | | | 601/15 |
| 2014/0012169 A1 * | 1/2014 | Wilford | A61H 1/008 |
| | | | 601/151 |
| 2014/0142473 A1 | 5/2014 | Lowe et al. | |
| 2014/0222121 A1 | 8/2014 | Spence et al. | |
| 2014/0276254 A1 * | 9/2014 | Varga | A61H 9/0007 |
| | | | 601/15 |
| 2014/0316314 A1 * | 10/2014 | Schubert | A61H 9/0092 |
| | | | 601/149 |
| 2014/0336544 A1 * | 11/2014 | Ransom | A61F 7/02 |
| | | | 601/18 |
| 2016/0361196 A1 | 12/2016 | Spence et al. | |
| 2019/0183673 A1 * | 6/2019 | Chiu | A61F 7/0085 |
| 2022/0047447 A1 * | 2/2022 | Wang | A61F 7/007 |
| 2022/0071790 A1 * | 3/2022 | LoGuercio | A61F 7/02 |
| 2022/0287864 A1 * | 9/2022 | Goumas | A61F 7/02 |
| 2022/0354690 A1 * | 11/2022 | McGregor | A61F 7/0085 |

(56) References Cited

U.S. PATENT DOCUMENTS

FOREIGN PATENT DOCUMENTS

| WO | WO-9807397 A1 | 2/1998 |
| WO | WO-9944552 A1 | 9/1999 |
| WO | WO-03000079 A2 | 1/2003 |
| WO | WO-2013013059 A1 | 1/2013 |
| WO | WO-2014184324 A1 | 11/2014 |

OTHER PUBLICATIONS

Extended European Search Report for European Application No. 12815076, dated Feb. 24, 2015, 9 pages.
International Preliminary Report on Patentability for International Application No. PCT/US2012/047428, dated Jan. 21, 2014, 6 pages.
International Search Report and Written Opinion for International Application No. PCT/US2012/047428, dated Dec. 4, 2012, 9 pages.
Invitation to Pay Additional Fees for International Application No. PCT/US2022/034911, dated Sep. 13, 2022, 4 pages.
Office Action for Chinese Application No. 201280035938.6, dated Jul. 28, 2015, 20 pages.
Office Action for Chinese Application No. 201280035938.6, dated Jul. 28, 2016, 23 pages.
Office Action for Chinese Application No. 201280035938.6, dated Jun. 26, 2017, 33 pages.
Office Action for Chinese Application No. 201280035938.6, dated Sep. 22, 2014, 15 pages.

* cited by examiner

12020

THERAPEUTIC PRESSURE, THERMAL, AND/OR OTHER TREATMENT MODALITY SYSTEMS AND METHODS

CROSS REFERENCE TO RELATED APPLICATIONS

This application is a continuation of International Patent Application No. PCT/US2022/034911, filed Jun. 24, 2022, entitled "Therapeutic Pressure, Thermal, and/or Other Treatment Modality Systems and Methods," which claims priority to and the benefit of U.S. Provisional Application Ser. No. 63/215,129, filed Jun. 25, 2021, entitled "Therapeutic Heating and Cooling Systems and Methods," the entire disclosure of which is incorporated herein by reference.

This application is also related to International Patent Application Publication No. WO 2013/013059, filed Jul. 19, 2012, entitled "Athletic Cooling and Heating Systems, Devices, and Methods," (the '059 application) the entire disclosure of which is incorporated herein by reference.

BACKGROUND

Embodiments described herein relate to systems in which pressure treatment, thermal treatment (cooling and/or heating), and/or other treatment (non-pressure, and non-thermal) may be applied to a treatment portion of a user's body, concurrently and/or sequentially, for therapeutic purposes including recovery from athletic activity (including muscle soreness after exercise), muscle ischemia, muscle trauma, phantom limb pain, muscle cramps, night leg cramps and spasms, and/or promotion of tissue healing.

Cooling and pressure therapy are particularly desirable treatment regiments utilized by athletes and users to reduce inflammation and swelling that athletes may experience in different parts of their bodies after athletic activity, or muscular pain or muscular discomfort users may be experiencing. Athletes or other users may also seek non-pressure and non-thermal treatments such as electrostimulation, targeted drug delivery, vibrational massage, etc. Systems and devices that can be mounted on different parts of a user's body to provide such therapies are desirable. However, there can be significant difference in size between different parts of a user's body, for example, a torso of user can have a significantly larger cross-section than a leg of user, which in turn may have a larger cross-section than an arm of a user. This makes it difficult for single therapy delivery system or device to be used on a different portions of a user's body. Similarly, athletes and users can vary significantly in their size and weight. For example, linebackers in football teams are generally heavier than wide receivers or kickers. Moreover, female athletes tend to be much smaller than their male counterparts even in the same sports. Conventional systems and devices for delivering therapy are generally sized for use by a user having a particular size or weight, or on a particular portion of the body of the user. Thus, different user's such as various athletes within a team would have to purchase and maintain multiple such conventional systems or devices to be able to provide therapeutic treatment to each of its members. Moreover, conventional systems generally integrate pressure and thermal treatment components in treatment devices, decreasing flexibility in usage of such systems.

Accordingly, a need exists for systems and devices for delivering treatments and therapies that have adjustable sizes for fitting users of different sizes, and that are capable of delivering various treatments such as pressure treatment, thermal treatment, and/or other treatments in any suitable combination and configuration.

SUMMARY

Disclosed systems include an apparatus including a treatment delivery component that includes a pressure delivery component having a pressure applicator configured to selectively apply therapeutic pressure to a treatment portion of a user body with pressurized fluid received through a pressure conduit coupled to the pressure applicator. The apparatus also includes a thermal delivery component having a thermal applicator configured to selectively apply thermal treatment to the treatment portion with thermal energy received from or withdrawn by a thermal conduit coupled to the thermal applicator. The thermal delivery component is removably disposable in operative relationship with the pressure delivery component in a use configuration of the treatment delivery component such that the thermal applicator is disposable between the treatment portion and the pressure applicator when the treatment delivery component is disposed on the treatment portion in the use configuration. Moreover, the pressure applicator is operable to apply pressure to the thermal applicator to enhance apposition of the thermal applicator to the treatment portion.

Embodiments described herein also relate to a method including configuring a treatment delivery component for delivery of a pressure treatment modality by a pressure delivery component having a pressure applicator and a thermal treatment modality by a thermal delivery component having a thermal applicator to a treatment portion of a user's body. The treatment delivery component includes an outer shell coupled to the pressure applicator, and the configuring includes releasably coupling the thermal applicator to one or more of the outer shell and the pressure applicator. The method also includes disposing the treatment delivery component in operative relationship with the treatment portion with the thermal applicator adjacent to a surface of the treatment portion. The treatment delivery component is coupled to a control unit, the control unit having a pressure source and a thermal source. The coupling includes coupling to the pressure source a pressure conduit coupled to the pressure applicator and coupling to the thermal source a thermal conduit coupled to the thermal applicator. The pressure treatment modality is delivered to the treatment portion by the pressure delivery component. The method also includes delivering the thermal treatment modality to the treatment portion by the thermal delivery component.

DETAILED DESCRIPTION

Figure 1:
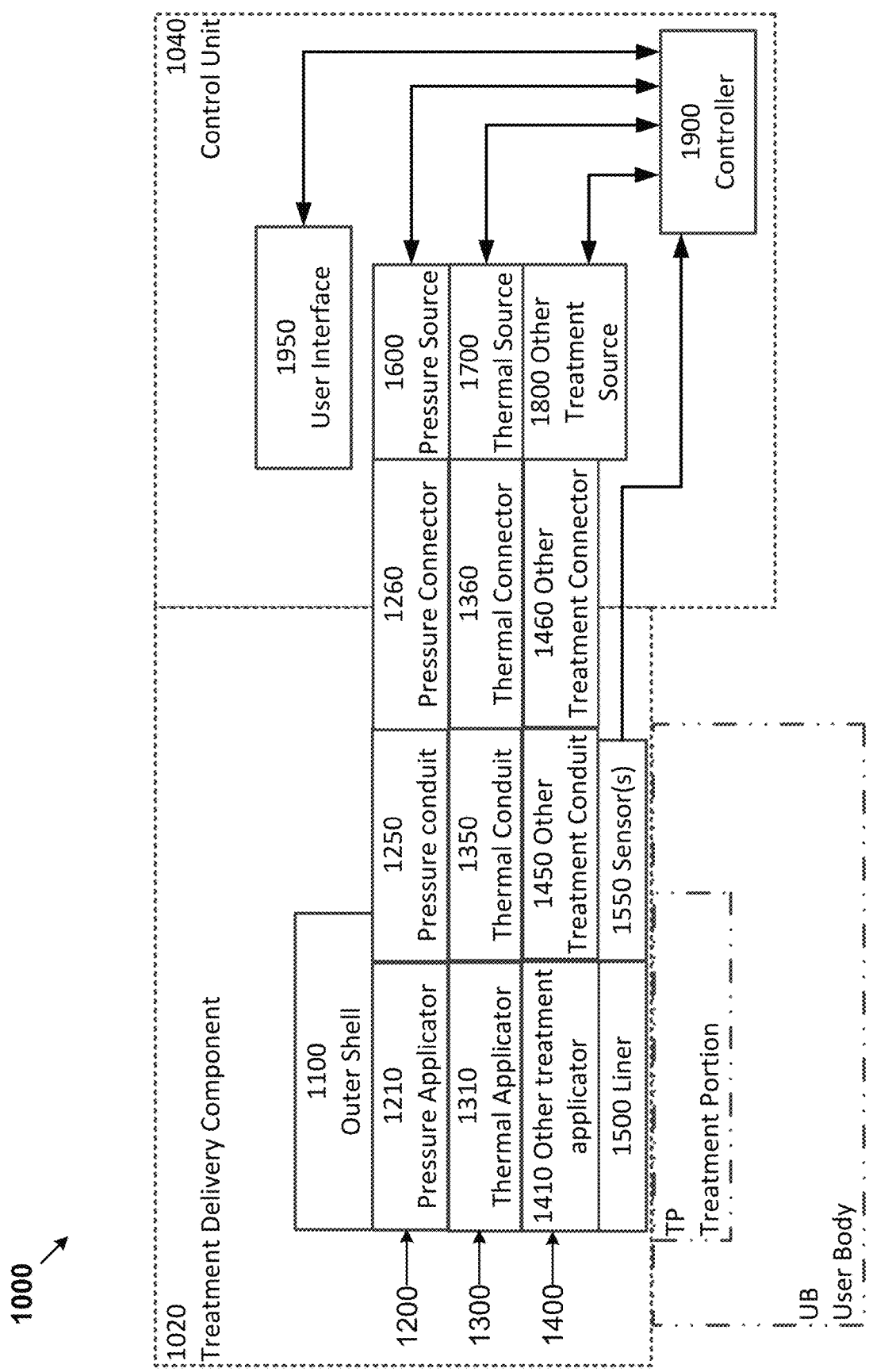
FIG. 1 is a schematic illustration of a treatment system, according to an embodiment.

Embodiments and implementations described herein relate to systems in which pressure treatment, thermal treatment (cooling and/or heating), and/or other treatment (non-pressure, and non-thermal) may be applied to a treatment portion of a user's body, concurrently and/or sequentially, for therapeutic purposes including recovery from athletic activity (including muscle soreness after exercise), muscle ischemia, muscle trauma, phantom limb pain, muscle cramps, night leg cramps and spasms, and/or promotion of tissue healing.

In some embodiments, a treatment system includes a treatment delivery component that includes a pressure delivery component that has a pressure applicator configured to selectively apply therapeutic pressure to a treatment portion of a user body with pressurized fluid received through a pressure conduit coupled to the pressure applicator. The apparatus may also include a thermal delivery component that has a thermal applicator that is a configured to apply thermal treatment to the treatment portion with thermal energy received from or withdrawn by a thermal conduit coupled to the thermal applicator. The thermal applicator may be removably disposable in operative relationship with the pressure delivery component in a use configuration of the treatment delivery component such that the thermal applicator is disposable between the treatment portion and the pressure applicator when the treatment delivery component is disposed on the treatment portion in the use configuration. Moreover, the pressure applicator is operable to apply pressure to the thermal applicator to enhance apposition of the thermal applicator to the treatment portion.

The apparatus may include a liner coupled to the pressure applicator or a portion of the apparatus, that provides a receptacle or cavity in which the thermal applicator may be removably disposable, and can also be removed and washed so as to maintain hygiene and enable hygienic use of the system by multiple users. The apparatus may also be configured to include various components, for example, clips, magnets, bolsters, etc., that allow portions of the pressure applicator and/or the thermal applicator to not be in apposition with the treatment portion so as to conform or fit to various portions of a user's body, or to treatment portions having various sizes. The system may also include a control unit to allow selective delivery of the pressurized fluid to the pressure applicator and/or thermal energy to the thermal applicator independently, simultaneously, sequentially, or in any suitable order. Moreover, the applicator may also include other therapeutic delivery mechanisms, for example, electrostimulation electrodes, electroporation mechanisms, chemical or medicament delivery mechanisms, electromagnetic stimulation mechanisms, vibration actuators, or any other non-pressure or non-thermal delivery mechanisms. The system may also include sensors to sense various parameters indicative of the health of the user, and/or the status or efficacy of any of the treatment modalities being applied to the user by the treatment system.

The terminology used herein is for the purpose of describing particular embodiments only and is not intended to limit the full scope of the claims. Unless defined otherwise, all technical and scientific terms used herein have the same meanings as commonly understood by one of ordinary skill in the art.

As used in this specification, the singular forms "a," "an," and "the" include plural referents unless the context clearly dictates otherwise. For example, the term "a member" is intended to mean a single member or a combination of members, "a material" is intended to mean one or more materials, or a combination thereof. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims, are generally intended as "open" terms (e.g., the term "including" should be interpreted as "including but not limited to," the term "having" should be interpreted as "having at least," etc.). For example, the terms "comprise(s)" and/or "comprising," when used in this specification, are intended to mean "including, but not limited to." While such open terms indicate the presence of stated features, integers (or fractions thereof), steps, operations, elements, and/or components, they do not preclude the presence or addition of one or more other features, integers (or fractions thereof), steps, operations, elements, components, and/or groups thereof, unless expressly stated otherwise.

As used herein the term "and/or" includes any and all combinations of one or more of the associated listed items. Said another way, the phrase "and/or" should be understood to mean "either or both" of the elements so conjoined (i.e., elements that are conjunctively present in some cases and disjunctively present in other cases). It should be understood that any suitable disjunctive word and/or phrase presenting two or more alternative terms, whether in the description, claims, or drawings, contemplate the possibilities of including one of the terms, either of the terms, or both terms. Other elements may optionally be present other than the elements specifically identified by the "and/or" clause, whether related or unrelated to those elements specifically identified. Thus, as a non-limiting example, a reference to "A and/or B" can refer to "A" only (optionally including elements other than "B"), to "B" only (optionally including elements other than "A"), to both "A" and "B" (optionally including other elements), etc.

As used herein, "or" should be understood to have the same meaning as "and/or" as defined above. For example, when separating items in a list, "or" or "and/or" shall be interpreted as being inclusive (e.g., the inclusion of at least one, but also including more than one, of a number or list of elements, and, optionally, additional unlisted items). Only terms clearly indicated to the contrary, such as when modified by "only one of" or "exactly one of" (e.g., only one of "A" or "B," "A" or "B" but not both, and/or the like) will refer to the inclusion of exactly one element of a number or list of elements.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements, unless expressly stated otherwise. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B" or "at least one of A and/or B") can refer to one or more "A" without "B," one or more "B" without "A," one or more "A" and one or more "B," etc.

All ranges disclosed herein are intended to encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member and/or a fraction of an individual member where appropriate.

As used herein, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include 0.45 and 0.55, a value of about 10 can include 9 to 11, and a value of about 100 can include 90 to 110. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

As used herein, the term "set" can refer to multiple features, components, members, etc. or a singular feature, component, member, etc. with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive (glue, etc.), mechanical fastening such as stitching, stapling, etc., or any suitable method).

Referring now to the drawings, FIG. 1 is a schematic illustration of a treatment system 1000 according to an embodiment. As shown in FIG. 1, treatment system 1000 includes two primary subsystems—a treatment delivery component 1020 and a control unit 1040.

Treatment delivery component 1020 is configured to be releasably secured to a user body UB of a user to whom treatment is to be delivered by treatment system 1000. Treatment delivery component 1020 includes an outer shell 1100 that can enclose, cover, and/or support one or more of the other components or subsystems of treatment delivery component 1020, and maintain them in operative position with respect to a treatment portion TP of a user body UB to which treatment is to be delivered. Those components or subsystems can include one or more of a pressure delivery component 1200, thermal delivery component 1300, and/or other treatment delivery component 1400, each of which is described in more detail below. Treatment delivery component 1020 can also include a liner 1500 and one or more sensors 1550.

Control unit 1040 can include a controller 1900, a user interface 1950, and one or more of a pressure source 1600 (coupleable to pressure delivery component 1200), thermal source 1700 (coupleable to thermal delivery component 1300), and/or other treatment source 1800 (coupleable to other treatment delivery component 1400).

Figure 2A:
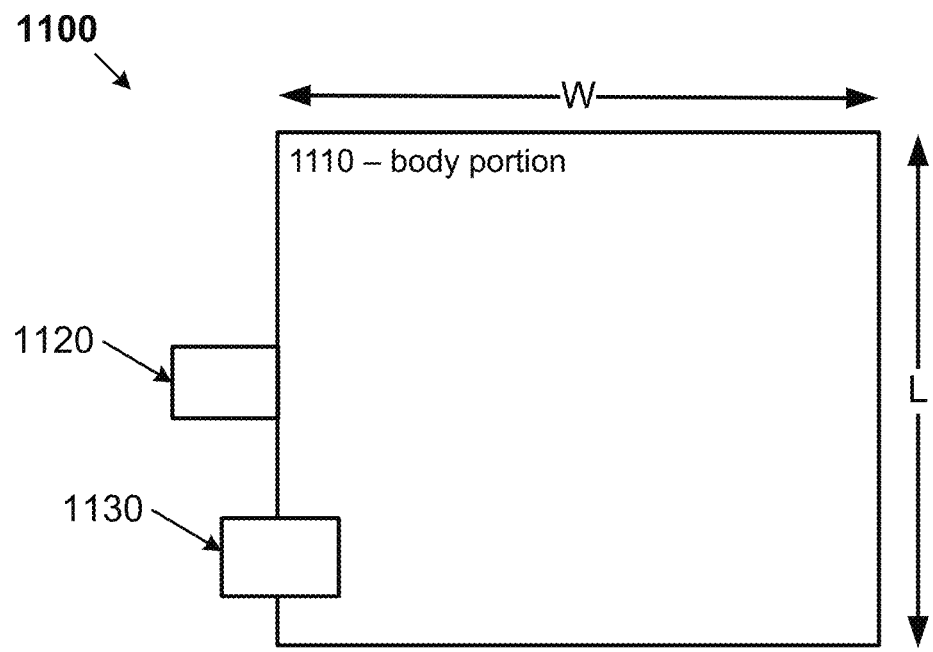
FIGS. 2A and 2B are schematic illustrations of the outer shell of the treatment system of FIG. 1.

As noted above, outer shell 1100 can enclose, cover, and/or support one or more of the other components or subsystems of treatment delivery component 1020, and maintain them in operative position with respect to a treatment portion TP of a user body UB to which treatment is to be delivered. As shown schematically in FIGS. 2A and 2B, outer shell 1100 may have a body portion 1110 and one or more fastener portions 1120 coupled to body portion 1110 and operable to secure body portion 1110 to, e.g., around a portion of user body UB. Body portion 1110 may be formed as a flexible sheet of material, such as fabric. Fastener portion(s) 1120 may be any suitable fastener that may be secured to one part of body portion 1110 and releasably coupled directly to another part of body portion 1110 (such as by a pin, clamp, hook, etc.) or via a corresponding second fastener portion(s) 1120, or to a corresponding element of the same fastener portion 1120 (e.g. fastener portion 1120 may be a zipper, snap, buckle, hook and loop fastener, etc., with one half secured to one part of body portion 1110 and the mating half secured to another part of body portion 1110). Outer shell 1110 may have a geometry and dimensions that are appropriate to fit to one or more portions of a user body UB to which treatment delivery component 1020 is to be applied to treat treatment portion TP. For example, if treatment delivery component 1020 is configured to be applied to a user leg UL of user body UB, then outer shell 1100 may have a length dimension L sufficient to extend over an appropriate length of user leg UL, e.g., from hip to foot, from hip to knee, from knee to foot, etc. Correspondingly, outer shell 1100 may have a width or circumferential dimension W sufficient to extend around the user leg UL. Although shown schematically in FIGS. 2A and 2B as a having a rectangular shape that may be configured to be fastened to encircle a user leg UL, body portion 1110 may have a more complex geometry to accommodate various anatomical portions of user body UB. For example, body portion 1110 may have a shape that can taper from one end to another to assume an approximately conical shape when secured to a user leg UL, to accommodate the larger diameter of user leg UL near the hip, and the smaller diameter near the ankle. Similarly, body portion 1110 may be a shape that can accommodate and enclose a user's foot. Such geometries are illustrated in embodiments described below. Body portion 1110 may similarly be configured to accommodate and conform to other portions of a user's anatomy, including arms or portions thereof, shoulders, hips, knees, back, head, and torso or portions thereof.

Figure 2B:
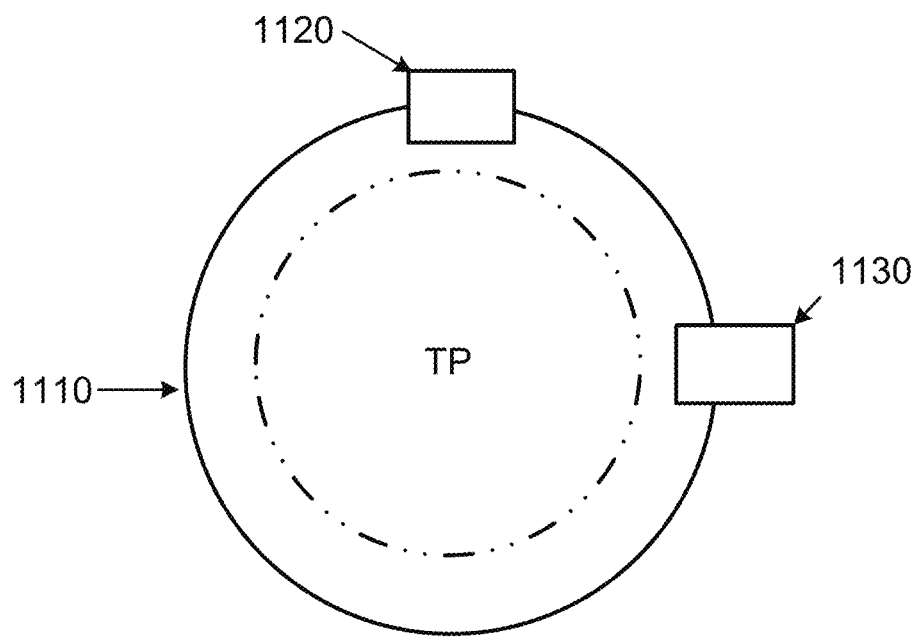

Outer shell 1100 may be configured to be changeable between a first, open configuration (as shown schematically in FIG. 2A) and a second, closed configuration (as shown in FIG. 2B) so that a user may dispose outer shell 1100 on the portion of user body UB to be treated (or dispose the portion of user body on the outer shell 1100) with the outer shell 1100 in the open configuration, and then transition outer shell 1100 to the closed configuration and secure it the closed configuration with fastener portion 1120. However, in some embodiments, outer shell 1100 may be configured to have only a closed configuration. For example, an outer shell configured to treat a user leg UL may be formed as a tube, similar to a pant leg, and the user may don outer shell 1100 like a pant leg, by sliding onto the user leg UL over the foot and up the leg and into the desired longitudinal position.

Outer shell 1100 is configured to enclose and/or support the other subsystems of treatment delivery component 1020 and to hold them in position around and/or against the treatment portion TP of user body UB. These functions of outer shell 1100 will be apparent from the description of the other subsystems below. In addition, outer shell 1100 may include one or more openings or passages 1130 through which one or more components of the other subsystems may pass, e.g., from the interior of the outer shell 1100 in its closed configuration to the exterior of outer shell 1100, e.g., to enable the component(s) of the other subsystem(s) to couple with control unit 1040 and/or to be accessed by the user. In some embodiments, each, any, or all of the other subsystems of treatment delivery component 1020 may be separate from outer shell 1100 and from each other, i.e., may be disposed in operative relationship with each other without coupling to each other, such as by stacking, nesting, etc. In other embodiments, each, any, or all of the other subsystems of treatment delivery component 1020 may be releasably coupleable to outer shell 1100 and/or to each other. In still other embodiments, each, any, or all of the other subsystems of treatment delivery component 1020 may be fixedly coupled to outer shell 1100 and/or to each other.

Pressure delivery component 1200 may be operated to provide either or both of two functions: a) it may be operated to selectively deliver pressure treatment or therapy to the treatment portion TP of user body UB; and/or b) it may be operated to interface with outer shell 1100 and one or both of thermal delivery component 1300 and other treatment delivery component 1400 to enhance the effectiveness of those components. Pressure delivery component 1200, also illustrated schematically in FIGS. 3A to 3E, may include a pressure applicator 1210, pressure connector 1260 releasably coupleable to pressure source 1600, and pressure conduit 1250 coupled between pressure connector 1260 and pressure applicator 1210. Thus, pressure applicator 1210 may apply to treatment portion TP of user body UB pressure supplied by pressure source 1600 via pressure connector 1260 and pressure conduit 1250.

Figure 3A:
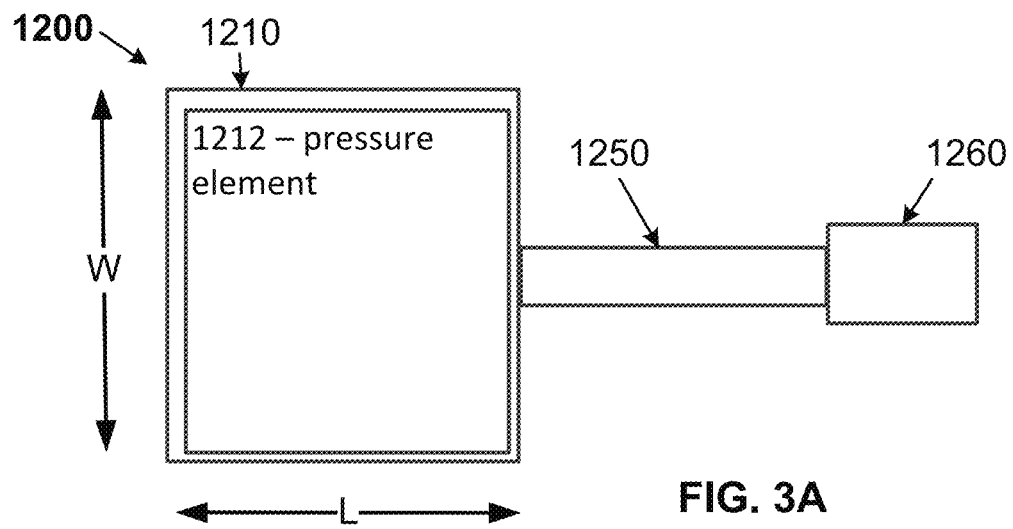
FIGS. 3A to 3O are schematic illustrations of the pressure delivery component of the treatment system of FIG. 1.
Figure 3B:
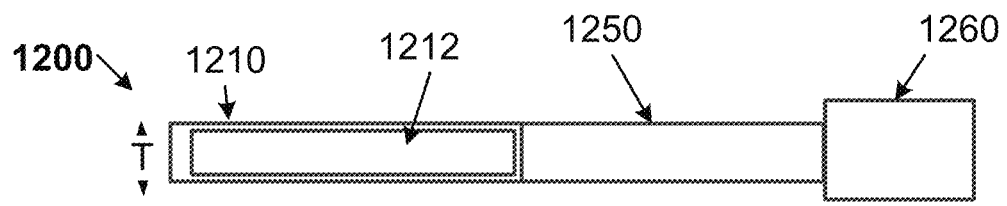
Figure 3C:
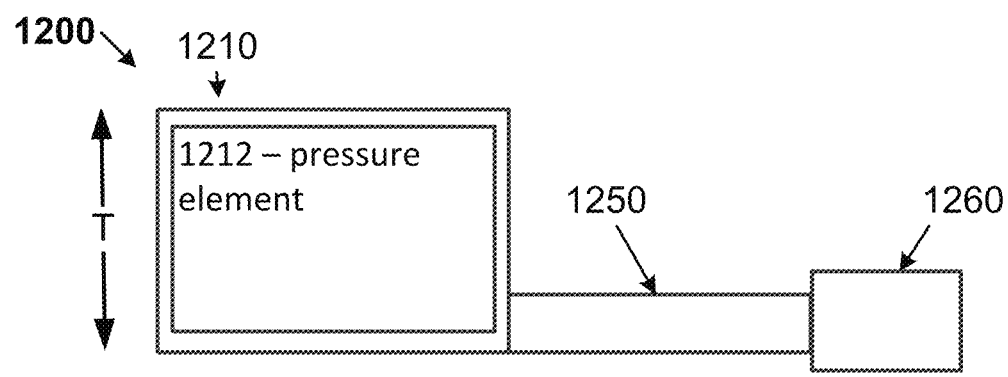

As shown schematically in FIG. 3A, as with outer shell 1100, pressure applicator 1210 may have a geometry and dimensions that are appropriate to fit to one or more portions of a user body UB to which treatment delivery component 1020 is to be applied to treat treatment portion TP. For example, if treatment delivery component 1200 is configured to be applied to a user leg UL of user body UB, then pressure applicator 1210 may have a length dimension L sufficient to extend over an appropriate length of user leg UL, e.g., from hip to foot, from hip to knee, from knee to foot, etc. Correspondingly, pressure applicator 1210 may have a width or circumferential dimension W sufficient to extend around the user leg UL.

Pressure (i.e., positive gauge pressure, higher than ambient, atmospheric pressure) may be provided in the form of pressurized fluid, e.g., pneumatic pressure from pressurized gas or hydraulic pressure from pressurized liquid, supplied by pressure source 1600. Correspondingly, pressure source 1600 may be a pump that supplies pressurized liquid, or a compressor that supplies pressurized gas. Pressure source 1600 need not be a powered device such as a pump or compressor, but instead may be a manually actuable device, such as a pump operable by a user's hand (like the bulb of a sphygmomanometer) or foot (like an inflator pump for an air mattress). Pressure applicator 1210 may include one or more pressure elements 1212, which may be volumes, cavities, spaces, or other enclosed portions that may receive the pressurized fluid. In some embodiments, pressure elements 1212 may include one or more bladders or other flexible walled enclosures that may be changeable from a collapsed, deflated, or lower volume configuration having a reduced dimension in a least one direction and an expanded, inflated, or higher volume configuration having an increased dimension in the at least one direction by receiving a volume of the pressurized fluid, and correspondingly may cause the pressure applicator 1210 to change from an unpressurized configuration to a pressurized configuration. This change in configuration is shown schematically in FIGS. 3B and 3C, which show pressure delivery component 1200 in a side view (rather than the top view of FIG. 3A). In the unpressurized configuration shown in FIG. 3B, pressure applicator 1210 has a relatively small thickness T. In contrast, in the pressurized configuration shown in FIG. 3C, pressure applicator 1210 has a relatively large thickness T.

The pressurized fluid may be conducted from pressure source 1600 via pressure conduit 1250, which may be implemented as one or more tubes or pipes of suitable internal diameter to convey the requisite volumetric flow rate of pressurized fluid to cause the pressure applicator 1210 to change from its unpressurized configuration to its pressurized configuration within a desired amount of time, and of appropriate construction to withstand or contain the maximum pressure at which pressurized fluid is to be provided by pressure source 1600.

Figure 3D:
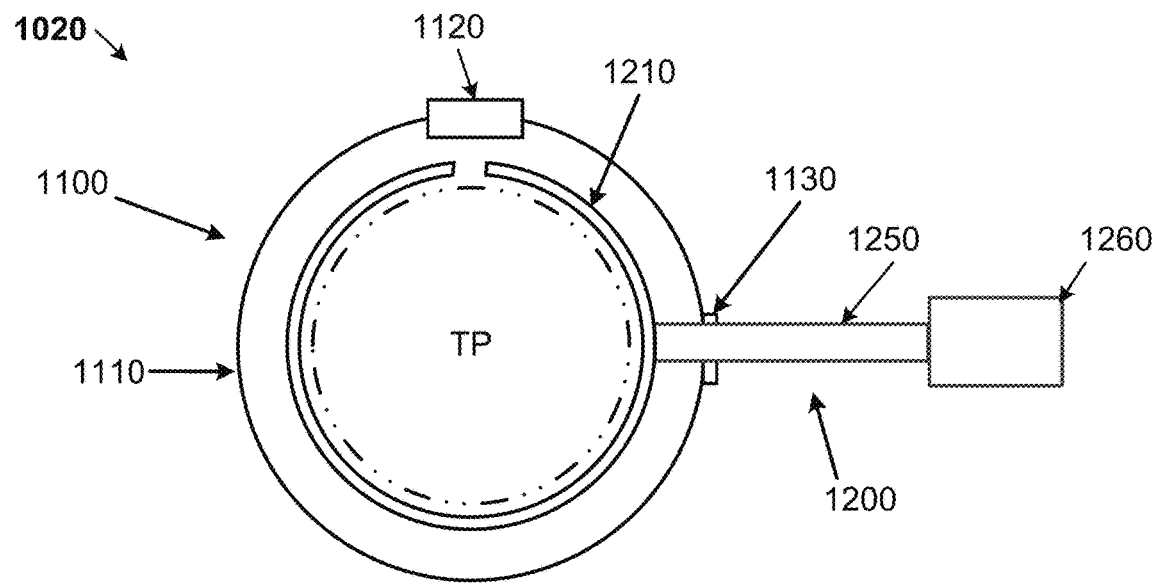
Figure 3E:
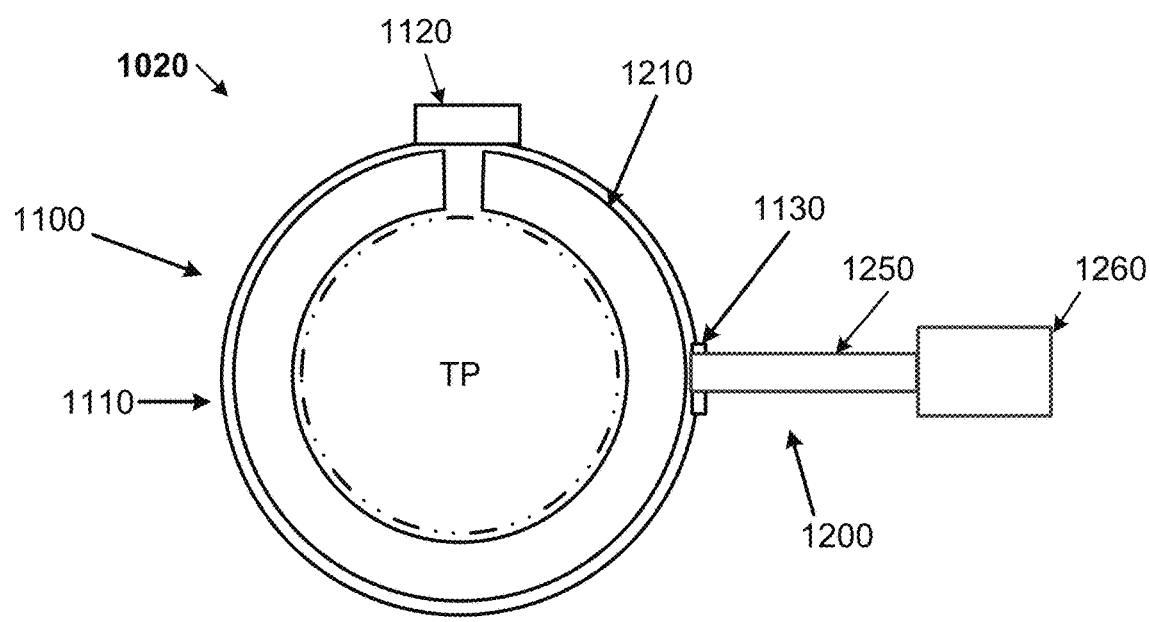
Figure 3F:
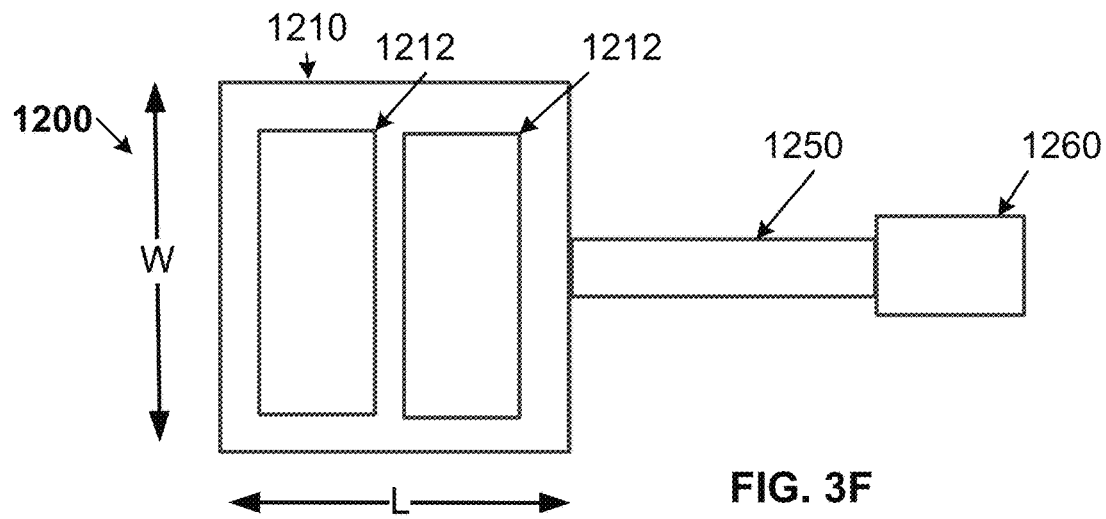
Figure 3G:
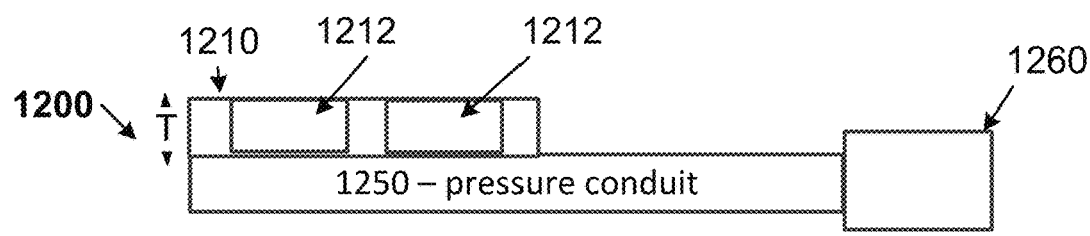

The interaction of pressure delivery component 1200 and outer shell 1100 is shown schematically in FIGS. 3D and 3E. For ease of illustration, treatment system 1000 is shown only with pressure delivery component 1200 and outer shell 1100, but the other subsystems of treatment system 1000 could also be present. Outer shell 1100 is shown disposed about a treatment portion TP of user body UB, in a closed configuration. Pressure delivery component 1200 is shown with pressure applicator 1210 disposed inside outer shell 1100, and with pressure conduit 1250 extending from pressure applicator 1210 through passage 1130. Pressure applicator is shown in FIG. 3D in its unpressurized configuration, with a relatively small thickness, and in FIG. 3E in its pressurized configuration, with a relatively larger thickness. As shown in FIG. 3E, in its pressurized configuration, pressure applicator 1210 is constrained by outer shell 1100, and therefore presses against, i.e., applies pressure to, treatment portion TP.

Although pressure applicator 1210 is shown in FIGS. 3D and 3E as being separate from outer shell 1110, as noted above pressure applicator 1210 can be releasably coupled to outer shell 1110 (by any suitable mechanism, such as buckles, zippers, hook and loop fasteners, etc.) or may be fixedly coupled to outer shell 1110 (such as by stitching, stapling, welding, gluing, etc.).

Figure 3H:
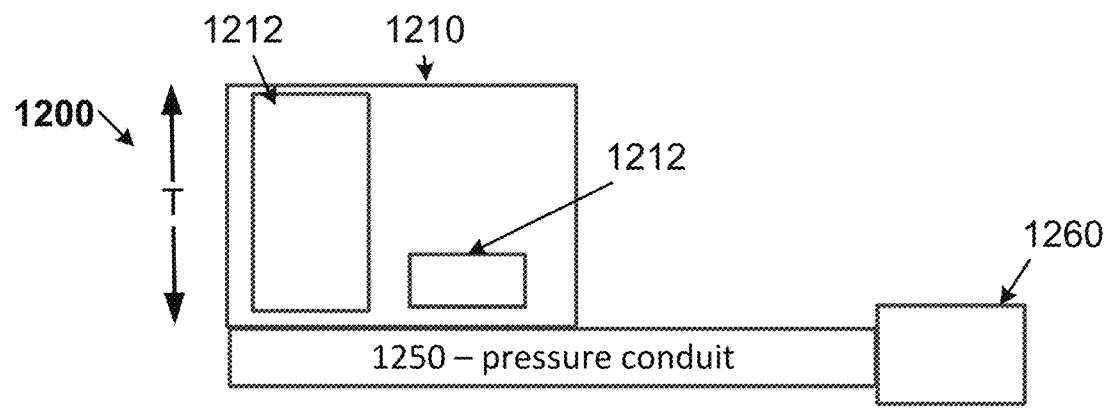
Figure 3I:
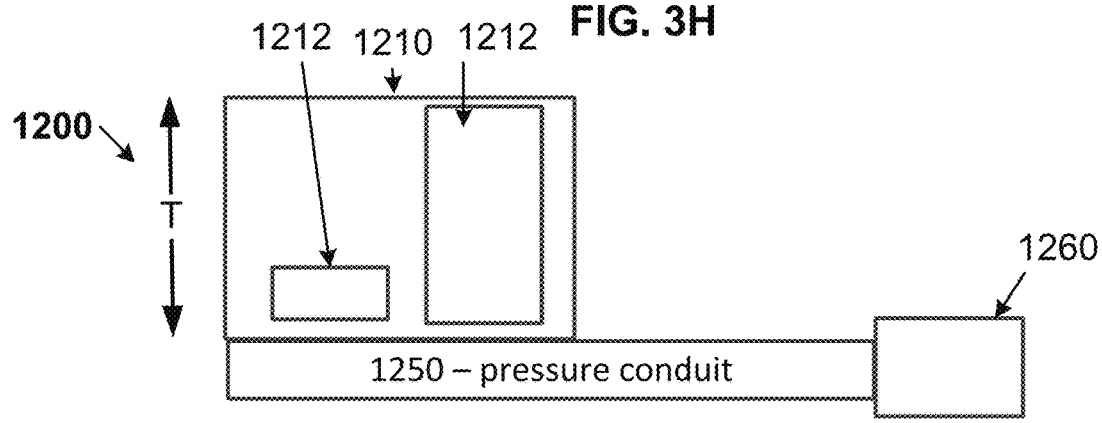

As noted above, pressure applicator 1210 may include more than one pressure element 1212. Multiple, independently actuable pressure applicators 1212 can enable differential application of pressure to different regions of treatment portion TP, as illustrated schematically in FIGS. 3F to 3I. Pressure applicator 1210 is shown with two independently actuable pressure applicators 1212, which are distributed along the length of pressure applicator 1210. As shown in FIGS. 3H and 3I, each pressure element 1212 can be selectively actuated to apply pressure to different lengthwise regions of treatment portion TP. For example, if treatment portion TP is a leg of a user, pressure elements 1212 can be selectively, independently actuated to apply pressure above and below the knee.

Figure 3J:
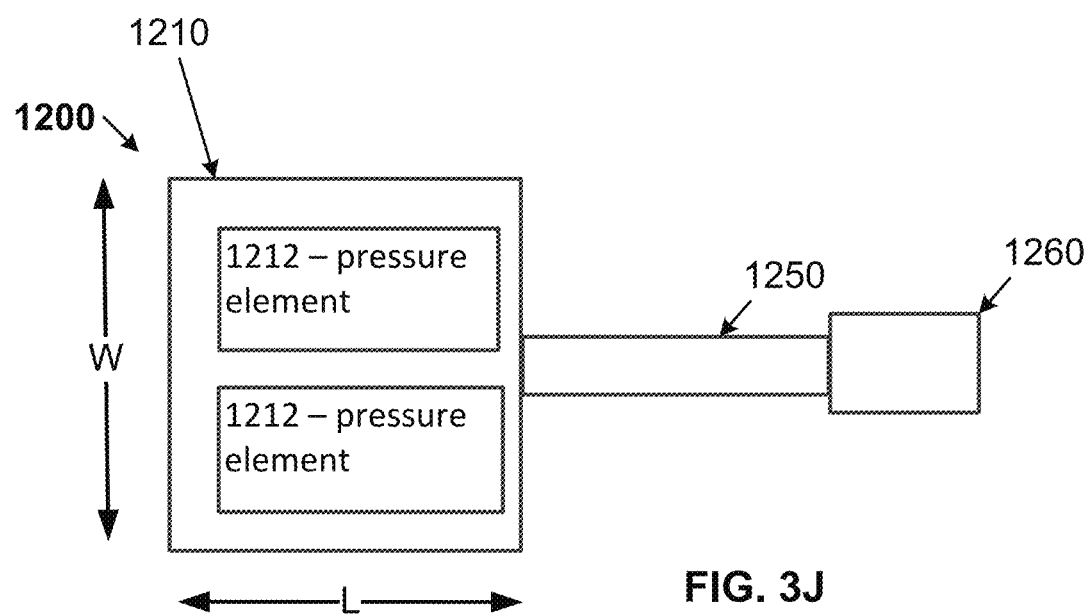
Figure 3K:
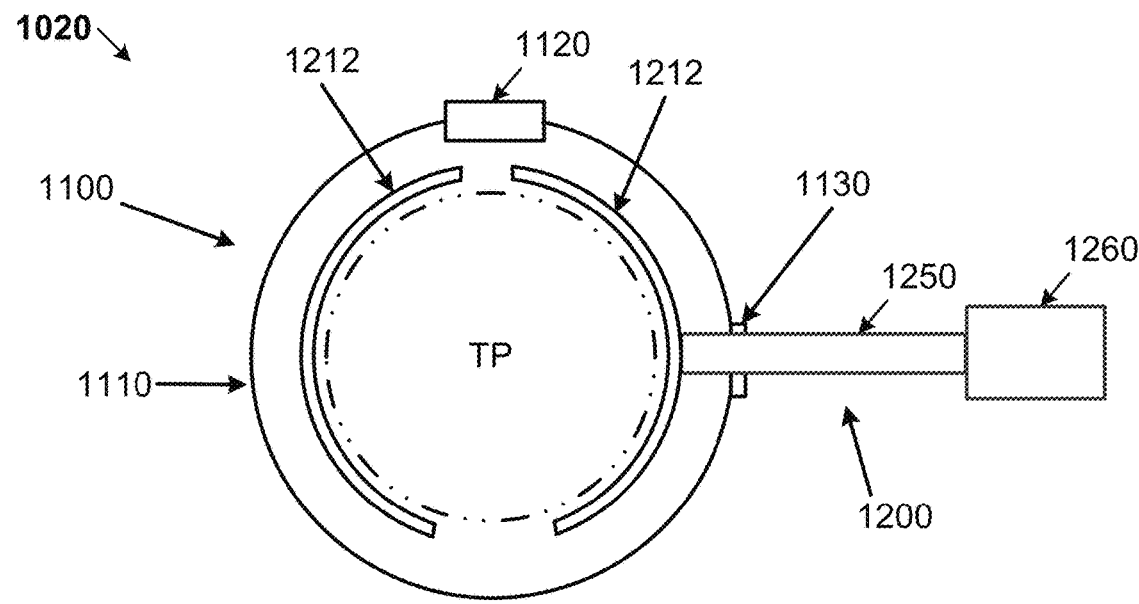
Figure 3L:
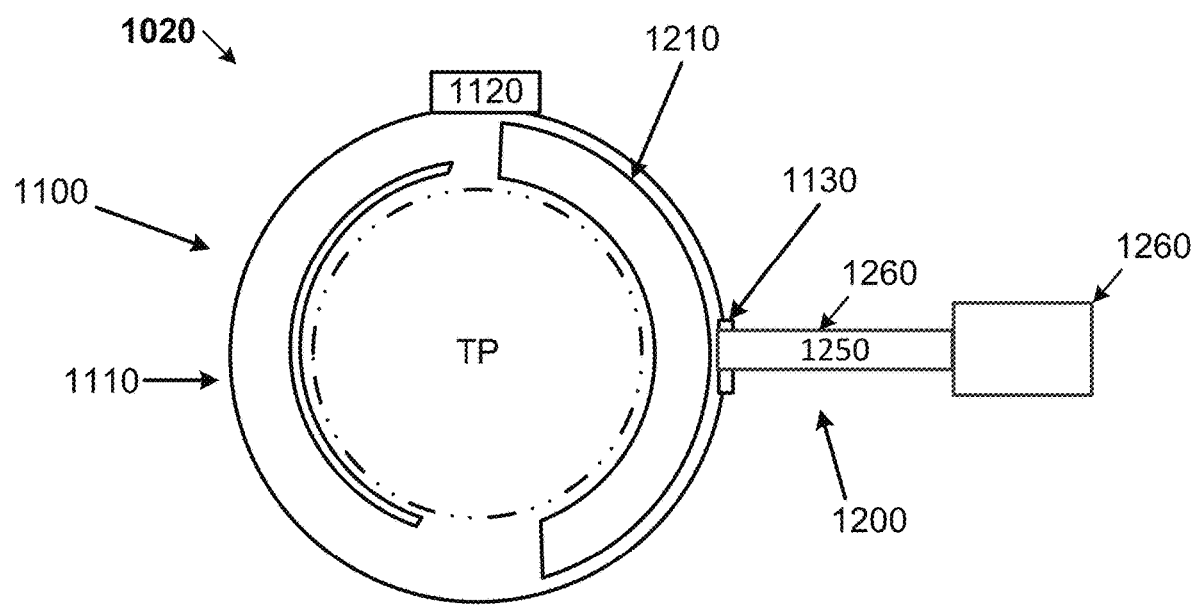

In some embodiments, multiple pressure elements 1212 can be distributed across the width of pressure applicator 1210, which may be configured to apply differential pressure treatment to different circumferential regions of treatment portion TP. This is shown schematically in FIGS. 3J to 3L.

Figure 3M:
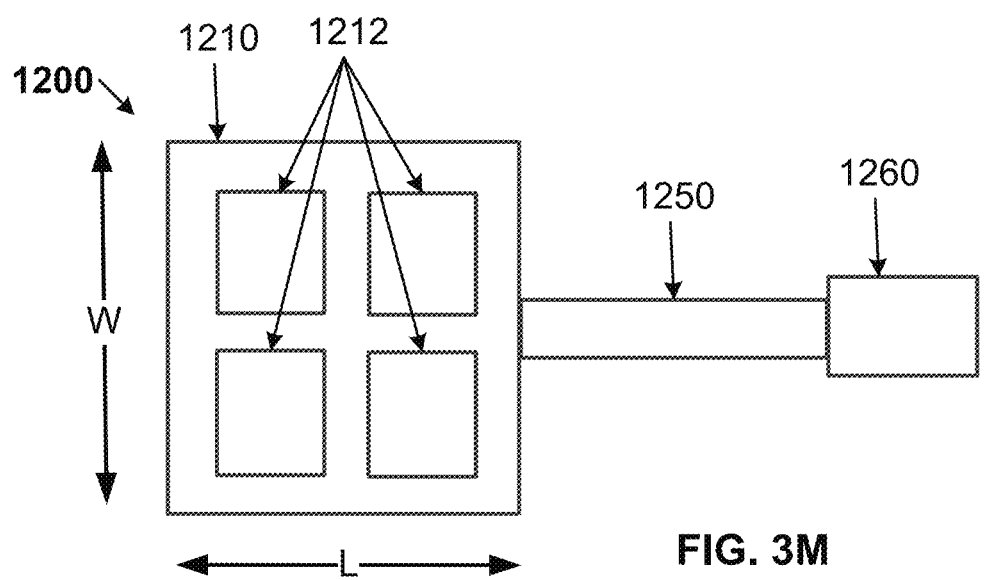
Figure 3N:
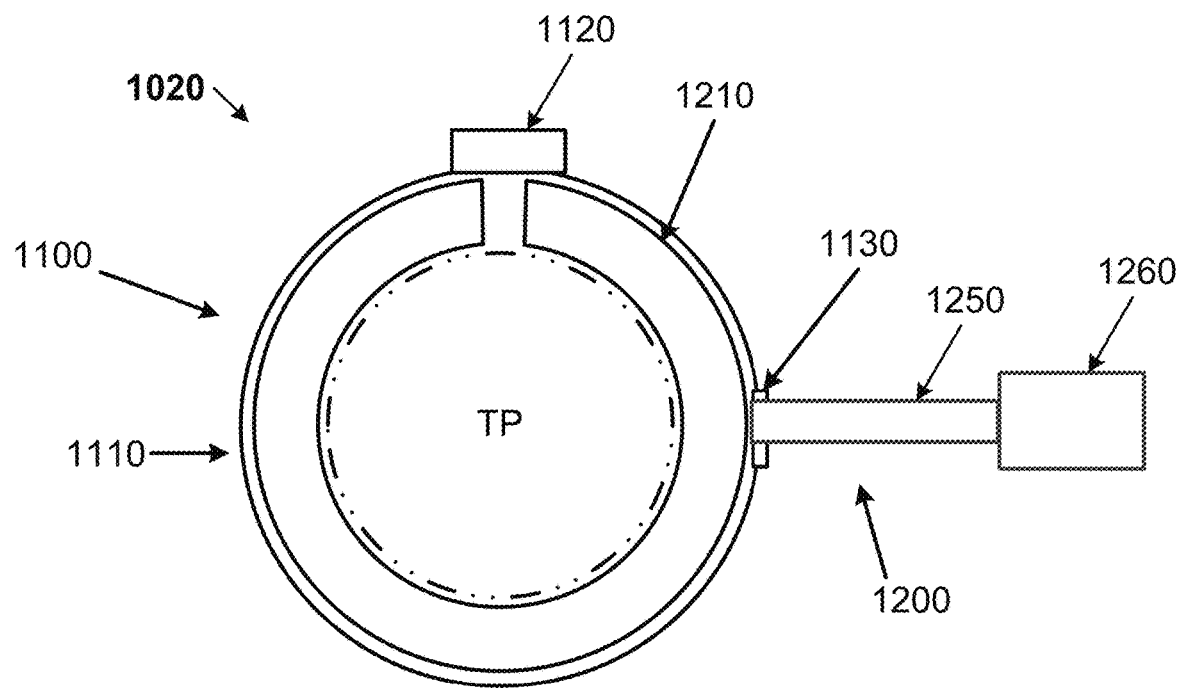
Figure 3O:
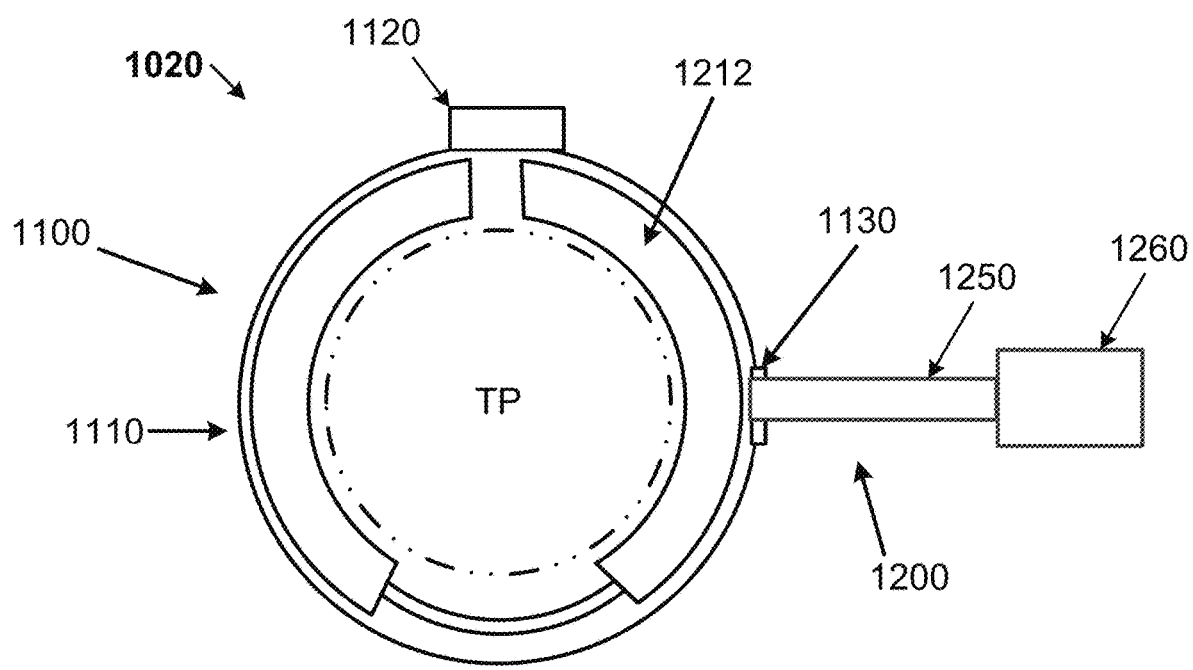

In some embodiments, multiple pressure elements 1212 can be distributed across both the width and length of pressure applicator, as shown schematically in FIG. 3M, and the pressure elements can be differentially actuated both lengthwise and circumferentially, essentially combining the operations illustrated schematically in FIGS. 3F to 3L.

Although two pressure elements 1212 are shown in FIGS. 3F to 3J, and four pressure elements are shown in FIG. 3M, this is only for ease of illustration, and pressure applicator 1210 can include any number of pressure elements 1212. Although shown schematically in these figures as being of the same size, pressure elements 1212 can be of different sizes from each other, with different lateral or longitudinal dimensions, which may depend on the shape of the treatment portion TP for which pressure applicator 1210 is configured. Although shown and described herein as being generally rectangular is shape or oriented approximately laterally and longitudinally, pressure elements 1212 can be of any shape, and may be oriented in any directly, e.g. obliquely, spiraling, etc. Although shown schematically in FIGS. 3D-3E, 3K-3L, and 3N-3O as encompassing substantially the entire circumference of treatment portion TP, in some embodiments pressure applicator 1210, and/or collectively all pressure elements 1212, may cover only a portion of the circumference of treatment portion TP. For example, if treatment portion TP is a leg of a user, pressure elements 1212 may be sized and disposed to overlay only the front of the leg (e.g., quadriceps) and not the back of the leg. Although in such embodiments pressure treatment may be delivered only to part of the treatment portion, pressure applicator 1210 can still provide the other functions and benefits described below of adapting thermal applicator 1310 and/or other treatment applicator 1410 to treatment portion TP, ensure good apposition for effective treatment, etc. A potential benefit of having smaller and/or fewer pressure elements is that the energy (e.g. electrical energy) required to expand pressure elements 1212 can be less, and/or the time required to expand them can be less for a given pressure source 1600.

In some embodiments, any or all of one or more pressure elements 1212 can be configured to have non-uniform changes in thickness along their length and/or width dimensions, i.e., to be asymmetric, to provide a desired distribution of pressure application to treatment portion TP and/or achieve particular desired positioning of treatment delivery component 1020 (and outer shell 1100, pressure applicator 1210, thermal applicator 1310, and/or other treatment applicator 1410) relative to treatment portion TP. This is illustrated schematically in FIGS. 3N and 3O, in which pressure element 1212 is configured to have a smaller thickness along portion of its width (or circumference) when actuated. For example, this reduced thickness may be desirable when the treatment portion TP is a user's leg, and less pressure is desired to be applied on the back of the leg, such as on the back of the knee. Such asymmetric configurations may be produced by the geometry of the bladder of envelop of material used to define the pressure element, or by employing different materials, e.g., more or less elastic, to form different portions of the pressure element. The pressure element can also be formed with internal, localized constraints on the extent to which the pressure element can expand. For example, opposed walls (inner and outer) of the pressure element can be selectively fused together (similar to the lines of fusion to form flow diverters in thermal applicators, as described herein) to limit or prevent expansion (by relative movement of the walls) in response to introduction of pressurized fluid.

Thermal delivery component 1300 may be operated to exchange thermal energy with the treatment portion TP in either or both of two thermal treatment modes—heating and/or cooling. Heating involves delivering thermal energy to the treatment portion TP, e.g., by contacting treatment portion TP (directly or through other intermediary structures, such as liner 1500) with a component having a temperature higher than body temperature (or skin temperature). Conversely, cooling involves withdrawing thermal energy from the treatment portion TP, e.g., by contacting treatment portion TP (directly or through other intermediary structures, such as liner 1500) with a component having a temperature lower than body temperature (or skin temperature). Thermal delivery component 1300, also illustrated schematically in FIGS. 4A to 4C, may include a thermal applicator 1310 having one or more thermal elements 1312, thermal connector 1360 releasably coupleable to thermal source 1700, and thermal conduit 1350 coupled between thermal connector 1360 and thermal applicator 1310. Thus, thermal applicator 1310 may deliver to, or receive from, treatment portion TP of user body UB thermal energy supplied by, or withdrawn by, thermal source 1700 via thermal connector 1360 and thermal conduit 1350. Thermal source 1700 may thus exchange thermal energy with thermal applicator 1310 (which in turn exchanges thermal energy with treatment portion TP).

Figure 4A:
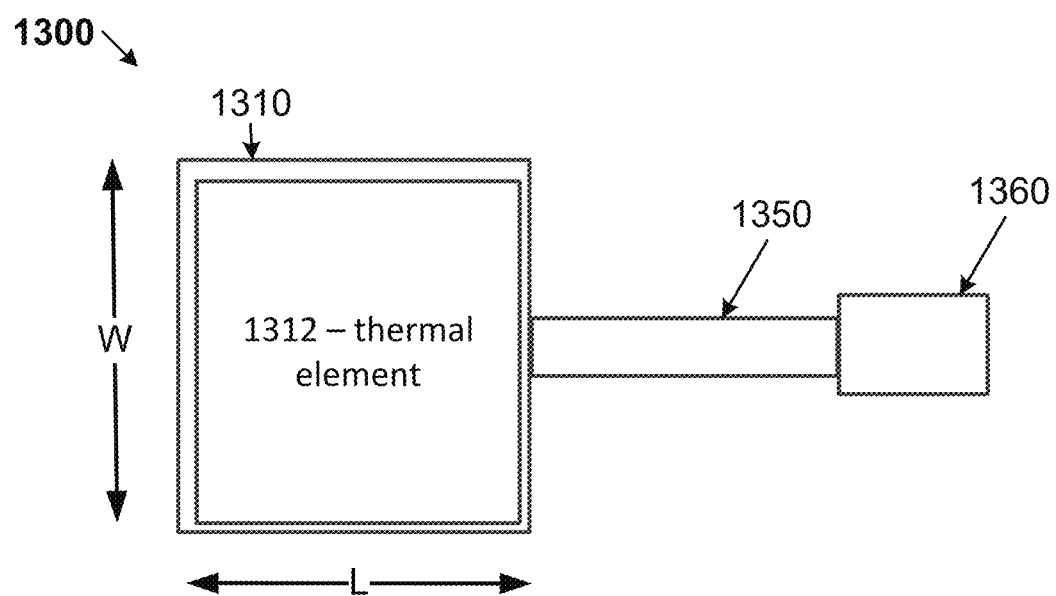
FIGS. 4A to 4C are schematic illustrations of the thermal delivery component of the treatment system of FIG. 1.

As shown schematically in FIG. 4A, as with outer shell 1100 and pressure applicator 1210, thermal applicator 1310 may have a geometry and dimensions that are appropriate to fit to one or more portions of a user body UB to which treatment delivery component 1020 is to be applied to treat treatment portion TP. For example, if treatment delivery component 1020 is configured to be applied to a user leg UL of user body UB, then thermal applicator 1310 may have a length dimension L sufficient to extend over an appropriate length of user leg UL, e.g., from hip to foot, from hip to knee, from knee to foot, etc. Correspondingly, thermal applicator 1310 may have a width or circumferential dimension W sufficient to extend around the user leg UL.

Thermal energy may be delivered to, and/or withdrawn from, treatment portion TP by thermal applicator 1310 (by thermal element(s) 1312) through any of a variety of mechanisms. These mechanisms may be implemented in whole or in part directly in thermal applicator 1310 (or thermal element(s) 1312) and/or in thermal source 1700 (and the thermal energy conveyed to/from thermal applicator 1310 via thermal conduit 1350). One approach involves direct conversion of electrical energy to thermal energy. For example, thermal energy can be generated by passing electric current through an electrical resistance, i.e., by resistive heating. Electrical heating can also be produced by induction heating, e.g., by passing alternating electric current through an electromagnet to produce alternating magnetic fields that produce eddy currents in a conductor, heating the conductor by Joule heating. Thermal energy can also be generated by one of more techniques for using electromagnetic radiation to transfer heat energy to thermal element(s) 1312, or to use thermal element(s) 1312 as the delivery device for the electromagnetic radiation. For example, tissue can be heated with electromagnetic radiation in the microwave, radio frequency (RF), and/or infrared (IR) portions of the frequency spectrum. Ultrasound may also be used to heat tissue. As another example, electrical heating/cooling can be produced by generating an electrical potential by passing electrical current across a thermoelectric material to generate a temperature differential. A heat pump can also be used to transfer thermal energy from a source and deliver it to thermal applicator 1310. One implementation of a heat pump is a thermoelectric cooler (TEC) or Peltier device, i.e., a solid-state heat pump, in which passage of a DC electric current through the device moves thermal energy from one side of the device to the other. The source of thermal energy can be implemented in any suitable manner. For example, the source of thermal energy can be heated fluid, ambient air, a portion of user body UB that is at a higher temperature than another portion, etc. Another implementation of a heat pump is a vapor compression refrigeration system, which circulates a refrigerant through a compressor, condenser, expansion valve, and evaporator. As another example, infrared energy (IR) can be used to deliver thermal energy to the tissue of the user. For example, the thermal element(s) 1312 may include IR lamps configured to generate IR waves that impinge or travel into the tissue and heat the tissue.

Another approach involves conversion of chemical energy to thermal energy, such as an oxidation reaction (e.g., air-activated, iron-based chemistry used in hand warmers), a crystalline phase change reaction (e.g., sodium acetate), or a combustion reaction (e.g., charcoal or lighter fluid). In another approach, thermal source 1700 can be implemented with a reservoir of material (gas, liquid, or solid) with a relatively high specific heat that is at a suitable temperature above body temperature. For example, a reservoir of hot water can be used as the source of thermal energy.

As a sink for thermal energy to be received from thermal applicator 1310, thermal source 1700 can receive the thermal energy through a variety of approaches. Thermal source 1700 can be implemented as a heat pump, to transfer thermal energy from thermal applicator 1310 and deliver it to a suitable heat sink. The same heat pump approaches described above for a source of thermal energy can be used, e.g., Peltier device and/or vapor compression refrigeration cycle. The heat pump used for cooling can be different from the heat pump used for heating. Optionally, with such heat pump implementations, the heat pump can be reversible so that it can operate alternatively to deliver thermal energy to, and receive thermal energy from, thermal applicator 1310. Similarly, thermal source 1700 can also be implemented by conversion of thermal energy to chemical energy, such as the reverse of the crystalline phase change reaction described above. Thermal source 1700 can also be implemented with a reservoir of material (gas, liquid, or solid) with a relatively high specific heat that is at a suitable temperature below body temperature. For example, a reservoir of cold water (including a mixture of water and ice) can be used as the sink for thermal energy. Any other suitable substance that can retain a cold temperature (e.g., dry ice) can be suitably used as a sink.

In some implementations, the exchange of thermal energy between thermal source 1700 and treatment portion TP, or between treatment portion TP and/or thermal source 1700 and the ambient environment, can be via pumping fluid (e.g., air, water, etc.) that may act as an agent to transfer the thermal energy. Treatment system 1000 may implement fluid movers to move the fluid to transfer the heat. For example, treatment system 1000 may implement fluid movers or flow controllers such as fans (e.g., to flow air across heat exchangers), pumps (e.g., to flow fluid past thermal source 1700 and/or thermal applicator 1310), valves (e.g., to direct the flow of fluid), etc.

Thermal source 1700 may function only to deliver thermal energy to thermal applicator 1310, may function only to receive thermal energy from thermal applicator 1310, or may function both to deliver and to receive thermal energy. Although shown in FIG. 1 as having a single thermal source 1700, treatment system 1000 may have more than one thermal source 1700. For example, treatment system 1000 may have one thermal source 1700 to deliver thermal energy and another thermal source 1700 to receive thermal energy, both for application to the same treatment portion TP. In another example, treatment system 1000 may have a separate thermal source 1700 to treat each of two or more treatment portions TP. In some implementations, thermal source 1700 can include a network of interconnected sink(s) and source(s) each accessible and available to a network of heat pumps and/or thermal applicators 1310 via a network of thermal conduits 1350 to deliver thermal modulation to multiple treatment portions TP or an expansive treatment portion TP. Many suitable options are disclosed in the incorporated '059 application.

Depending on the approach used to provide or receive thermal energy, thermal source 1700 may require a source of power. For example, if thermal source 1700 provides thermal energy by resistive heating, or if it provides or receives thermal energy by a Peltier device, it will require a source of electrical energy. Such electrical energy source may be incorporated into, or part of, thermal source 1700, or may be separate from but coupled to thermal source 1700, and still be part of treatment system 1000, such as a primary or secondary battery, or capacitor. Alternatively, the electrical energy source may be separate from thermal source 1700 and treatment system 1000, but thermal source 1700 and/or treatment system 1000 may have an interface to receive electrical energy from the source. Such sources may include DC or AC power (e.g., from a household electric source) with a direct connection, or an indirect connection such as inductive coupling, microwave transfer, laser power transfer, etc.

Thermal conduit 1350 can also be implemented in many different ways, appropriate to the corresponding implementations of thermal source 1700 and thermal applicator 1310, to provide a path for energy to move between thermal source 1700 and thermal applicator 1310, in a single direction or bi-directionally (depending on whether the particular implementation of thermal source 1700 is as a source, sink, or both source and sink for thermal energy). In some implementations, thermal conduit 1350 can operate by conductive, convective, or forced convective transfer, via fluid tubing, via heat pipe, via directed flow of air, passive distribution from one medium to another or within a medium, and/or a combination of approaches. In some implementations, thermal conduit 1350 can be wireless inductive energy transfer that is converted to heat by the receiving thermal applicator 1310. In other implementations, thermal conduit 1350 can be wired conductive electrical energy transfer that is converted to heat by resistive heating by the receiving thermal applicator 1310. In one approach to transferring thermal energy, thermal conduit 1350 can rely on the mechanism of conduction. For example, thermal conduit 1350 can be simply a highly thermally conductive material (e.g., metal) disposed between thermal source 1700 and thermal applicator 1310. Rather than a solid material, thermal conduit can be a thermally conductive liquid. In another approach, thermal conduit 1350 can rely on fluid transport to transfer thermal energy. For example, a liquid heated at an interface (e.g., a heat exchanger) at thermal source 1700 can be conveyed through a tube or pipe to thermal applicator 1310 and transfer thermal energy at an interface (e.g. another heat exchanger) at thermal applicator 1310. Cooled liquid can be returned through a separate tube or pipe to thermal source 1700 to be reheated. The tubing can be formed of any material suitable for conveying the fluid. The tubing at the heat exchanger associated with the thermal applicator 1310 may be thermally conductive (e.g., gold, aluminum, or copper), whereas the tubing in other portions of thermal conduit 1350 may be relatively non-conductive (e.g., polymer), and may optionally be covered with a separate insulating material to further reduce thermal energy transfer between the fluid in the tubing and the environment. The tubing can be of any suitable size, shape or form. For example, in some implementations the tubing can be of a suitably narrow or broad area of cross section and follow a serpentine or other suitably convoluted path to increase a surface area of contact between the fluid path and a heat exchanger or thermal source 1700.

Thermal source 1700 and thermal delivery component 1300 can be implemented with any of the techniques, structures, and component described in the incorporated '059 application.

Figure 4B:
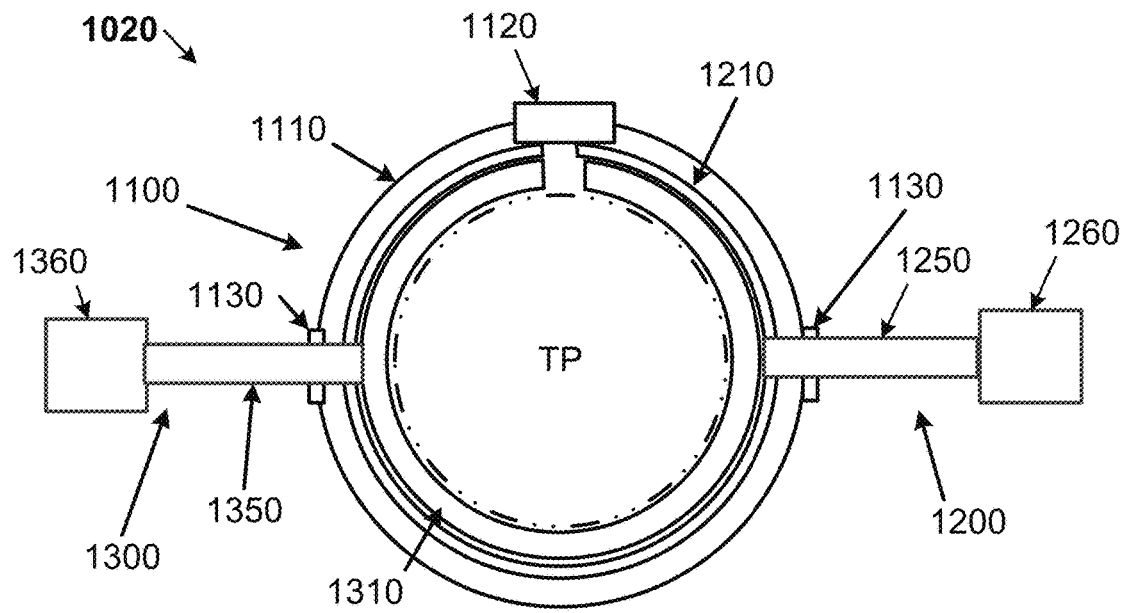
Figure 4C:
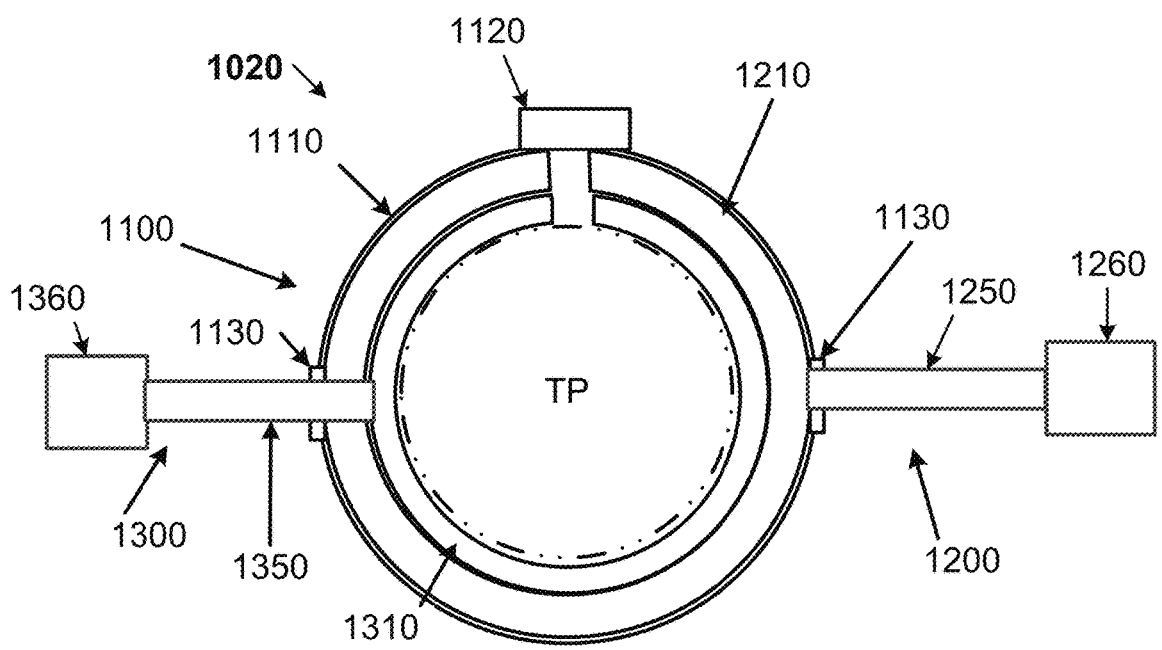

The interaction of thermal delivery component 1300 with pressure delivery component 1200 and outer shell 1100 is shown schematically in FIGS. 4B and 4C. For ease of illustration, treatment system 1000 is shown only with thermal delivery component 1300, pressure delivery component 1200, and outer shell 1100, but the other subsystems of treatment system 1000 could also be present. Outer shell 1100 is shown disposed about a treatment portion TP of user body UB, in a closed configuration. Pressure delivery component 1200 is shown with pressure applicator 1210 disposed inside outer shell 1100, and with pressure conduit 1250 extending from pressure applicator 1210 through a passage 1130. Thermal delivery component 1300 is shown with thermal applicator 1310 disposed inside outer shell 1100 and pressure applicator 1210, and with thermal conduit 1350 extending from thermal applicator 1310 through another passage 1130. The interaction between thermal conduit 1350 and passage 1130 can aid in maintaining the position of thermal applicator 1310 relative to outer shell 1100. Although shown in FIGS. 4B and 4C as being disposed through body portion 1110 of outer shell 1100, the passage 1130 through which thermal conduit 1350 extends may also be formed through pressure applicator 1210. Pressure applicator 1210 may have one or more welds or seams between, and partially defining, individual pressure elements (not shown) and passage 1130 may be formed in, or adjacent to, such weld or seam. As described herein, pressure applicator 1210 may be integrally formed with, or fixedly secured to, body portion 1110, and passage 1130 may therefore be a single opening formed through both structures. Pressure applicator 1210 is shown in FIG. 4B in its unpressurized configuration, with a relatively small thickness, and in FIG. 4C in its pressurized configuration, with a relatively larger thickness. As shown in FIG. 4C, in its pressurized configuration, pressure applicator 1210 is constrained by outer shell 1100, and therefore presses against, i.e., applies pressure to, thermal applicator 1310, and through thermal applicator 1310 to treatment portion TP.

As described above for pressure applicator 1210, although thermal applicator 1310 is shown in FIGS. 4B and 4C as being separate from outer shell 1110 and from pressure applicator 1210, thermal applicator 1310 can be releasably coupled to outer shell 1110 and/or pressure applicator 1210 (by any suitable mechanism, such as buckles, zippers, hook and loop fasteners, clips, etc.) or may be fixedly coupled to outer shell 1110 and/or pressure applicator 1210 (such as by stitching, stapling, welding, gluing, etc.).

Pressure delivery component 1200 can be operated to maintain a baseline, or minimum, pressure in pressure applicator 1210, by which pressure applicator 1210 can apply sufficient pressure to thermal applicator 1310 to maintain good contact between thermal applicator 1310 and treatment portion TP, i.e., sufficient contact to provide good heat transfer between thermal applicator 1310 and treatment portion TP. Optionally, pressure delivery component 1200 can also be operated at higher pressure(s) to provide pressure therapy via pressure applicator 1210, as described above, applying the pressure therapy through thermal applicator 1310 (whether or not thermal applicator 1310 is actively providing thermal treatment).

Other treatment delivery component 1400 may be configured to provide any one or more of various treatment modalities. As used herein, "other treatment" means a treatment with a modality other than thermal or pressure, so an "other treatment delivery component" is a treatment delivery component that is not exclusively either a thermal delivery component or a pressure delivery component. "Other treatment" may also be referred to herein as "supplemental treatment," e.g., is the other treatment is combined with (or supplemental to) pressure and/or thermal treatment. As described in more detail herein, the "other treatment delivery component" may be incorporated into, or integrated with, one of both of a thermal delivery component and a pressure delivery component, or may be a separate component. In some embodiments, the other treatment delivery component 1400 may be completely independent of the other components of treatment delivery component 1020. Such non-thermal, non-pressure treatment modalities may include based on electrical energy (such as transcutaneous electrical nerve stimulation (TENS), electromyostimulation (EMS), neuromuscular electrical stimulation (NEMS), and/or electroporation), on magnetic fields, on other electromagnetic radiation (such as light for phototherapy, or pulsed electromagnetic field (PEMF)), on chemistry (such as delivery of large or small molecule therapeutic compositions), on mechanical force (such as vibration), or combinations thereof (for example, electroporation can enhance delivery of chemical therapeutics into cells in treatment portion TP). For each modality, other treatment delivery component 1400 can include, as shown schematically in FIG. 1 and FIG. 5A, other treatment applicator 1410 with one or more other treatment elements 1412, other treatment conduit 1420, and other treatment connector 1460, by which the other treatment modality can be delivered from other treatment source 1800. Each of those components are configured appropriately for the other treatment modality. For example, for an electrical energy based treatment modality, such as TENS, other treatment applicator 1410 (which may also be referred to as electrical treatment applicator 1410 because the treatment modality is based on electrical energy) can include an array of other treatment elements 1412 (or electrical treatment elements 1412), each of which is an electrode configured to be applied to the surface (e.g., skin) of treatment portion TP so that electrical energy can be supplied by conduction to treatment portion TP. Correspondingly, other treatment conduit 1410 (or electrical treatment conduit 1410) can be an electrical conductor (wire(s), etc.), and other treatment connector 1460 (or electrical treatment connector 1460) can be an electrical connector, and these components can convey electrical energy from other treatment source 1800 (or electrical treatment source 1800), which may be, for example, an electrical pulse generator. Any or all of the electrodes can also be used to confirm apposition or electrical contact with the surface of treatment portion TP, so that controller 1900 can determine which, if not all, of the electrodes should receive electrical energy. Other treatment applicator 1410 can include a substrate for support of other treatment elements 1412, which can have a variety of constructions. For example the substrate can be a sheet of woven or non-woven fabric, mesh, or other material, which is preferably relative inelastic, so that it does not stretch (and thus change the relative spacing of other treatment elements 1412). Other treatment applicator 1410 can include multiple layers, with different treatment modalities on different layers, e.g., a layer with electrodes for delivery of electrical and/or magnetic treatment modalities, and a layer with vibration actuators or transducers to deliver a mechanical treatment modality. As discussed herein, other treatment applicator 1410 can be integrated with pressure applicator 1210 and/or thermal applicator. In other embodiments, other treatment applicator can be integrated with liner 1500 (discussed below).

In another example, for a chemistry based treatment modality, such as delivery of a drug or other chemical therapeutic, other treatment applicator 1410 (which can also be referred to as chemical applicator 1410) can include one or more other treatment elements 1412 (or chemical elements 1412), each of which may be a drug delivery device such as a needle, array of microneedles, drug delivery patch, etc. by which the drug can be delivered to (e.g., dermally) or into (e.g., transdermally, subcutaneously, intramuscularly) treatment portion TP. Correspondingly, other treatment conduit 1450 (or chemical conduit 1450) can be a tube, and other treatment connector 1460 (or chemical connector 1460) can be a fluid connector, by which a drug (e.g., in fluid form, in solution, etc.) can be conveyed from other treatment source 1800 (or chemical source 1800), which may be, for example a reservoir of the drug. Many therapeutics are delivered transdermally, and the delivery of the therapeutic depends on many factors including temperature and the quality of the contact. A therapeutic could be applied or added to an other treatment applicator, such as in the form of a membrane that is pressurized and forced to have good apposition with the skin for delivery. This can be done with any membrane surface using the pressure applicators described herein.

For other treatment modalities such as TENS, it may be desirable for the other treatment elements 1412 (or electrical elements 1412, e.g., electrodes) to be arranged on a substrate (such as a non-conductive, flexible fabric) in a specific spatial relationship, and for that spatial relationship to be maintained independently of the size of the treatment portion TP of the user. It may therefore be desirable for the substrate to be relatively inelastic, i.e., not to stretch or distort when applied to treatment portion TP, and also not to wrinkle, crease, or fold. The overlying relationship of pressure applicator 1210 can aid in minimizing distortion, etc. of other treatment applicator 1410.

Other treatment modalities could be used for many other conditions, such as muscle soreness after exercise, muscle ischemia, muscle trauma, phantom limb pain, muscle cramps, night leg cramps and spasms, promotion of tissue healing, etc.

Figure 5A:
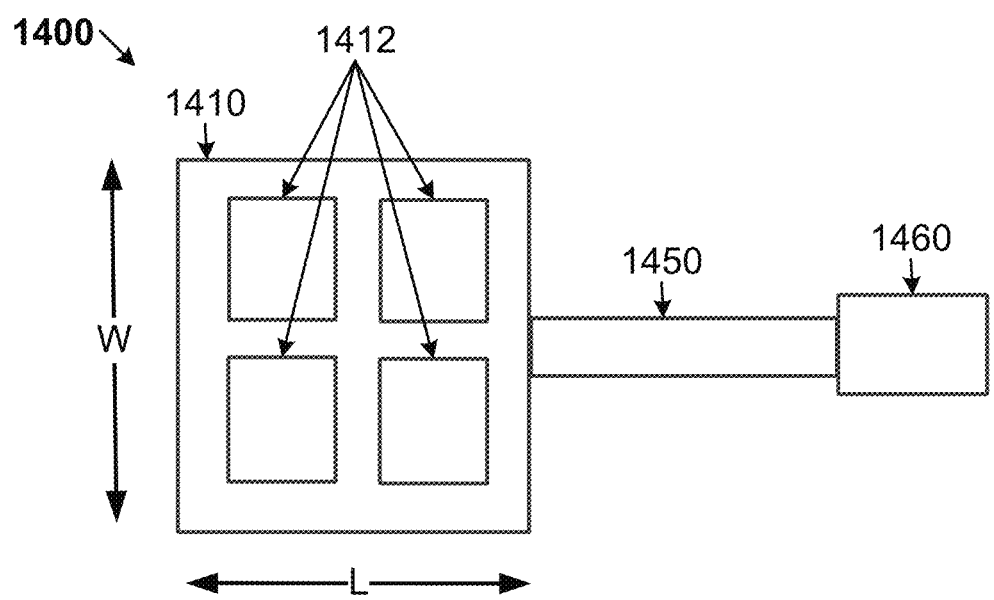
FIGS. 5A to 5C are schematic illustrations of the other thermal delivery component of the treatment system of FIG. 1.

As shown schematically in FIG. 5A, as with outer shell 1100, pressure applicator 1210, and thermal applicator 1310, other treatment applicator 1410 may have a geometry and dimensions that are appropriate to fit to one or more portions of a user body UB to which treatment delivery component 1020 is to be applied to treat treatment portion TP. For example, if treatment delivery component 1020 is configured to be applied to a user leg UL of user body UB, then other treatment applicator 1410 may have a length dimension L sufficient to extend over an appropriate length of user leg UL, e.g., from hip to foot, from hip to knee, from knee to foot, etc. Correspondingly, other treatment applicator 1410 may have a width or circumferential dimension W sufficient to extend around the user leg UL. In other embodiments, other treatment applicator 1410 may be smaller in width or length than the overlying pressure applicator 1210 or outer shell 1100, e.g., if a smaller area of the treatment portion is desired to be treated with the other treatment modality.

Figure 5B:
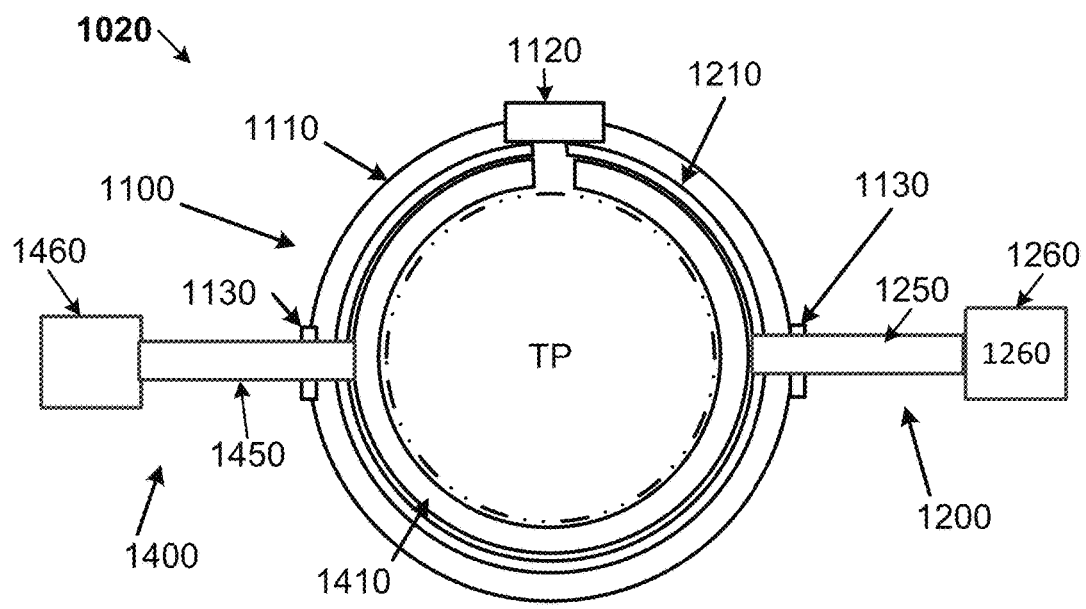
Figure 5C:
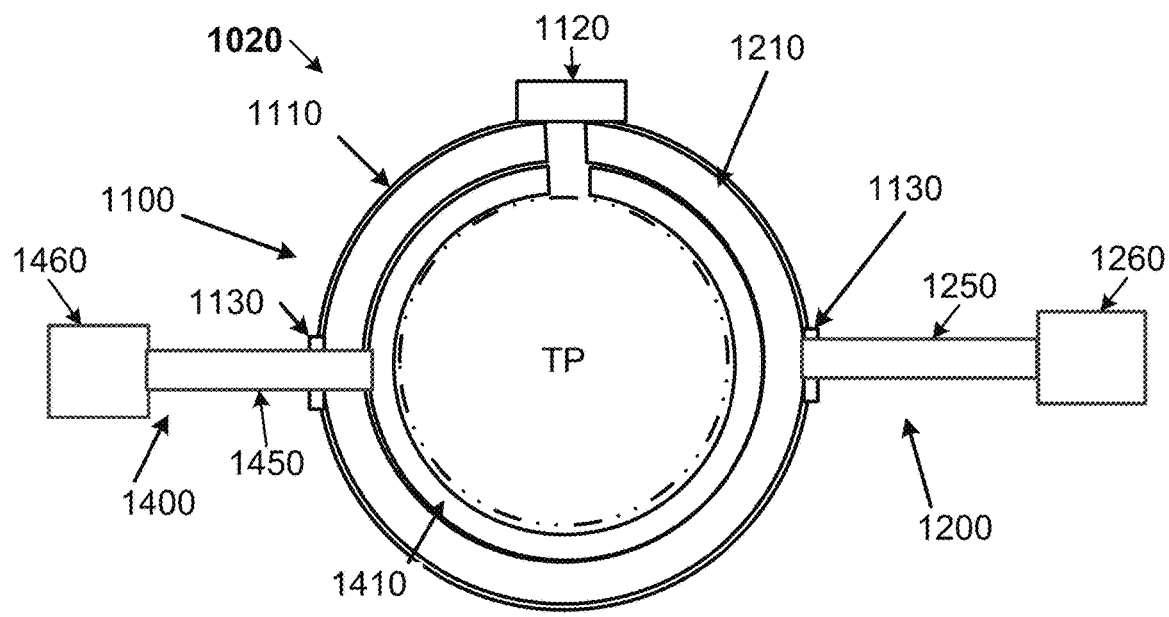

The interaction of other treatment delivery component 1400 with pressure delivery component 1200 and outer shell 1100 is shown schematically in FIGS. 5B and 5C. For ease of illustration, treatment system 1000 is shown only with other treatment delivery component 1400, pressure delivery component 1200, and outer shell 1100, but the other subsystems of treatment system 1000 could also be present. Outer shell 1100 is shown disposed about a treatment portion TP of user body UB, in a closed configuration. Pressure delivery component 1200 is shown with pressure applicator 1210 disposed inside outer shell 1100, and with pressure conduit 1250 extending from pressure applicator 1210 through a passage 1130. Other treatment delivery component 1400 is shown with other treatment applicator 1410 disposed inside outer shell 1100 and pressure applicator 1210, and with other treatment conduit 1450 extending from other treatment applicator 1410 through another passage 1130. Pressure applicator is shown in FIG. 5B in its unpressurized configuration, with a relatively small thickness, and in FIG. 5C in its pressurized configuration, with a relatively larger thickness. As shown in FIG. 5C, in its pressurized configuration, pressure applicator 1210 is constrained by outer shell 1100, and therefore presses against, i.e., applies pressure to, other treatment applicator 1410, and through other treatment applicator 1410 to treatment portion TP.

As described above for pressure applicator 1210 and thermal applicator 1310, although other treatment applicator 1410 is shown in FIGS. 5B and 5C as being separate from outer shell 1110 and from pressure applicator 1210, other treatment applicator 1410 can be releasably coupled to outer shell 1110 and/or pressure applicator 1210 (by any suitable mechanism, such as buckles, zippers, hook and loop fasteners, clips, etc.) or may be fixedly coupled to outer shell 1110 and/or pressure applicator 1210 (such as by stitching, stapling, welding, gluing, etc.).

As with thermal applicator 1310, pressure delivery component 1200 can be operated to maintain a baseline, or minimum, pressure in pressure applicator 1210, by which pressure applicator 1210 can apply sufficient pressure to other treatment applicator 1410 to maintain good contact between other treatment applicator 1410 and treatment portion TP, i.e., sufficient contact to provide good application of the treatment modality (such as good electrical contact for electrical energy based treatment modalities). And, optionally, pressure delivery component 1200 can also be operated at higher pressure(s) to provide pressure therapy via pressure applicator 1210, as described above, applying the pressure therapy through other treatment applicator 1410 (whether or not other treatment applicator 1410 is actively providing treatment).

Although shown and described above as being separate from the pressure delivery component 1200 and thermal delivery component 1300, other treatment delivery component 1400 can be integrated with one of the other treatment delivery components. For example, for an electrical energy based other treatment modality, other treatment elements 1410 can be incorporated into a surface of thermal applicator 1310 (if used) or into a surface of pressure applicator 1210 (if treatment delivery component 1020 is not configured to include a thermal delivery component 1300).

Other treatment delivery component 1400 can also be separate from, but used in conjunction with, both pressure delivery component 1200 and thermal delivery component 1300. For example, other delivery component 1400 can be disposed between thermal delivery component 1300 and treatment portion TP, and configured to have a relatively low thermal insulation value so as not to materially reduce the amount of thermal energy deliverable via thermal delivery component 1300. In some embodiments, other treatment applicator 1410 can be disposed on treatment portion TP independently of the other components of treatment delivery component 1020, and held in operative position on treatment portion TP by disposing thermal applicator 1310 and/or pressure applicator 1210 on top of other treatment applicator 1410.

As noted above, treatment delivery component 1020 can also include a liner 1500. Treatment delivery component 1020 can be configured so that liner 1500 is the only, or substantially the only, portion of treatment delivery component 1020 that contacts the skin of the user, e.g., the skin on the treatment portion TP of the user body UB. This may be a desirable configuration if treatment delivery component 1020 is to be used by multiple users, or by the same user for many treatment delivery sessions, so that the liner can be washed, or replaced, between treatment sessions and/or between users, to provide for more hygienic delivery of treatment. Liner 1500 may thus be configured to be releasably coupleable to outer shell 1100, pressure applicator 1210, thermal applicator 1310, and/or other treatment applicator 1410. In other embodiments, liner 1500 may be fixedly coupled to one or more of the other components of treatment delivery component 1020. In use, a previously unused liner 1500 may be coupled to the other component(s) of treatment delivery component 1020 before treatment delivery component 1020 is operatively engaged with a user to deliver treatment. After the treatment is delivered to the user, the liner 1500 may then be removed and washed before use by the same user for a subsequent treatment delivery session, or by a different user. Alternatively, the liner 1500 may be discarded and replaced by a new liner 1500. Liner 1500 may also be formed of, or be treated with, material having antimicrobial properties. Liner 1500 may also be configured to provide containment, support, and/or aid in coupling or desired alignment of any of the applicators. For example, liner 1500 may be coupled to, and define with, outer shell 100 and/or pressure applicator 1210 a sleeve or pocket into which thermal applicator 1310 may be disposed.

Liner 1500 may be formed of material(s) that provide desired properties for liner 1500. For example, if liner 1500 is to be used in conjunction with thermal applicator 1310, and thus be disposed between thermal applicator 1310 and treatment portion TP, it may be desirable that liner 1500 have a minimal insulation value, so that it imposes a minimal loss of thermal energy transfer between thermal applicator 1310 and treatment portion TP. This thermal property may be achieved with a fabric woven with fine fibers and a high fiber count or tight weave, so that it traps very little air between the fibers, and a very thin layer of insulating air between thermal applicator 1310 and treatment portion TP. Alternative, in some applications it may be desirable for liner 1500 to have a larger insulation value, to produce a significant difference in temperature between the surface of thermal applicator 1310 and the surface of treatment portion TP (i.e., the user's skin, for example, if thermal applicator 1310 is circulating ice water or other very cold fluid, it may be desirable not to expose the user's skin to that temperature). In some embodiments, a user may be provided with multiple interchangeable liners 1500 with different properties to use for different treatment regimens. If liner 1500 is to be used with an other treatment applicator 1400 employing an electrical energy based treatment modality, it may be desirable for liner 1500 to be electrically conductive. In some embodiments, liner 1500 may have openings or apertures therethrough to permit electrical elements 1412 (e.g. electrodes) from an overlying electrical applicator to contact the surface of treatment portion TP therethrough. In other embodiments, liner 1500 and other treatment applicator 1410 may be integrated, e.g. liner 1500 may incorporate other treatment elements 1412. Such an arrangement may be advantageous in that a user may obtain a treatment delivery component 1020 that includes a pressure treatment component 1200 and/or thermal treatment component 1300, and separately or subsequently obtain an integrated liner 1500/other treatment applicator 1410 and releasably couple to the other components to enable delivery of the other treatment modality. If liner 1500 is to be used with an other treatment applicator employing a chemistry based treatment modality, it may be desirable for liner 1500 to be permeable to the drug or other chemical therapeutic delivered by other treatment delivery component 1400.

In some embodiments, liner 1500 may be coupled to outer shell 1100, pressure applicator 1210, thermal applicator 1310, and/or other treatment applicator 1410 so as to enclose, support, or otherwise aid in retaining or maintaining in a desired position any one or more of the applicators. For example, liner 1500 may be coupled to outer shell 1100 to form a pocket in which thermal applicator 1310 may be releasably disposed (as described in more detail below).

As noted above, treatment delivery component 1020 can also include one or more sensors 1550. Such sensors could include sensors to measure parameters such as temperature (in a single location, or multiple locations to measure temperature gradient), pressure (in a single location, or multiple locations to measure pressure gradient), electrical field, electrical current, magnetic field, EKG, EMG, chemical concentration, motion, acceleration, user vital signs (blood pressure, heart rate, $O_2$ saturation, blood flow (e.g. by laser doppler or similar measurement), respiration rate, etc.) and/or other parameters that may be indicative of the status or efficacy of any of the treatment modalities being applied to a user by treatment system 1000. Sensor(s) 1500 may be disposed in operative relationship with the treatment portion TP of the user, or some other portion of user body UB. For example, one or more sensors may be disposed in contact or close proximity with the surface (e.g., skin) of treatment portion TP, including between the treatment portion and the most proximal layer of treatment delivery component 1020 (e.g., liner 1500, other treatment applicator 1410, thermal applicator 1410, or pressure applicator 1210). Additionally or alternatively, one or more sensors may be disposed in operative relationship with one or more components of treatment delivery component 1020, such as disposing a pressure sensor to measure a pressure in each of one or more pressure elements 1212 (such as a bladder), or disposing an EMG sensor adjacent to (or as part of) a muscle stimulator. The output(s) of such sensor(s) 1500 may be communicated to controller 1900, such as by wired or wireless communication channel(s). The effectiveness, accuracy, and/or reliability of such sensors 1550 can be enhanced by good apposition with the surface of treatment portion, using any of the components and techniques described below. Similarly, the repeatability of sensor measurements can be improved by disposing the sensors on a non-expanding membrane or fabric.

Controller 1900 can be any suitable compute device that can electronically control functioning of treatment system 1000. As shown in FIG. 1, controller 1900 can be configured to be appropriately suited for the corresponding implementation of treatment system 1000, including any suitable hardware-based computing device and/or a multimedia device, such as, for example, a server, a microprocessor, a desktop compute device, a smartphone, a tablet, a wearable device, a laptop and/or the like.

Figure 6:
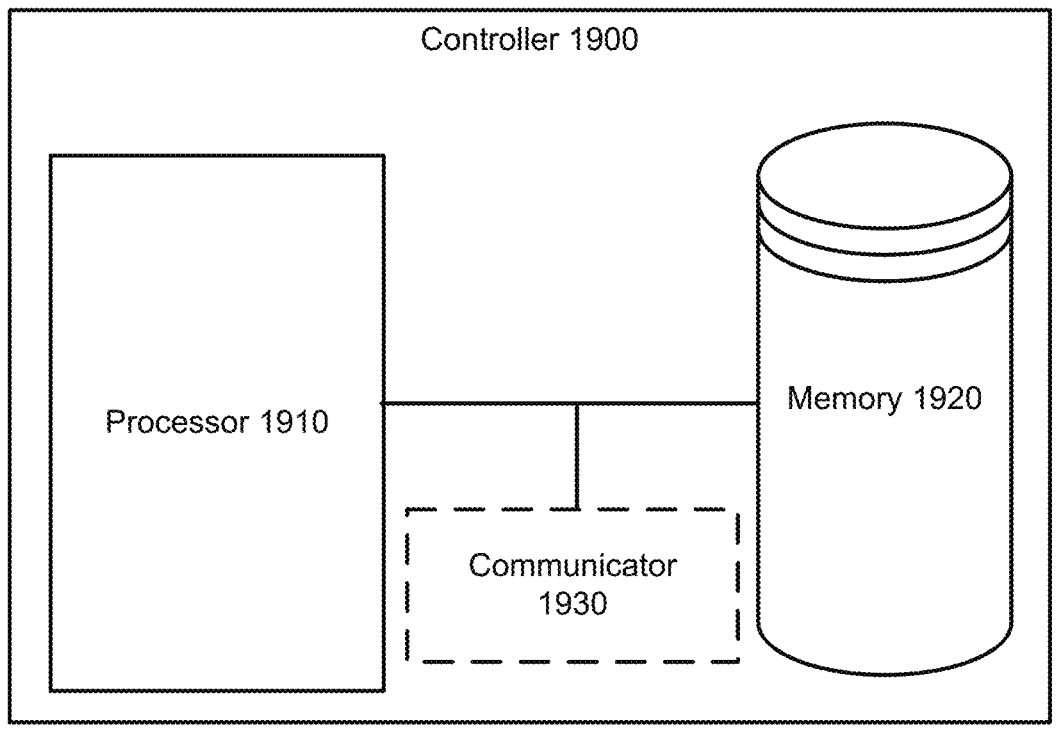
FIG. 6 is a schematic illustration of the controller of the treatment system of FIG. 1.

FIG. 6 is a schematic block diagram of controller 1900, according to an example implementation. Controller 1900 includes a processor 1910, a memory 1920 (e.g., including data storage), and optionally a communicator 1930.

Processor 1910 can be, for example, a hardware based integrated circuit (IC) or any other suitable processing device configured to run and/or execute a set of instructions or code. For example, processor 1910 can be a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. Processor 1910 can be operatively coupled to memory 1920 through a system bus (for example, address bus, data bus and/or control bus).

Processor 1910 can be configured to send instructions to one or more components of treatment system 1000 to operate the components. For example, processor 1910 can generate and/or receive instructions and send instructions to activate and/or deactivate pressure source 1600, thermal source 1700, and/or other treatment source 1800, one or more fluid movers or flow controllers to convey fluid via the pressure conduit 1250, thermal conduit 1350, or other treatment conduit 1450, one or more portions of pressure applicator 1210, thermal applicator 1310, and/or other treatment applicator 1410, following the associated instructions. In some embodiments, processor 1910 can be configured to maintain logs or schedules of treatment and associated instructions used to carry out the treatment. In some embodiments, the instructions used to carry out the treatment are adjusted by processor 1910 based on information provided by or related to the user. Processor 1910 can also be configured to maintain a log of information related to the user (e.g., identifier of the user, time and date of treatment, settings and preferences associated with the user (e.g., temperature settings for thermal treatment, pressure settings for pressure treatment, other settings for other treatment modalities, duration of treatment, etc.), timetable of treatment administration, etc.). Processor 1910 can store data and/or files associated with a user and/or a treatment approach or protocol. In some embodiments, processor 1910 can receive feedback from sensor(s) 1550 and/or the user (e.g., behavioral responses including perception of degree of pain, level of pain relief experienced, physiological responses like heart rate, breathing, blood pressure, etc., and input provided by the user like sensitivity to heat, sensitivity to cold temperatures, etc.). Data from sensors 1550 can be used by processor 1910 to monitor and/or modify operation of control unit 1040 and/or treatment delivery component 1020. For example, if processor 1910 receives temperature data from a sensor 1550 that indicates a temperature at the surface of treatment portion TP exceeds a high temperature threshold, or falls below a low temperature threshold, processor 1910 may suspend or terminate operation of thermal delivery component 1300 to avoid injury to treatment portion TP. Similarly, if processor 1910 receives blood flow data from a sensor 1550 that indicates a blood flow rate in treatment portion TP falls below a threshold flow rate, processor 1910 may suspend or terminate operation of pressure delivery component 1200 to avoid injury to treatment portion from lack of blood supply. Processor 1910 may cause data received from one or more sensor 1550 to be displayed to the user on display 1960. Data from multiple sensors 1550 may be used by processor 1910 to determine additional information about the user. For example, data from a blood flow sensor and a pressure sensor could be used in combination to determine the pressure at which blood flow is cut off, to calculate a blood pressure (diastolic and/or systolic) of the user.

Memory 1920 of controller 1900 can be, for example, a random access memory (RAM), a memory buffer, a hard drive, a read-only memory (ROM), an erasable programmable read-only memory (EPROM), and/or the like. Memory 1920 can store, for example, one or more software modules and/or code that can include instructions to cause processor 1910 to perform one or more processes, functions, and/or the like (e.g., receiving signals from sensors 1500, sending signals to fluid movers and/or flow controllers, sending signals to thermal treatment elements, etc.). In some embodiments, memory 1920 can include extendable storage units that can be added and used incrementally. In some implementations, memory 1920 can be a portable memory (for example, a flash drive, a portable hard disk, and/or the like) that can be operatively coupled to processor 1910. In other instances, memory 1920 can be remotely operatively coupled with controller 1900. For example, a remote database server can serve as a memory and be operatively coupled to the compute device.

Communicator 1930 can be a hardware device operatively coupled to processor 1910 and memory 1920 and/or software stored in memory 1920 executed by processor 1910. Communicator 1930 can be, for example, a network interface card (NIC), a Wi-Fi™ module, a Bluetooth® module and/or any other suitable wired and/or wireless communication device. Furthermore, communicator 1930 can include a switch, a router, a hub and/or any other network device. Communicator 1930 can be configured to connect controller 1900 to a communication network. In some instances, communicator 1930 can be configured to connect to a communication network such as, for example, a near field communication (NFC) network, the Internet, an intranet, a local area network (LAN), a wide area network (WAN), a metropolitan area network (MAN), a worldwide interoperability for microwave access network (WiMAX®), an optical fiber (or fiber optic)-based network, network using HTTP and other protocols, networks implementing WLAN (including 802.11a/b/g/n and other radio frequency-based protocols and methods), network supporting analog transmissions, Global System for Mobile Communications (GSM), 3G/4G/LTE, a Bluetooth® network, a virtual network, network implementing communications via ZigBee, EnOcean, TransferJet, Wireless USB, and/or any combination thereof.

In some instances, communicator 1930 can facilitate receiving and/or transmitting data and/or files through a communication network. In some instances, a received file can be processed by processor 1910 and/or stored in memory 1920 and used to control the operation of treatment system 1000 as described herein.

Figure 7:
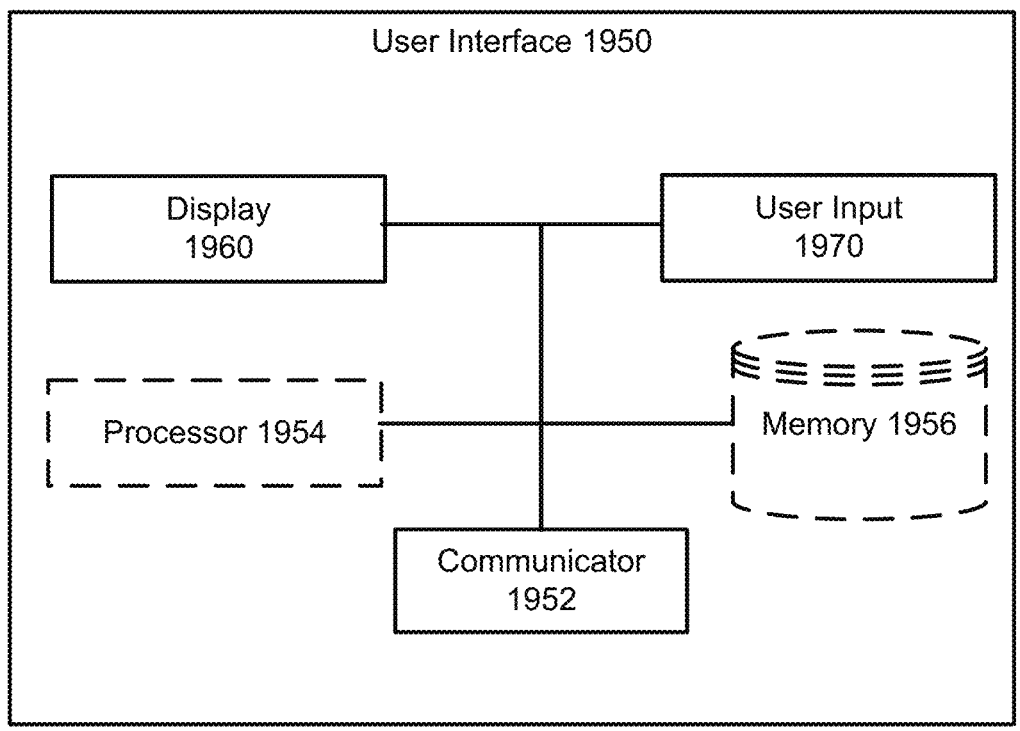
FIG. 7 is a schematic illustration of the user interface of the treatment system of FIG. 1.

As noted above, control unit 1040 can include a user interface 1950. As shown schematically in FIG. 7, user interface 1950 can include a communicator 1952, an optional processor 1954, and an optional memory 1956, which may function, and be implemented, in similar fashion to processor 1910, memory 1920, and communicator 1930, as described above for controller 1900. Communicator 1952 may communicate with optional communicator 1930 of controller 1900, and/or may communicate directly with, for example, processor 1910. In addition, user interface 1950 may include a display 1960 and a user input 1970. Display 1960 may provide a visual display to the user operating parameters for treatment system 1000, such as pressure for pressure delivery component 1200 (e.g. for pressure source 1600, and/or any or all of pressure elements 1212), temperature for thermal delivery component 1300 (e.g. for thermal source 1700 and/or any thermal element 1312), and/or any relevant operating parameter(s) for other delivery component 1400 (including other treatment source 1800 and/or any other treatment element 1412), time (planned treatment time, elapsed actual treatment time, and/or other time parameters for any of the treatment delivery components), and/or other information of relevance to the user.

User input 1970 may provide input mechanisms (dial, knob, button, user interactive panel, and/or the like) by which the user can provide inputs to the user input 1970 to be communicated to controller 1900 (e.g., processor 1910) In some implementations, display 1960 and user input 1970 may be combined, e.g., as a touch screen.

Although shown in FIG. 1 as being part of control unit 1040, in some embodiments user interface 1950 may be implemented on a device that is physically separate from control unit 1040 (and its other subsystems, such as pressure source 1600, thermal source 1700, other treatment source 1800, and controller 1900). For example, user interface 1950 may be implemented in software operating on a separate device such as a smartphone or tablet (e.g., in a dedicated app), and the touch screen of the smartphone or tablet may combine the functions of display 1960 and user input 1970, so that the device can control operation of the control unit 1040.

Figure 8:
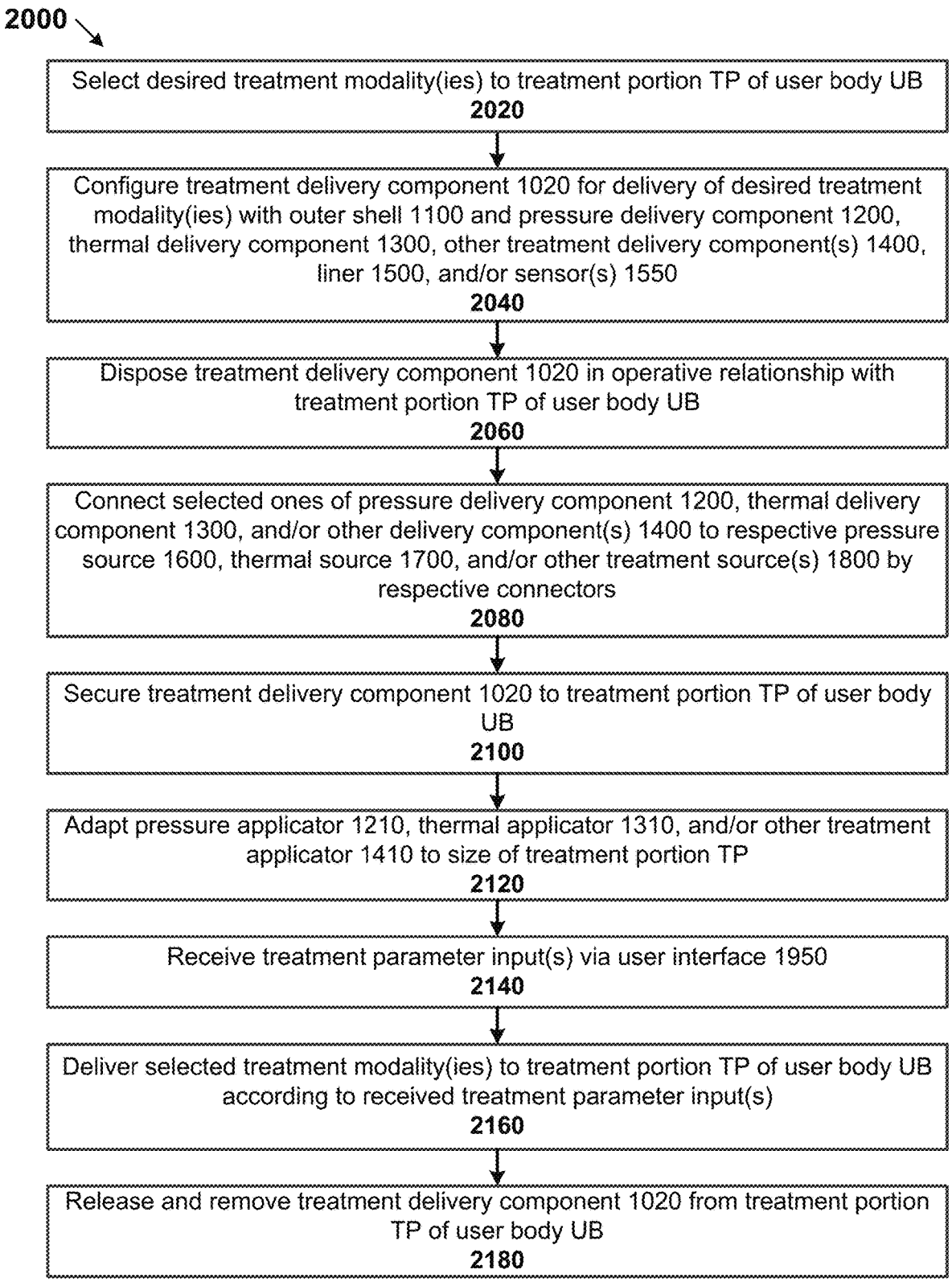
FIG. 8 is a flow chart of a method of treatment of a user with the treatment system of FIG. 1, accordingly to an embodiment.

An exemplary method of treatment of a user with treatment system 1000 is illustrated in FIG. 8. As shown in FIG. 8, method 2000 includes a series of steps or actions—many of these steps may be optional, the steps may be performed in sequences other than those shown in FIG. 8, and other steps may be included in the treatment of a user. At 2020, one or more desired treatment modalities (e.g., pressure, thermal, and/or other) may be selected for treatment of treatment portion TP of user body UB. The selection may be made by the user and/or by a third party (physician or other medical practitioner, trainer, physical therapist, etc.). At 2040, treatment delivery component 1020 of treatment system 1000 can be configured for delivery of the desired treatment modality(ies). For example, outer shell 1100 may be associated with or coupled to one or more of liner 1500, pressure delivery component 1200, thermal delivery component 1300, other treatment delivery component 1400, and/or sensor(s) 1550. At 2060, the configured treatment delivery component 1020 may be disposed in operative relationship with treatment portion TP of user body UB. For example, if the treatment portion TP is a leg of a user, treatment delivery component 1020 may be disposed on a floor, table, or other surface in an open configuration, and the user can place the leg on the inside surface of treatment delivery component 1020 (e.g., on liner 1500, if included in the configuration). At 2080, the selected delivery components (e.g. pressure delivery component 1200, thermal delivery component 1300, and/or other delivery component 1400) can be connected to their respective sources (pressure source 1600, thermal source 1700, and/or other treatment source 1800) by their respective connectors (pressure connector 1260, thermal connector 1360, and/or other treatment connector 1460). At 2100, treatment delivery component 1020 can be secured to treatment portion TP of user body UB, for example by fastening fastener portion 1120 of outer shell 1100. For example, if the treatment portion TP is a leg of a user, treatment delivery component 1020 be secured around the leg with fastener portion 1120. At 2120, pressure applicator 1210, thermal applicator 1310, and/or other treatment applicator 1410 can be adapted to the size of the treatment portion TP of user body UB. For example, if the treatment portion TP is a leg of a user, the selected applicators can be adjusted to fit the circumference of the leg (e.g., to engage in appropriate apposition, with no slack, folds, etc.) as described above, and in more detail below. At 2140, treatment parameter input(s) can be received by treatment system 1000 via user interface 1950. For example, the user may provide inputs (or a third party, such as those identified above, may provide the inputs on behalf of the user) to user interface 1950 to select a desired treatment regime, e.g., select from among available options for pressure treatment programs, thermal treatment programs, and/or other treatment programs. At 2160, the selected treatment modalities (with selected treatment regimens/programs) can be delivered to treatment portion TP of user body UB by treatment system 1000. After completion of delivery of the selected treatment modalities, treatment delivery component 1020 can be released from, and then removed from treatment portion of user body UB.

Figure 9A:
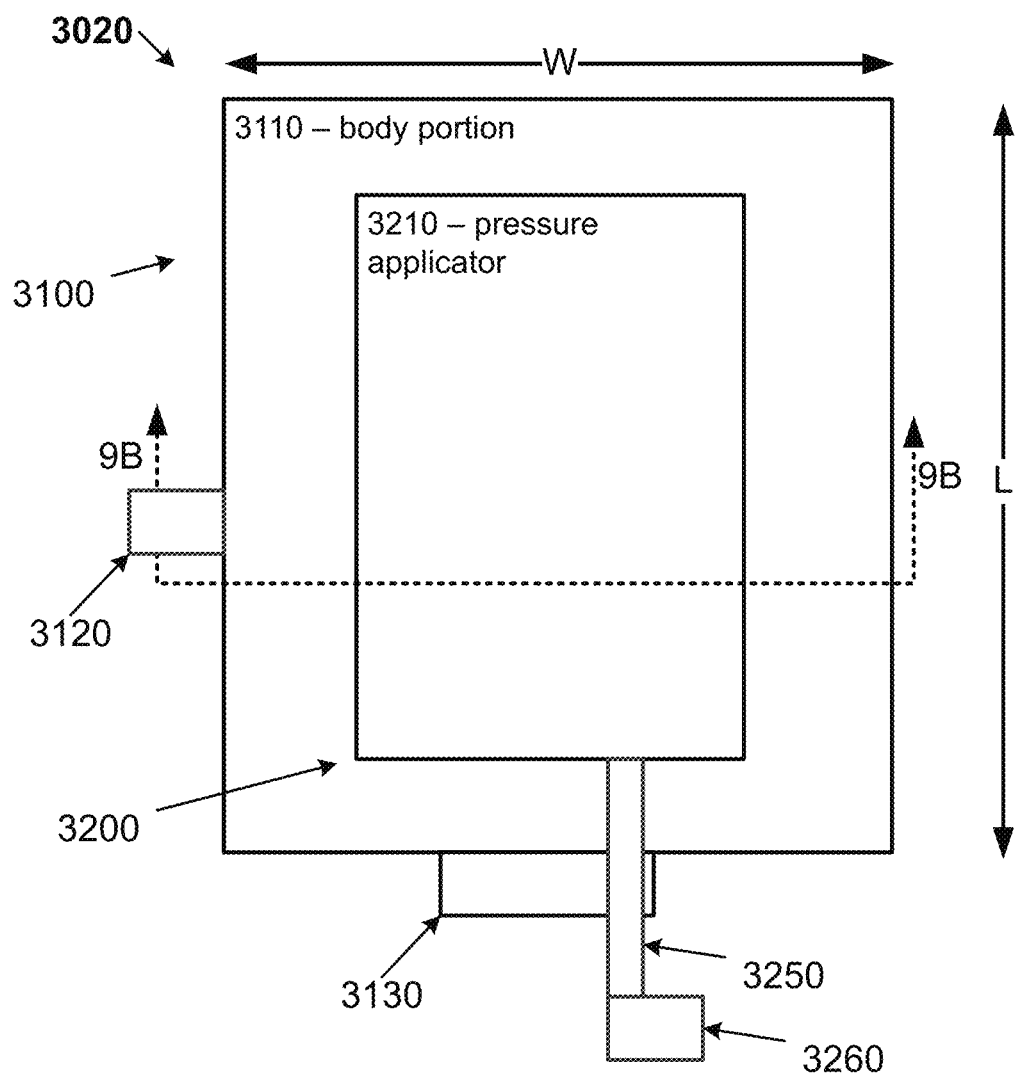
FIGS. 9A to 9G are schematic illustrations of a treatment delivery component, according to an embodiment.
Figure 9B:
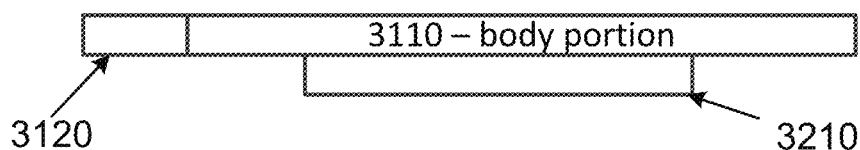

As discussed above, in some embodiments, each, any, or all of the other subsystems of treatment delivery component 1020 may be separate from outer shell 1100 and from each other, i.e., may be disposed in operative relationship with each other without coupling to each other, such as by stacking, nesting, etc. In other embodiments, each, any, or all of the other subsystems of treatment delivery component 1020 may be releasably couplable to outer shell 1100 and/or to each other. In still other embodiments, each, any, or all of the other subsystems of treatment delivery component 1020 may be fixedly coupled to outer shell 1100 and/or to each other. Some of these options are illustrated schematically for a treatment delivery component 3020 in FIGS. 9A to 9G. Treatment delivery component 3020 is shown in FIG. 9A in a plan view, and in FIG. 9B in a cross-section along line 9B-9B of FIG. 9A. In these figures, body portion 3110 of outer shell 3100 is shown, in an open configuration, e.g., laid out flat, with fastener portion 3120 unfastened. In these figures, pressure delivery component 3200 is shown with pressure applicator 3210 disposed on an inner surface (i.e., the surface that will face treatment portion TP of user body UB when treatment delivery component 3020 is in use) of body portion 3110, with pressure conduit 3250 extending from pressure applicator 3210, through passage 3130 of outer shell 3100, to pressure connector 3260. As described above, pressure applicator 3210 may be secured to body portion 3110 by any suitable technique, either fixedly or releasably, or may be disposed in operative relationship but not secured.

Figure 9C:
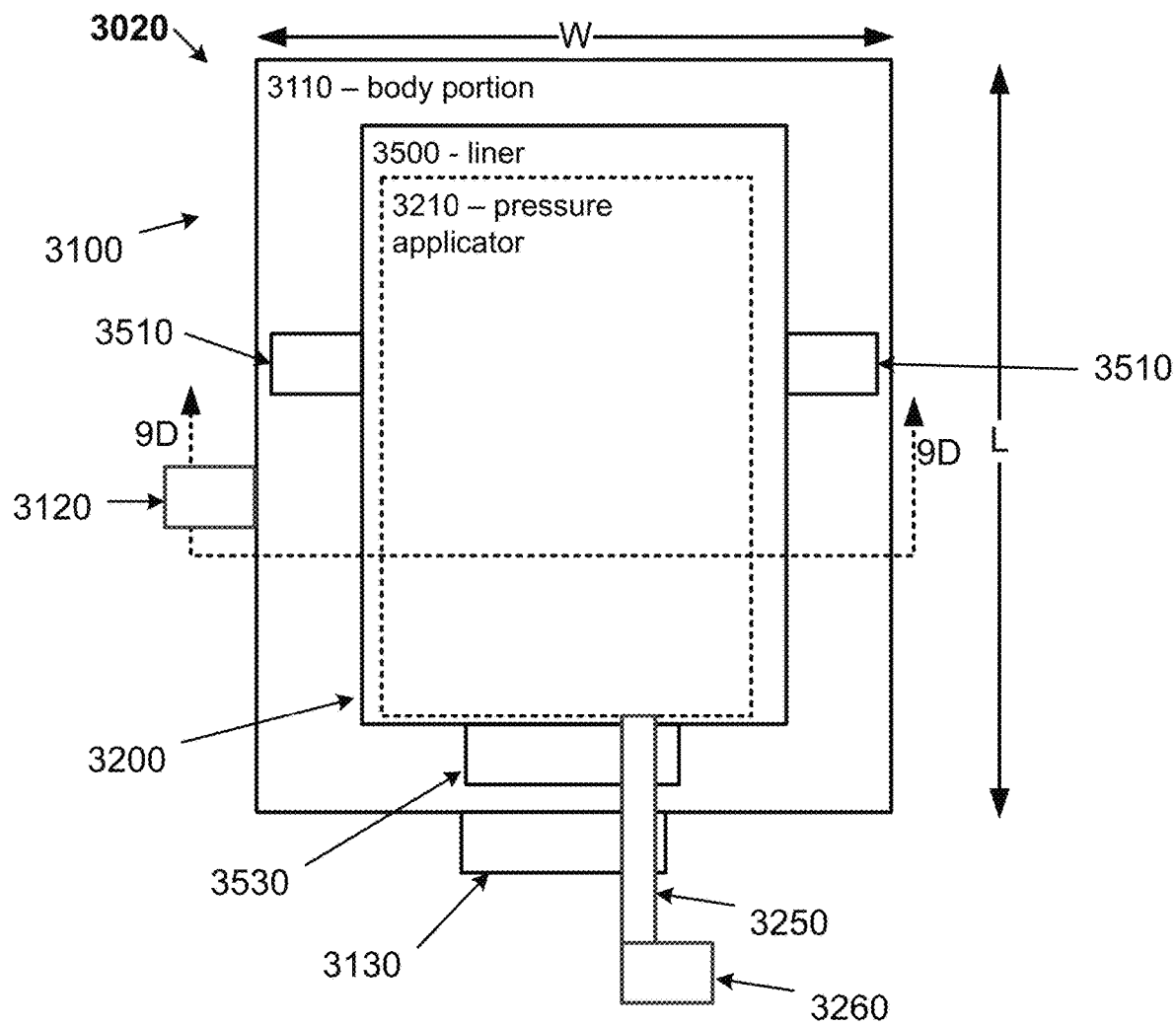
Figure 9D:
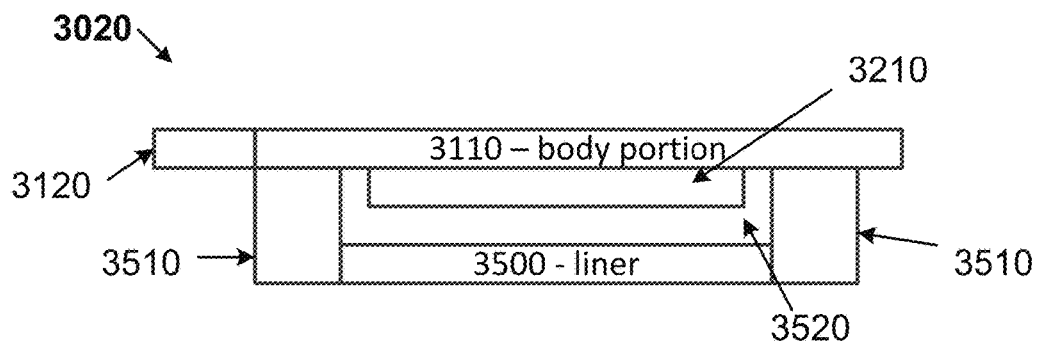

Treatment delivery component 3020 is further shown in FIG. 9C in a plan view, and in FIG. 9D in a cross-section along line 9D-9D of FIG. 9C. In these figures, liner 3500 is shown, added to the arrangement shown in FIGS. 9A and 9B. Liner 3500 is shown disposed on top of (i.e., closer to treatment portion TP when in use) pressure applicator 3210 and body portion 3110, and releasably secured to body portion 3110 by liner couplers 3510. Pressure conduit 3250 is shown extending through a liner opening 3530 of liner 3500—liner opening 3530 may be an aperture in liner 3500, or may be a space or gap between liner 3500 and body portion 3110. As shown in FIG. 9D, liner 3500 may be coupled to body portion 3110 to define a liner pocket 3520, e.g., a space, gap, or open volume between liner 3500, body portion 3110, and treatment applicator 3210. Liner 3500 may be coupled to body portion 3110 at discrete, discontinuous locations, i.e., liner couplers 3510 may be in the form of buttons, snaps, short segments of hook and loop fastener, etc. Alternatively, liner couplers 3510 may be continuous, e.g., zippers or elongated sections of hook and loop fastener, and may extend along the entire length and/or width of liner 3500. Correspondingly, liner pocket 3520 may be completely enclosed, e.g., by continuous fastening of liner 3500 around its entire periphery, in which configuration thermal applicator 3310 would be disposed on the surface of pressure applicator 3210 before liner 3500 is coupled thereto. In other embodiments, liner pocket 3520 may be open along one of its edges, e.g., a top edge, a bottom edge, or a side edge, such that thermal applicator 3310 can be slidably inserted through the open edge into liner pocket 3520.

Figure 9E:
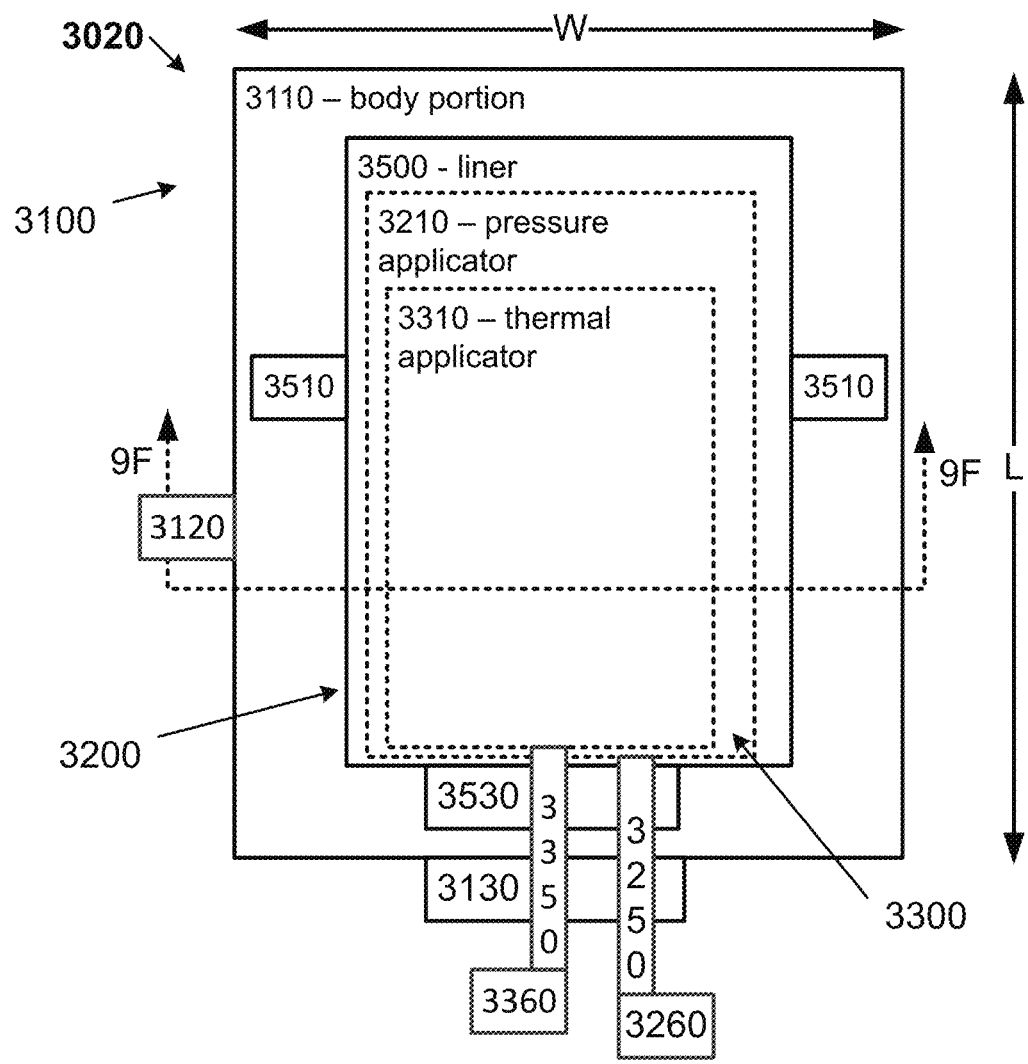
Figure 9F:
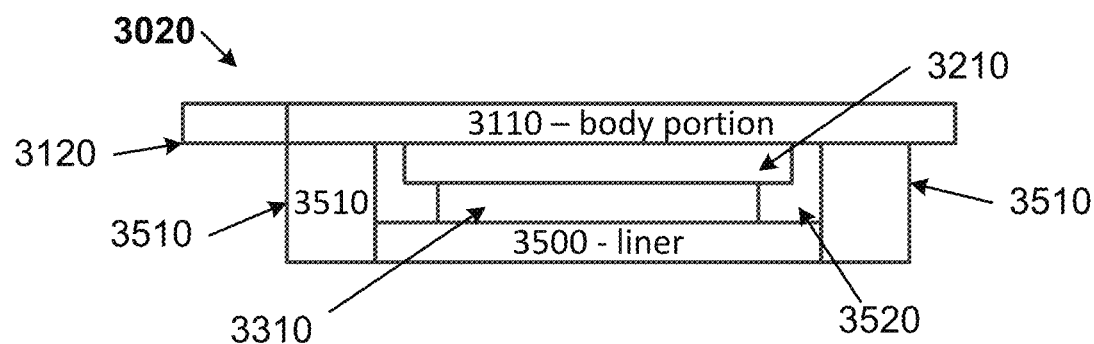

Treatment delivery component 3020 is further shown in FIG. 9E in a plan view, and in FIG. 9F in a cross-section along line 9F-9F of FIG. 9E. In these figures, thermal delivery component 3300 is shown, added to the arrangement shown in FIGS. 9C and 9D. Thermal delivery component 3300 is shown with thermal applicator 3310 disposed between pressure applicator 3210 and liner 3500, in liner pocket 3520, and with thermal conduit 3350 extending through liner opening 3530 and passage 3130 to thermal connector 3360. As described above, thermal applicator 3310 may be secured to any or all of the other components of treatment delivery component 3020 by any suitable technique, either fixedly or releasably, or may be disposed in operative relationship but not secured. For example, in this embodiment, thermal applicator 3310 may be captured or restrained in liner pocket 3520 (i.e., with limited, or no, range of movement laterally (in the width direction W) or longitudinally (in the length direction L), without the use of any mechanical fastener or other coupler to liner 3500, pressure applicator 3210, or body portion 3110. Thermal applicator 3310 may be retained in operative position through frictional engagement with liner 3500 and/or with the surface of pressure applicator 3210. Thermal applicator may be entirely covered by liner 3500, e.g., entirely contained within liner pocket 3520, or may have a portion extending out of liner pocket 3520.

As described above with reference to FIG. 8, in a method of treatment using a treatment delivery component, a user may configure the treatment delivery component 3020 for delivery of desired treatment modalities. Treatment delivery component 3020 can be configured for delivery of treatment in several ways. For example, a user may first dispose treatment delivery component 3020 in the arrangement shown in FIGS. 9A and 9B and, if pressure applicator 3210 is not already (e.g., fixedly) coupled to body portion 3110, the user may couple these components together and dispose pressure conduit 3250 through passage 3130. The user may then secure liner 3500 to body portion 3110 by liner connectors 3510 and dispose pressure conduit 3250 through liner opening 3530, resulting in the configuration shown in FIGS. 9C and 9D. The user may then dispose thermal delivery component 3300 in the arrangement shown in FIGS. 9E and 9F, such as by introducing pressure connector 3360 and pressure conduit 3350 into liner pocket 3520 from the upper (top in FIG. 9E) end of liner pocket 3520, then feeding pressure connector 3360 and pressure conduit 3350 through liner pocket 3520 and through liner opening 3530 and passage 3130, while introducing thermal applicator 3310 into the upper end of liner pocket 3520 and finally moving thermal delivery component 3300 into the position shown in FIG. 9E. Alternatively, a user may configure treatment delivery component 3020 by the same process described above, but by disposing thermal delivery component 3300 in the position shown in FIG. 9E, and then securing liner 3500 to body portion 3110 by liner connectors 3510, overlying thermal applicator 3310.

Many other variations are also contemplated for configuration of treatment delivery component 3020. For example, thermal applicator 3310 may be releasably secured to pressure applicator 3210 (such as by hook and loop fasteners), and liner 3500 may subsequently be secured to body portion 3110, overlying thermal applicator 3310. Thermal applicator 3310 may be maintained in position laterally and/or longitudinally by the releasable coupling to pressure applicator 3210, and simply covered by liner 3500 (rather than relying on liner 3500 to define boundaries for liner pocket 3520 that retain pressure applicator 3310 in position).

Figure 9G:
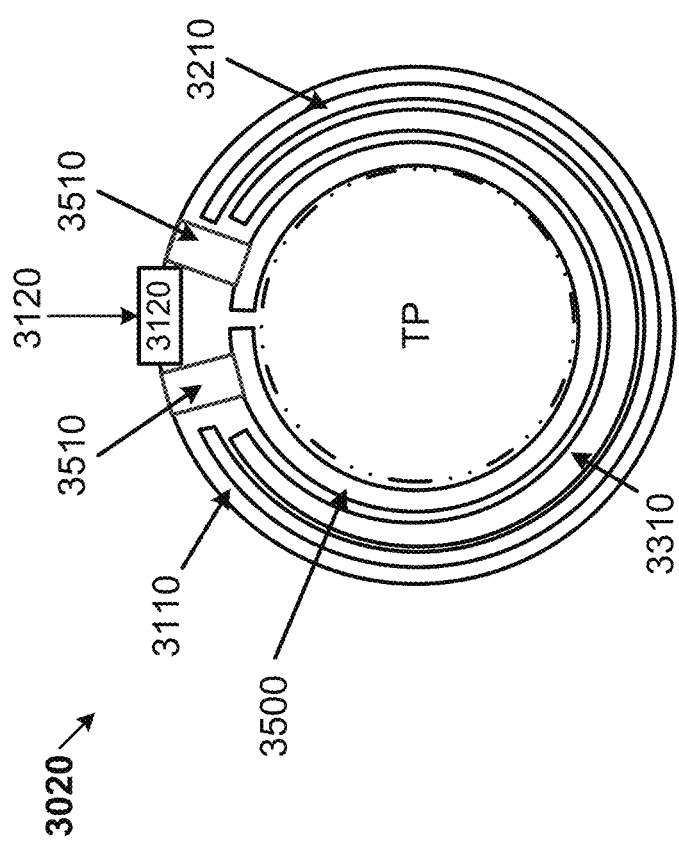

After treatment delivery component 3020 has been configured, it may be secured to treatment portion TP of user body UB, as described above with reference to FIG. 8 at 2100. Treatment delivery component 3020 is shown secured to treatment portion TP in FIG. 9G, in a closed configuration. As shown in FIG. 9G, treatment delivery component 3020 is disposed with liner 3500 adjacent the surface of treatment portion TP (e.g., in contact with the user's skin, or overlying clothing disposed on treatment portion TP). Body portion 3110 is coupled in place around treatment portion TP by connecting its lateral edges (in the width direction W shown in FIG. 9E) with fastener portion 3120. The remainder of treatment method 2000 described above with reference to FIG. 8 may then be performed.

Although shown in FIGS. 9A to 9G as including a thermal delivery component 3300, treatment delivery component 3020 may include an other delivery component instead of, or in addition to, thermal delivery component 3300, as described above with reference to treatment delivery component 1020 and treatment system 1000. And although shown as including a pressure delivery component 3200, treatment delivery component 3020 may not have a pressure delivery component, and may instead have only thermal delivery component 3300, or an other delivery component, as also describe above with reference to treatment delivery component 1020 and treatment system 1000.

As described above with reference to treatment system 1000, pressure delivery component 1200 may be operated to provide either or both of two functions: a) it may be operated to selectively deliver pressure treatment or therapy to the treatment portion TP of user body UB; and/or b) it may be operated to interface with an outer shell 1100 and one or both of thermal delivery component 1300 and other treatment delivery component 1400 to enhance the effectiveness of those components. As shown and described above, the effectiveness of thermal delivery component 1300 and/or other treatment delivery component 1400 can be enhanced by applying pressure from pressure delivery component 1200 to establish and maintain good apposition of thermal applicator 1310 and/or other treatment applicator 1410 with the surface of treatment portion TP of user body UB (e.g., the user's skin). Another way in which pressure delivery component 1200 can enhance the effectiveness of thermal delivery component 1300 and/or other treatment delivery component 1400, and of treatment delivery system 1000 overall, is to adapt the treatment applicators to the dimensions of the treatment portion TP of user body UB for different users of different sizes, and/or for different treatment portions of the same user. In this way, a single size of treatment delivery component 1020 can be used to deliver treatment to, for example, the leg of a small female user and the leg of a large male user. This capability can be commercially desirable because only one size or model of treatment delivery component is required to be manufactured, distributed, stored, maintained, etc. to be used with control units 1040 for treatment of a wide range of users. This size adapting capability can also be provided at least in part by one or more components separate from pressure delivery component 1200, e.g., components that do not play a role in the delivery of pressure therapy, as described in more detail below in connection with some embodiments. This size adapting functionality is illustrated schematically for one embodiment in FIGS. 10A to 10F for a treatment delivery component 4020.

Treatment delivery component 4020 is shown in FIGS. 10A to 10F, for ease of illustration, only with body portion 4110 and fastener portion of outer shell 4100, with pressure applicator 4210, and with thermal applicator 4310. However, treatment delivery component 4020 can include all of the elements described above for treatment delivery components 1020 and 3020.

Figure 10A:
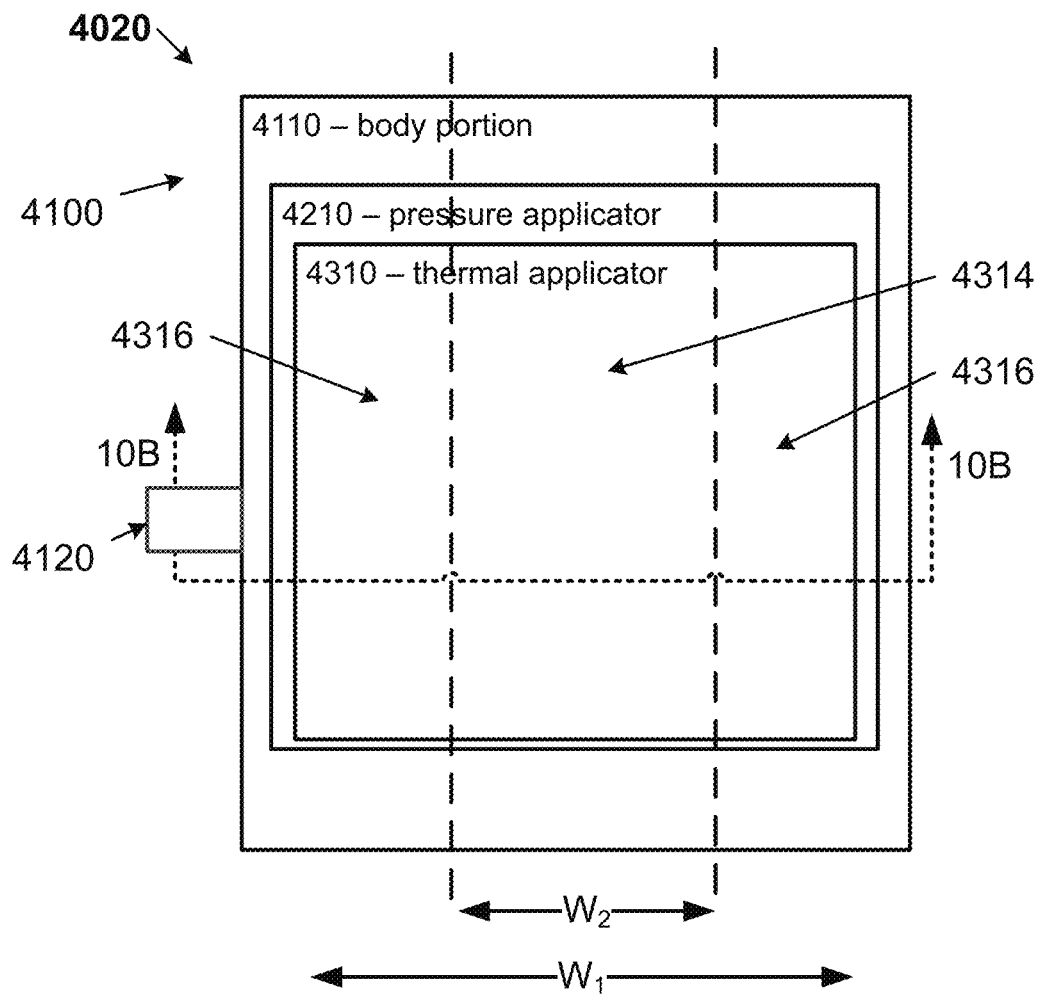
FIGS. 10A to 10F are schematic illustrations of a treatment delivery component, according to another embodiment.
Figure 10B:
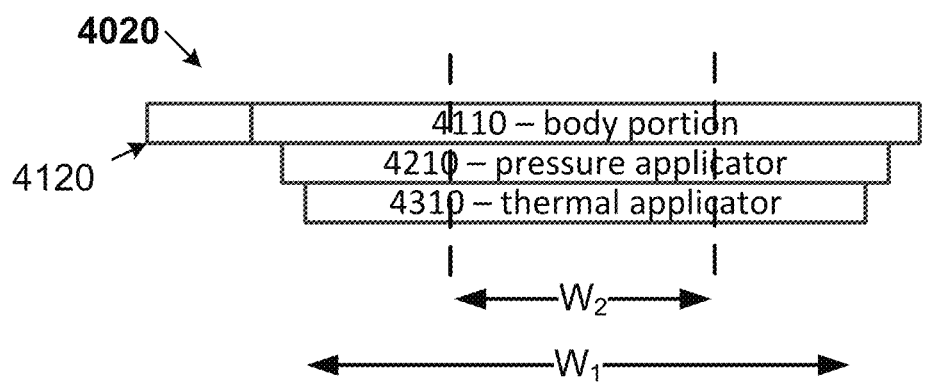
Figure 10C:
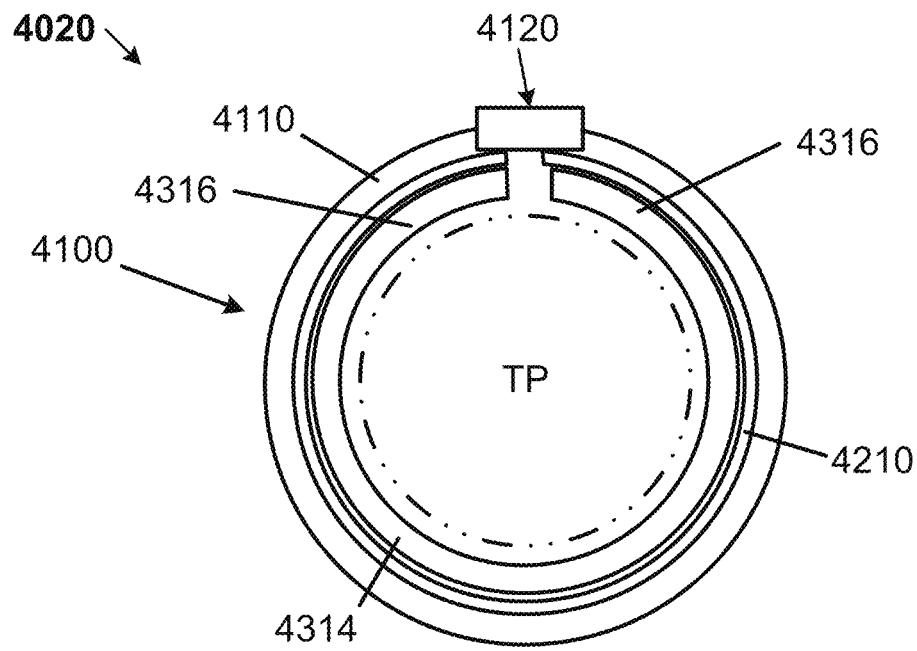
Figure 10D:
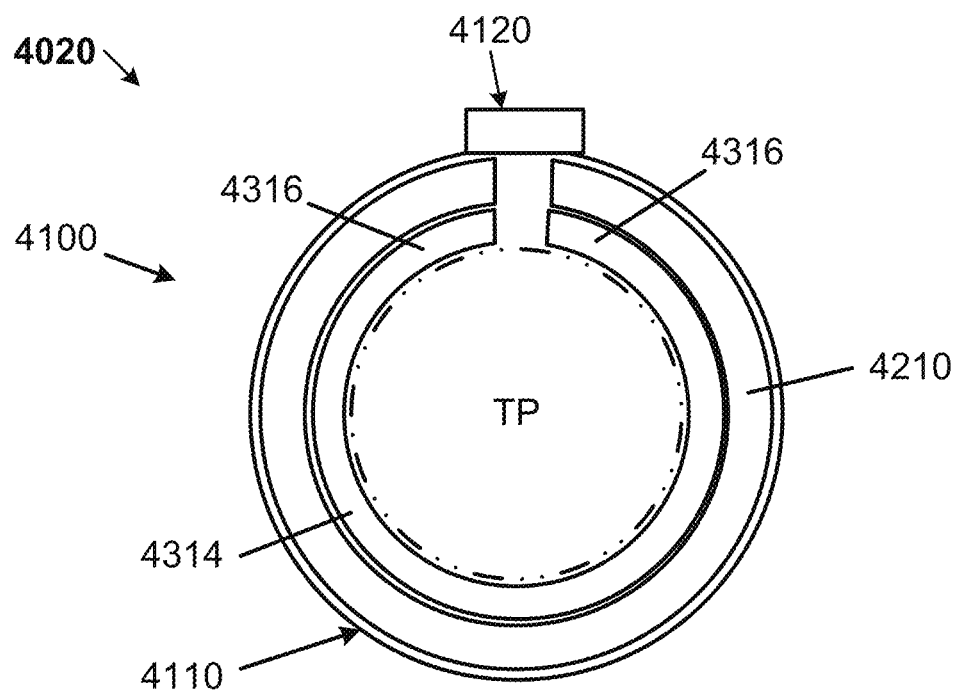

As shown in FIGS. 10A and 10B, thermal applicator has a central portion 4314 and side portions 4316, which for ease of reference are shown as separated by the dashed lines in FIGS. 10A and 10B. The width of central portion 4314 is indicated by $W_2$, and the overall width of thermal applicator 4310 (including central portion 4314 and both side portions 4316) is indicated by $W_1$. Width $W_1$ can correspond to the circumference (or other lateral extent, e.g., for a treatment portion that is not enclosable by the treatment delivery component) of the largest treatment portion TP to which thermal applicator 4310 can be applied and provide thermal treatment to the entire circumferential (or other) extent of treatment portion TP. $W_2$ can correspond to the circumference (or other extent) of the smallest treatment portion TP to which thermal applicator 4310 can be applied while being capable of providing effective thermal treatment to treatment portion TP. FIGS. 10C and 10D schematically illustrate treatment delivery component 4020 secured to a treatment portion TP having a circumference corresponding to $W_1$ (the gap between the edges of thermal applicator 4310 is shown for easy of illustration). Pressure applicator 4210 is shown in an unpressurized configuration and a pressurized configuration, respectively, in FIGS. 10C and 10D.

Figure 10E:
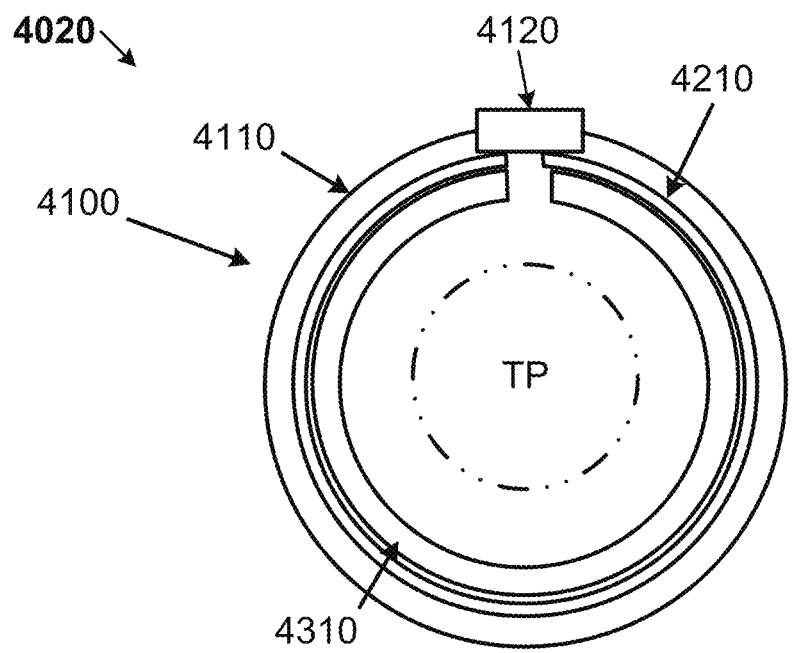
Figure 10F:
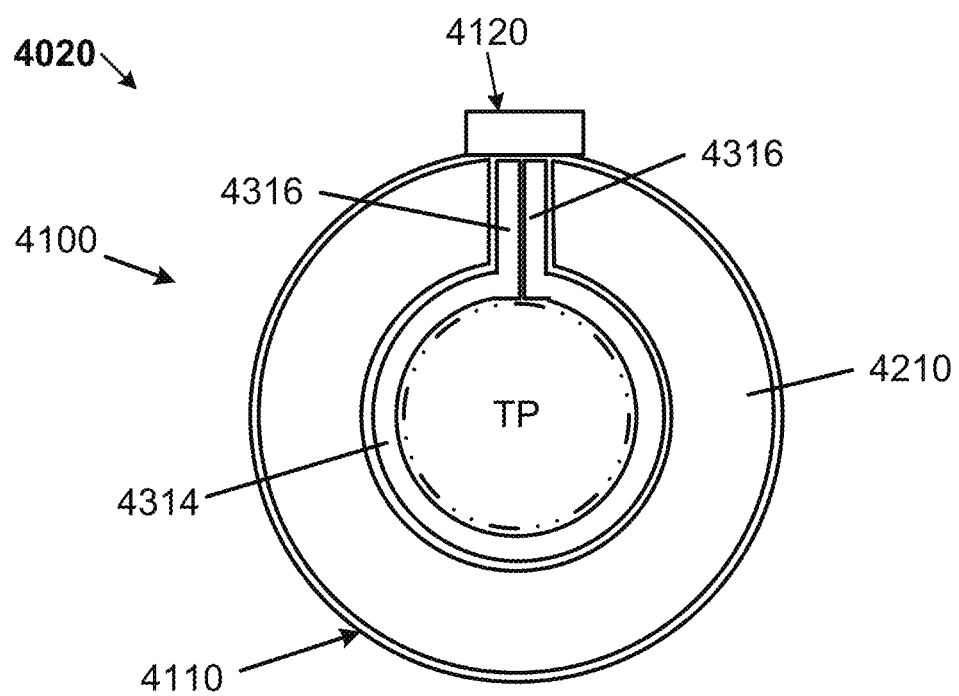

Treatment delivery component 4020 is schematically illustrated in FIGS. 10E and 10F secured to a treatment portion TP having a circumference corresponding to $W_2$. Although not shown in FIGS. 10E and 10F, the edges of thermal applicator 4310 are maintained in an approximately fixed, and relatively closely spaced, relationship with the edges of body portion 4110. Thus, as shown in FIG. 10E, when pressure applicator 4210 is in an unpressurized configuration, thermal applicator 4310 is substantially spaced from the surface of (relatively small) treatment portion TP, and thus not in good thermal apposition to permit effective delivery of thermal treatment. However, when pressure applicator 4210 is in a pressurized configuration, as shown in FIG. 10F, pressure applicator 4210 urges thermal applicator into a configuration in which central portion 4314 is in good apposition with the full circumference of treatment portion TP, while side portions 4316 are approximated or urged together (or towards each other, if there is other structure, such as liner 4500, between them), and extend radially approximately from the outer surface of treatment portion TP to their connections to the edges of body portion 4110. Thus, side portions 4316 face each other, i.e., the inner surfaces of side portions 4316 (which would otherwise be engaged with, or facing, treatment portion TP) are adjacent or in contact, and do not overlap each other (i.e. the inside surface of one side portion 4316 does not face the outside surface of the other side portion 4316). The side portions 4316 may be considered to be "wasted," in that they are not in apposition with the surface of treatment portion TP, and thus cannot deliver thermal treatment thereto. However, central portion 4314 is in good apposition with treatment portion TP and can deliver thermal treatment thereto. This "wasting" effect is a desirable capability of treatment delivery component 4020, enabling it to be secured to and effectively treat a wide range of sizes of treatment portions TP. The division of thermal applicator 4310 into central portion 4314 and side portions 4316 is arbitrary, in that central portion 4314 can just be considered to be the portion that can be disposed in good apposition with the surface of whatever size treatment portion TP thermal applicator 4310 has been secured to, and side portions 4316 can just be considered to be the portions of thermal application 4310 that are "wasted" by being urged together, and not in contact with treatment portion TP. Although the benefits of wasting thermal applicator 4310, having the inner surfaces of side portions 4316 face each other, is described here in the context of thermal treatment, the approach and benefits are also applicable to other treatment modalities, and thus can be used for an other treatment applicator, including an electrical treatment applicator. Such other treatment applicator may also have a center portions and side portions, and the inner surfaces of the side portions approximated, as described above for the thermal applicator 4310.

The arrangement of the elements of treatment delivery component 4020 described above have several advantages and benefits. Some known approaches to adapting thermal or pressure treatment devices to different sizes of users or their treatment portions involve wrapping the devices around the treatment portions, so that a portion of the inner surface (the surface intended to face the treatment portion in use) of the device(s) overlaps the outer surface of the device(s), as in a partial spiral. Such devices may be secured in this overlapping arrangement or configuration by releasable coupling mechanisms such as hook and loop fasteners. Such systems rely on the user to wrap the system on the treatment portion to a suitable degree of tightness (not too tight, not too loose). In contrast, in embodiments disclosed herein, the treatment delivery component 4020, the pressure, thermal, or other treatment delivery components are not overlapped when applied to a smaller user or treatment portion TP. Rather, treatment delivery component 4020 is secured around treatment portion TP in an edge-to-edge arrangement, such as by having body portion 4110 of outer shell 4100 secured at its edges by fastener portion 4120. With this arrangement, neither pressure applicator 4210 nor thermal applicator 4310 overlaps with itself when disposed around a relatively smaller treatment portion TP. Rather, as shown in FIG. 10F, the inner surface of thermal applicator 4310 is either in apposition with treatment portion TP (for central portion 4314) or faces itself (for side portions 4316). Also, advantageously, the user is not relied upon to properly fit treatment delivery component 4020 to treatment portion TP as with previous known approaches. Rather, the user need only dispose treatment portion TP in treatment delivery component 4020 and fasten body portion 4110 of outer shell 4100 by fastener portion 4120, and the expansion of pressure elements 4212 automatically adapts treatment delivery component 4020 to the size of treatment portion TP.

Figure 11A:
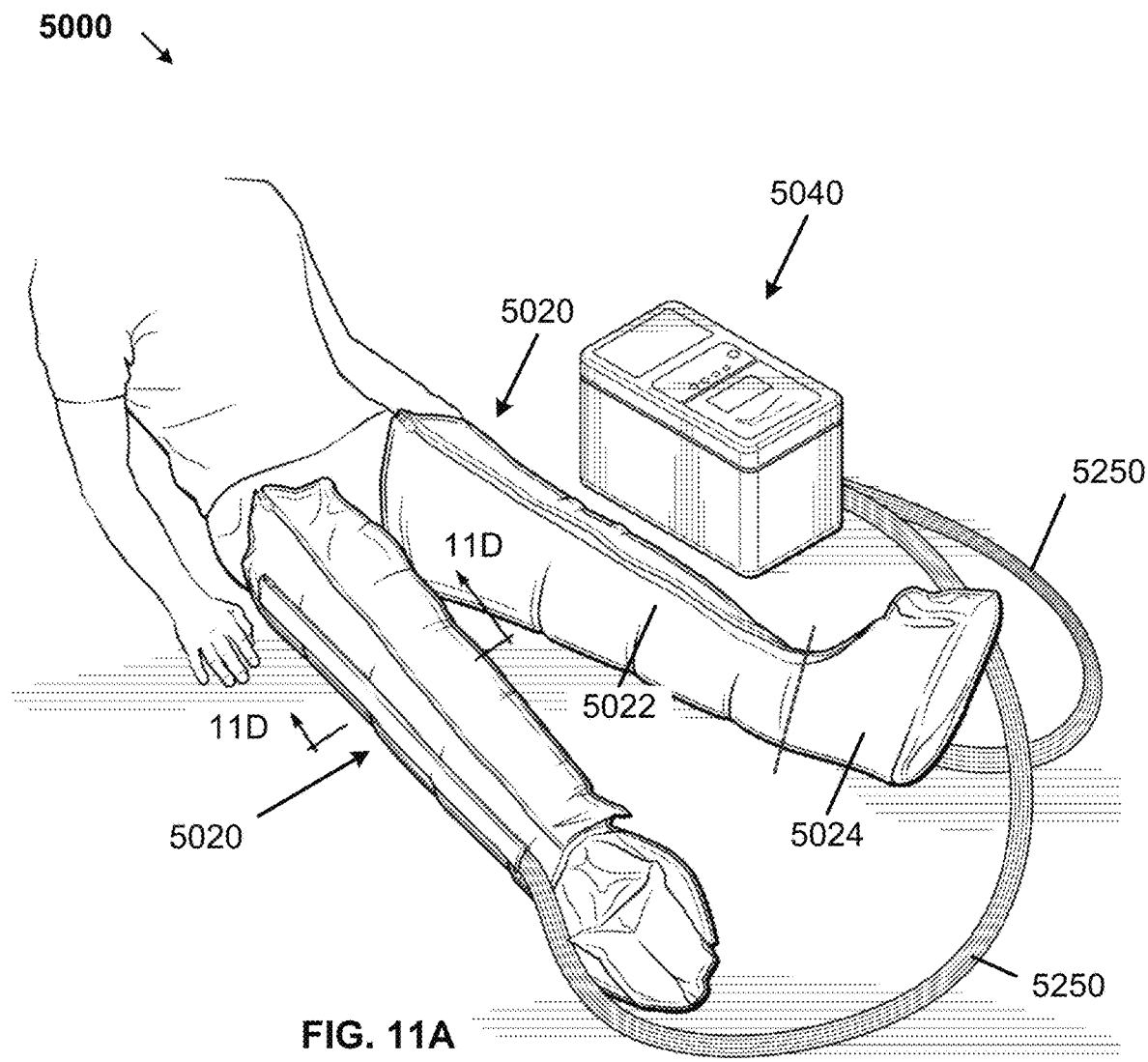
FIGS. 11A to 11T are illustrations of a treatment system, according to an embodiment.
Figure 11B:
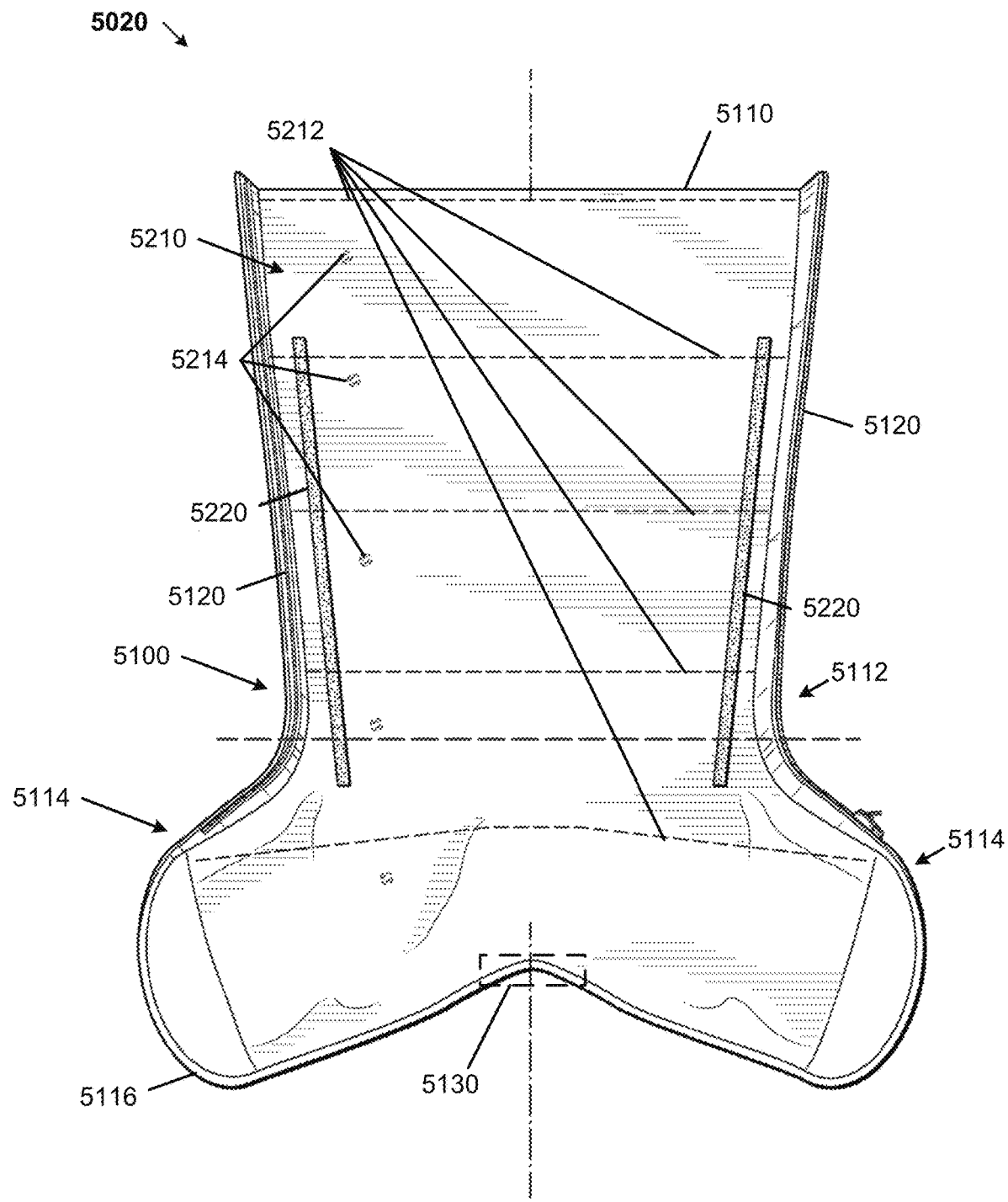
Figure 11C:
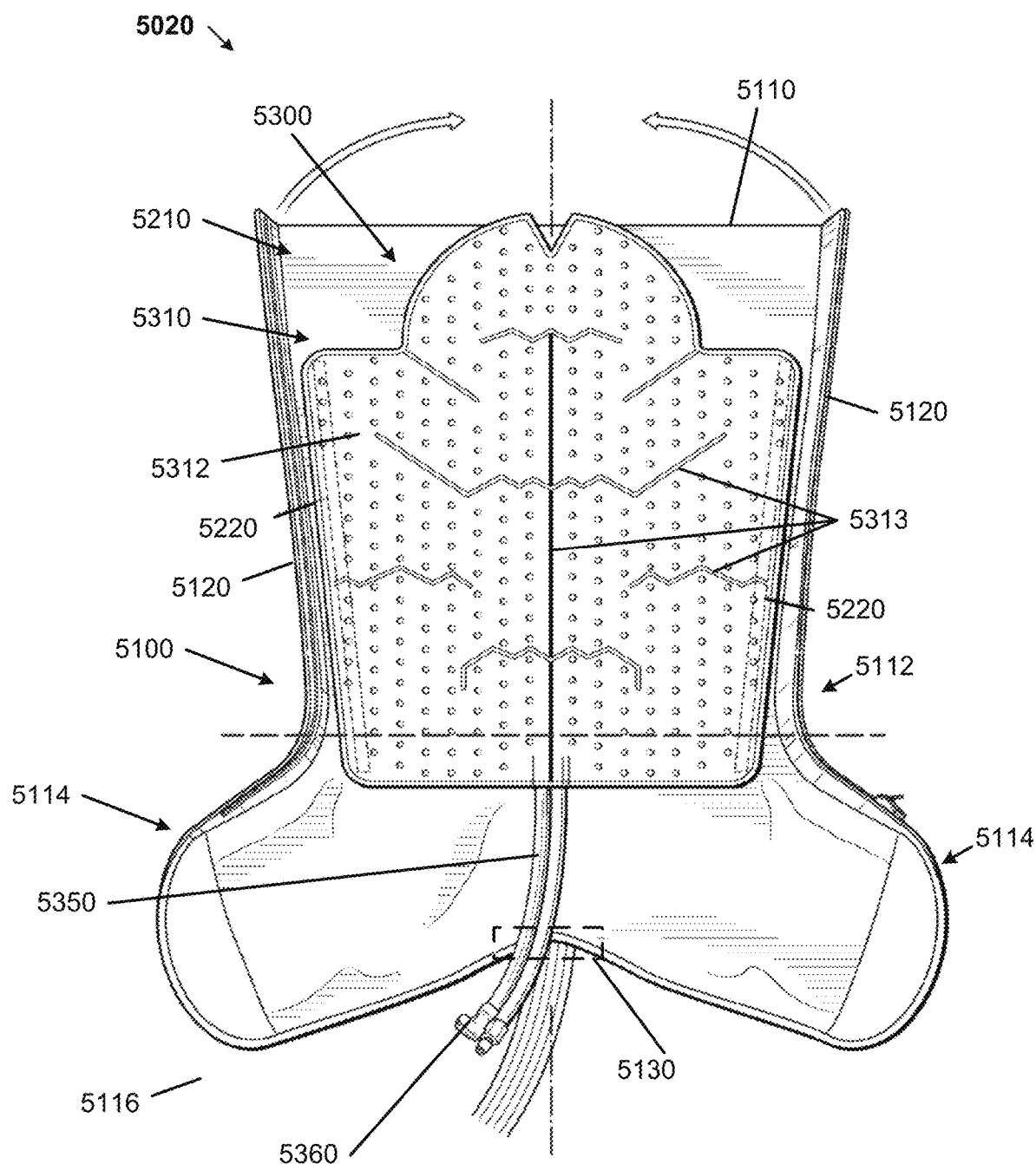
Figure 11D:
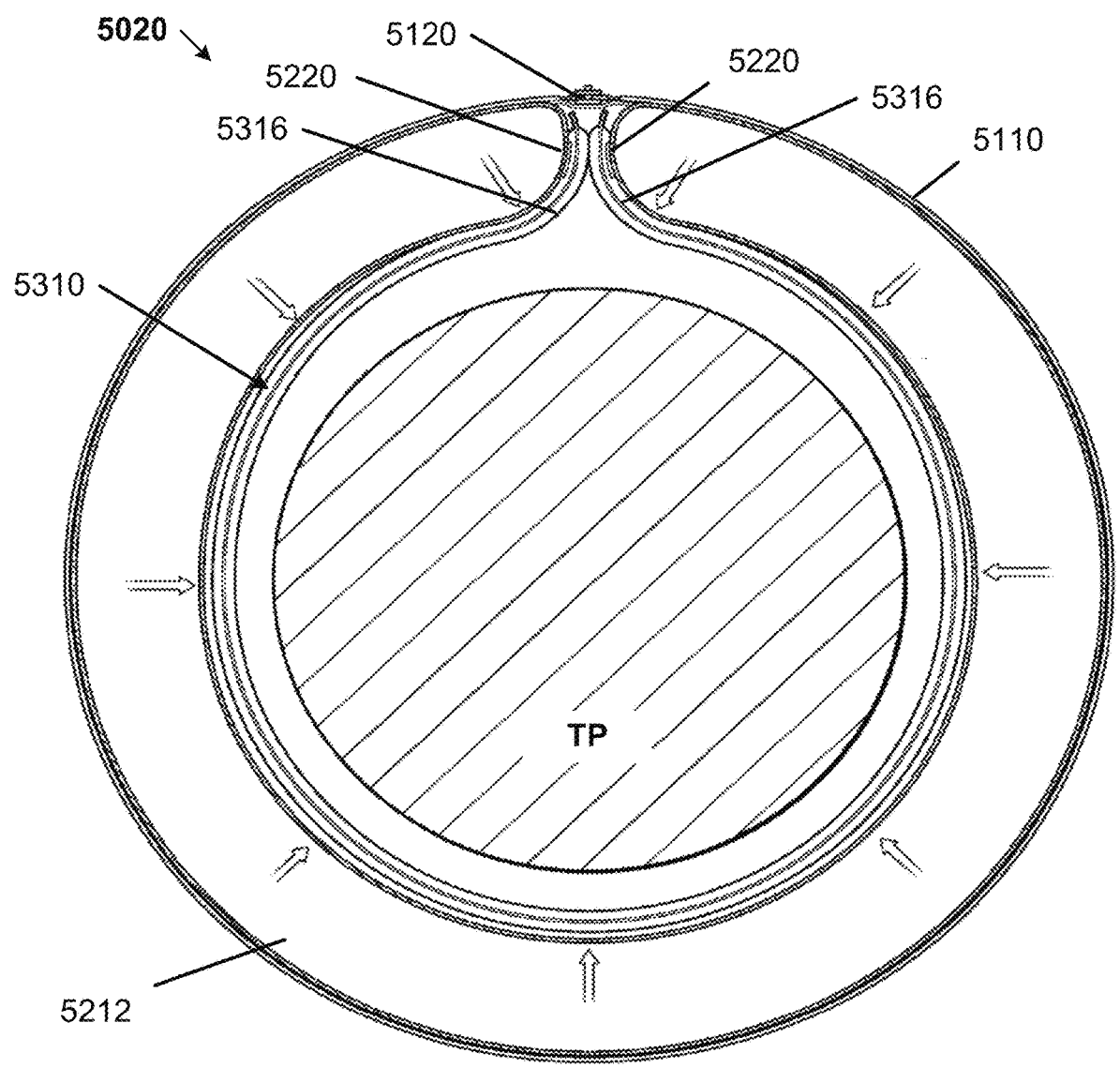
Figure 11E:
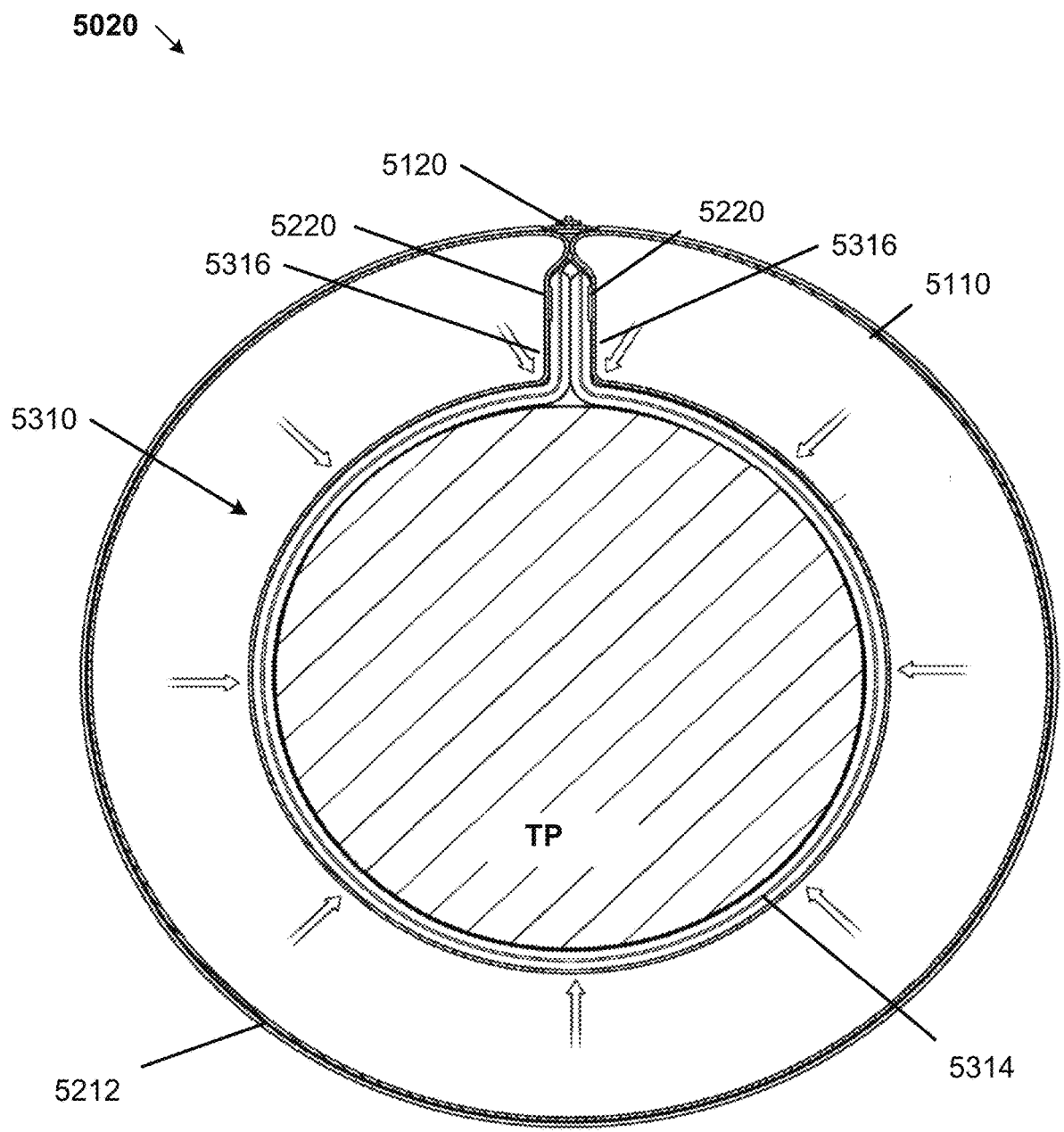
Figure 11F:
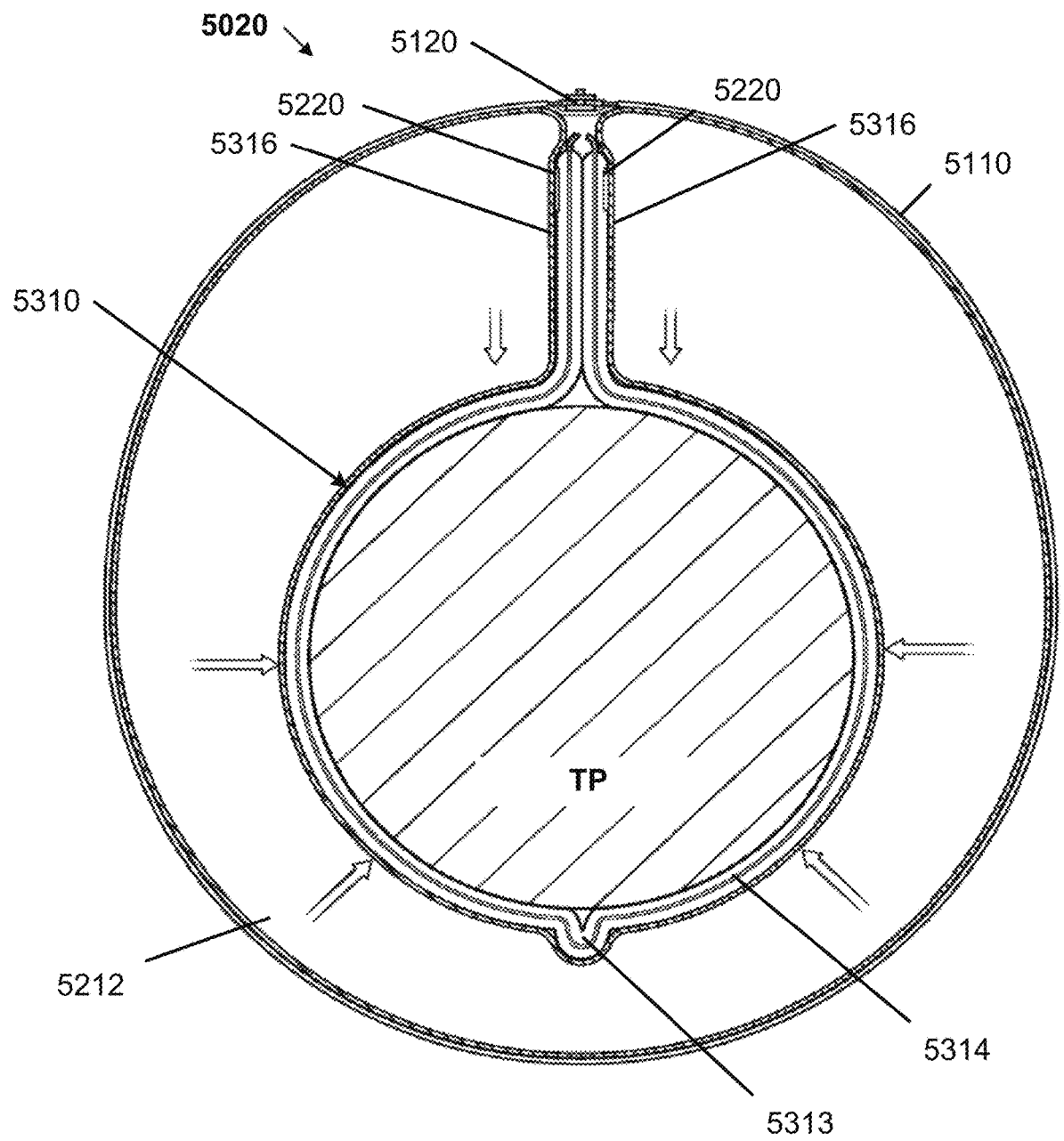
Figure 11G:
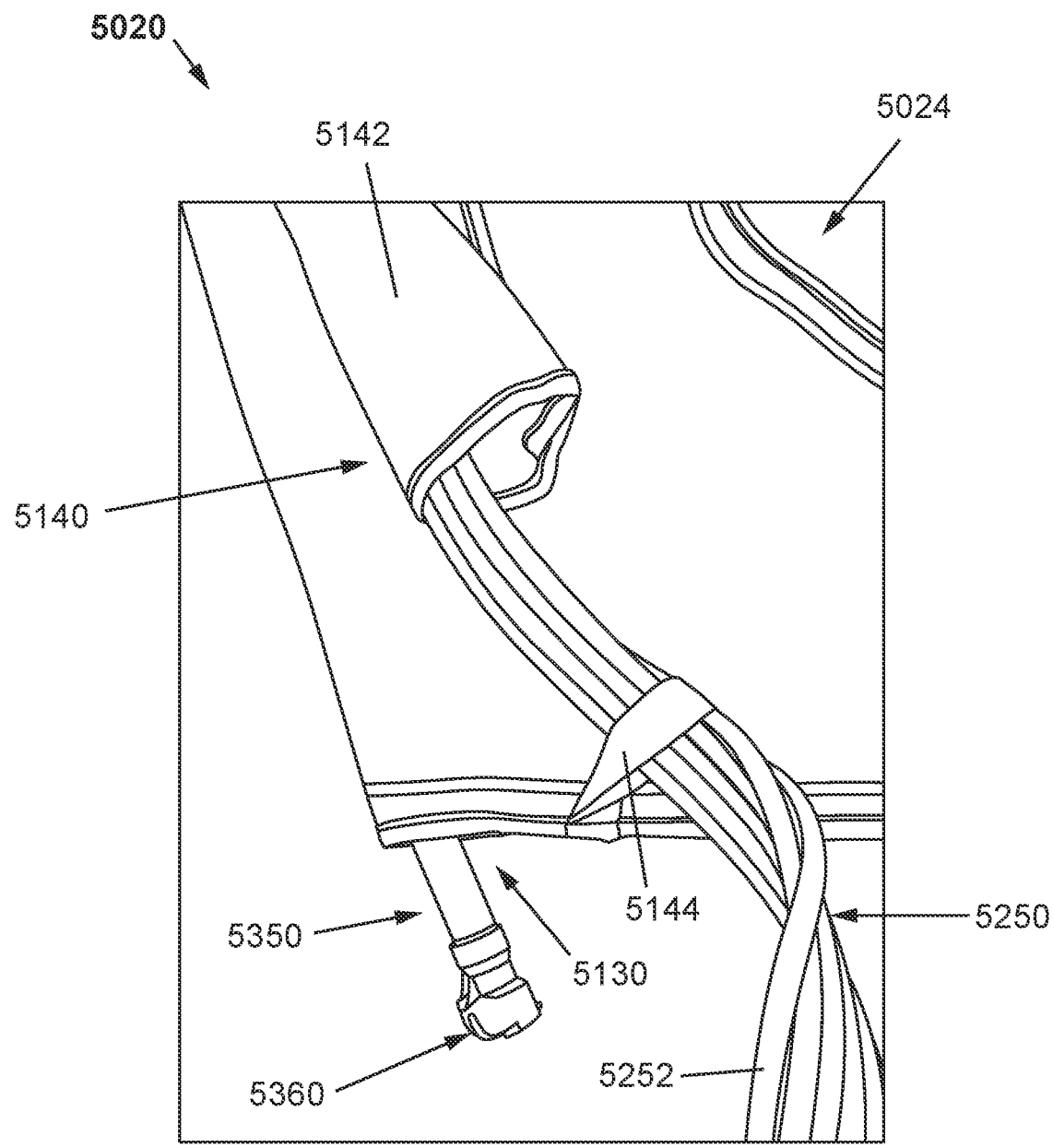
Figure 11H:
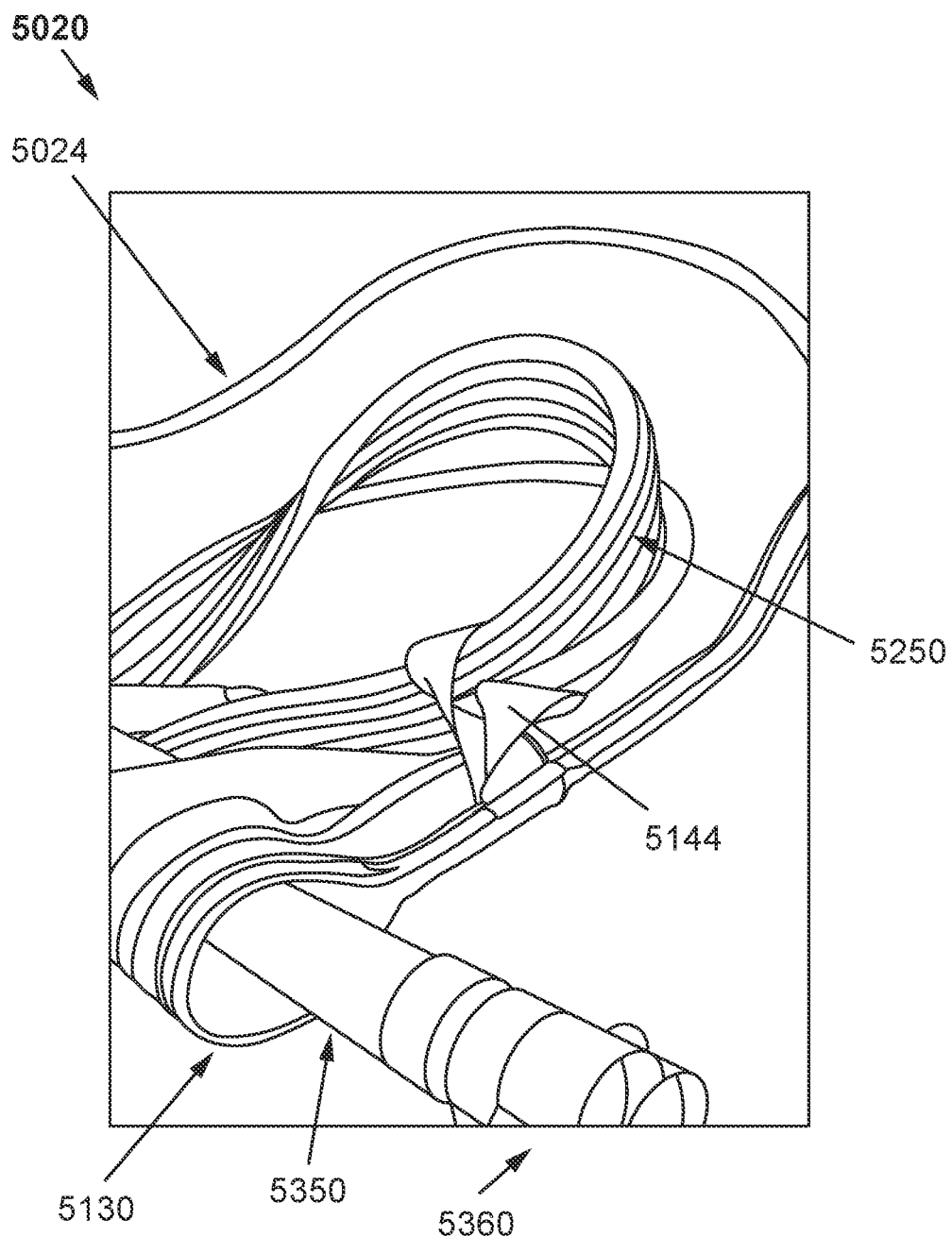
Figure 11I:
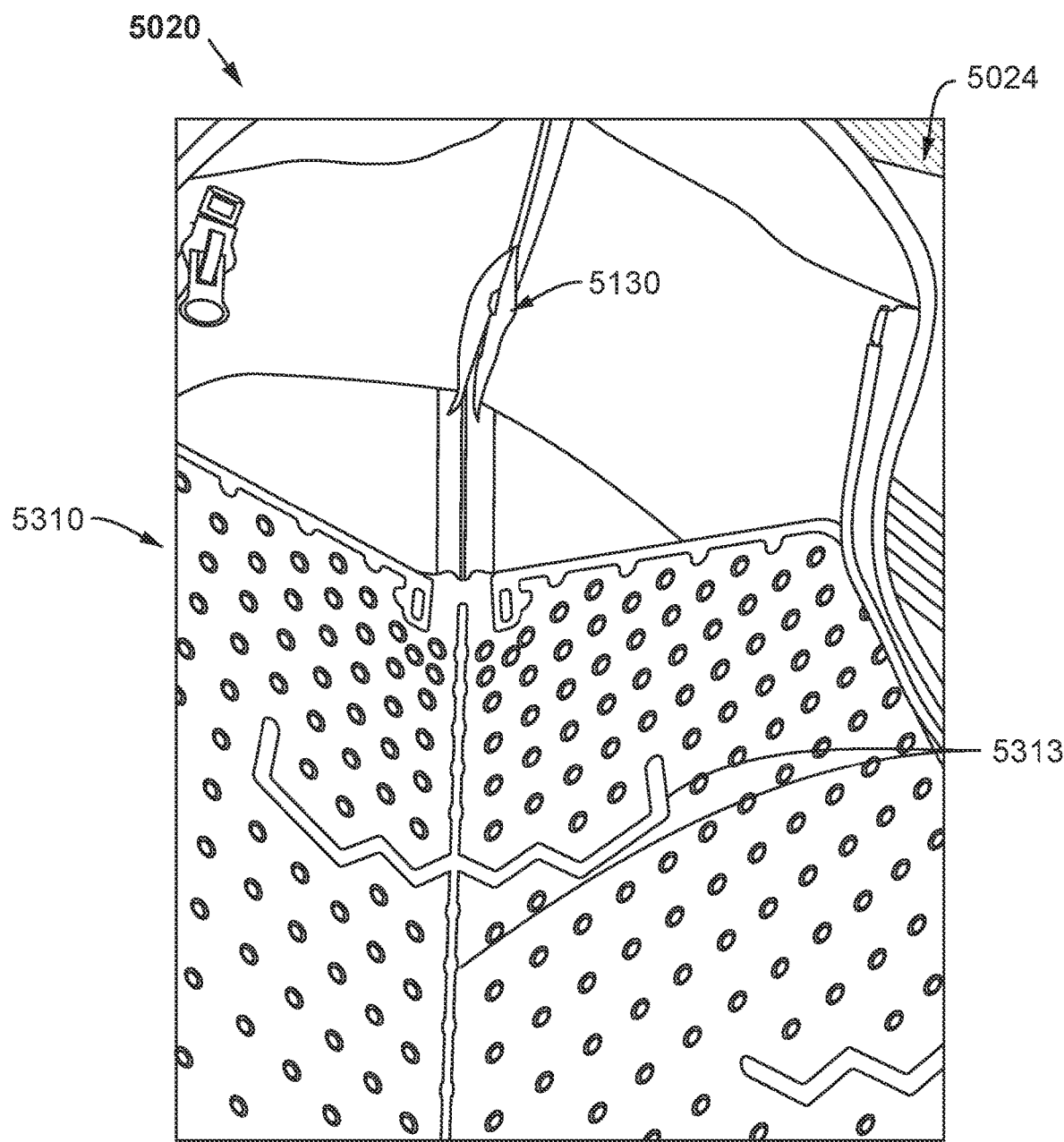
Figure 11J:
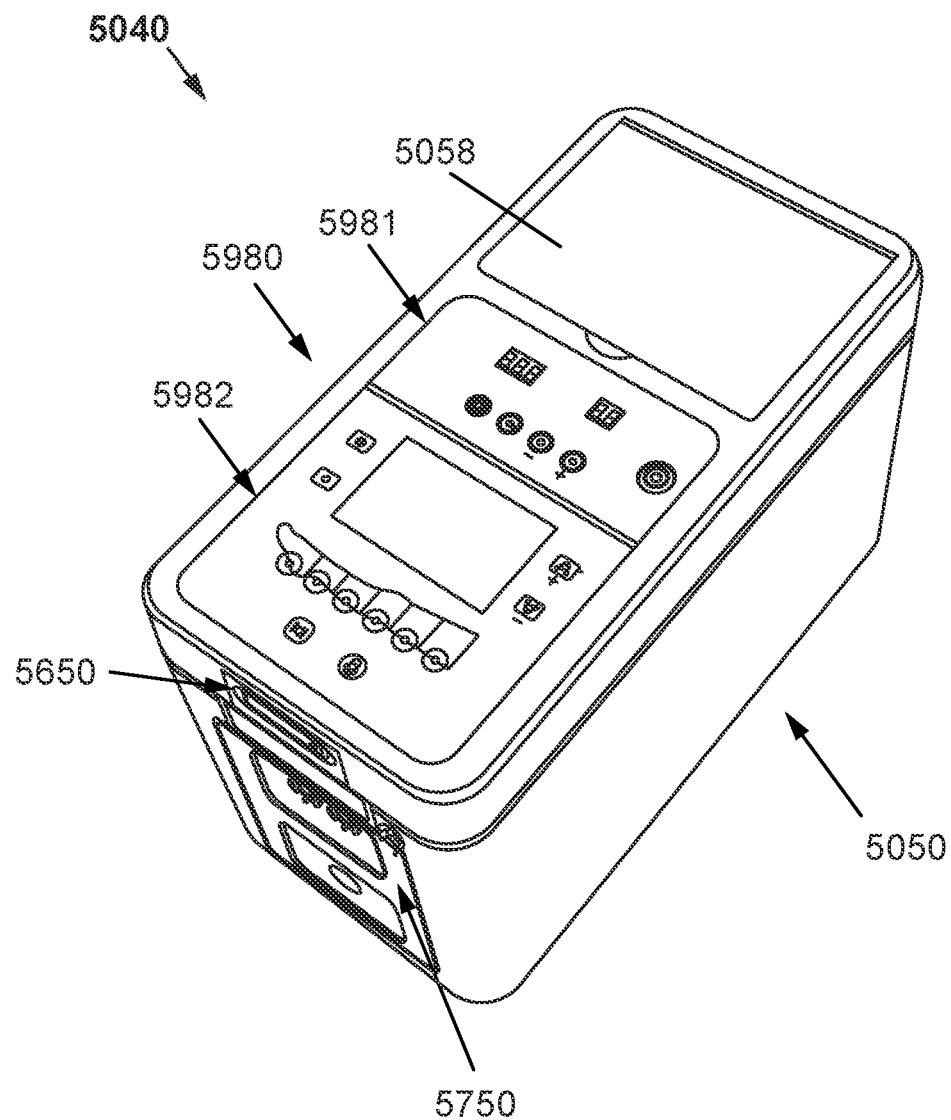
Figure 11K:
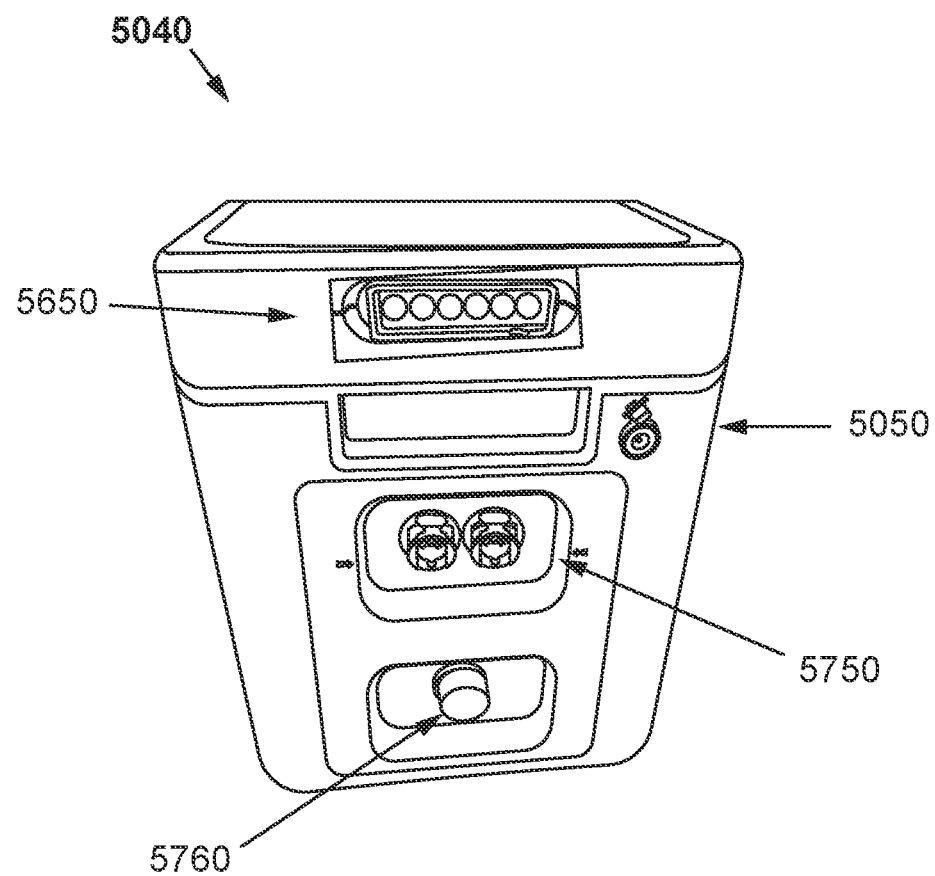
Figure 11L:
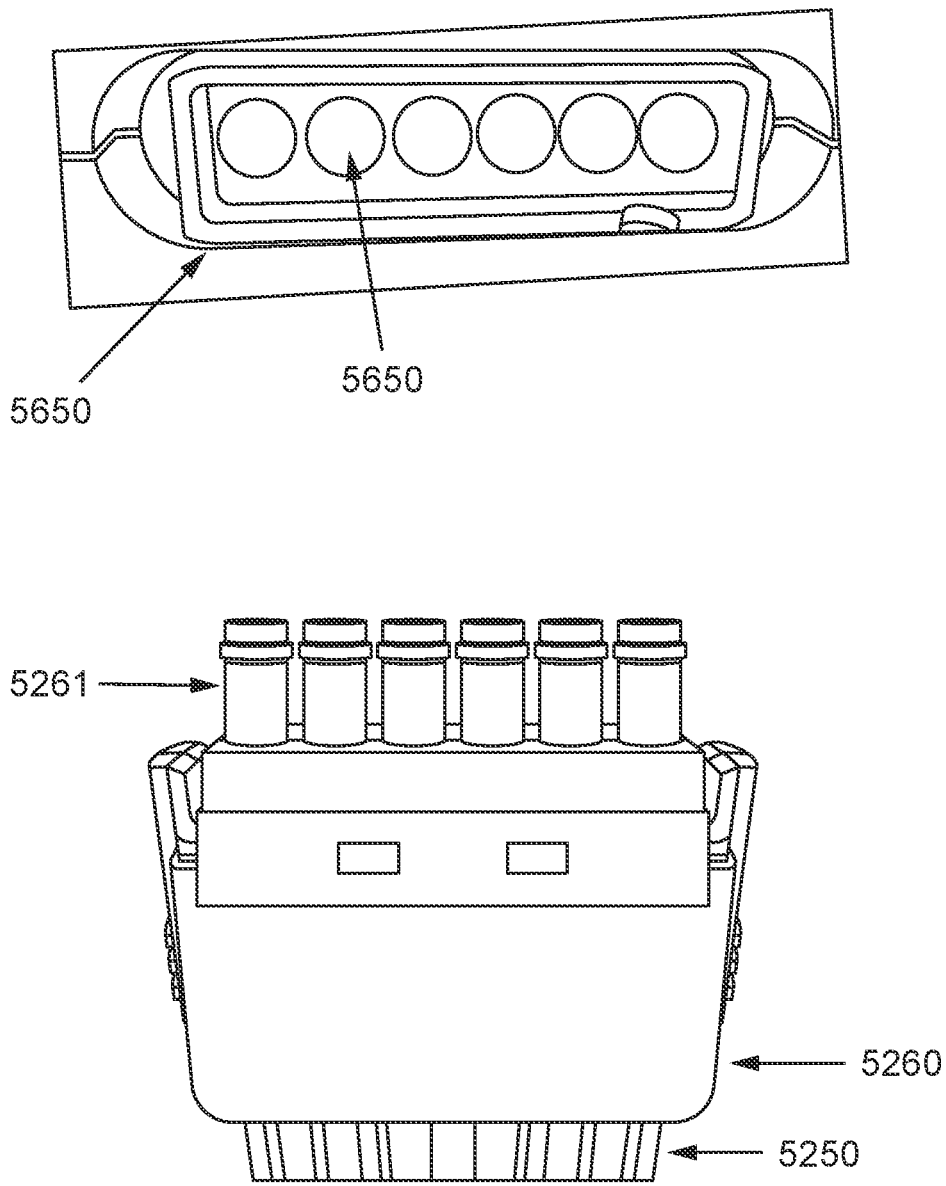
Figure 11M:
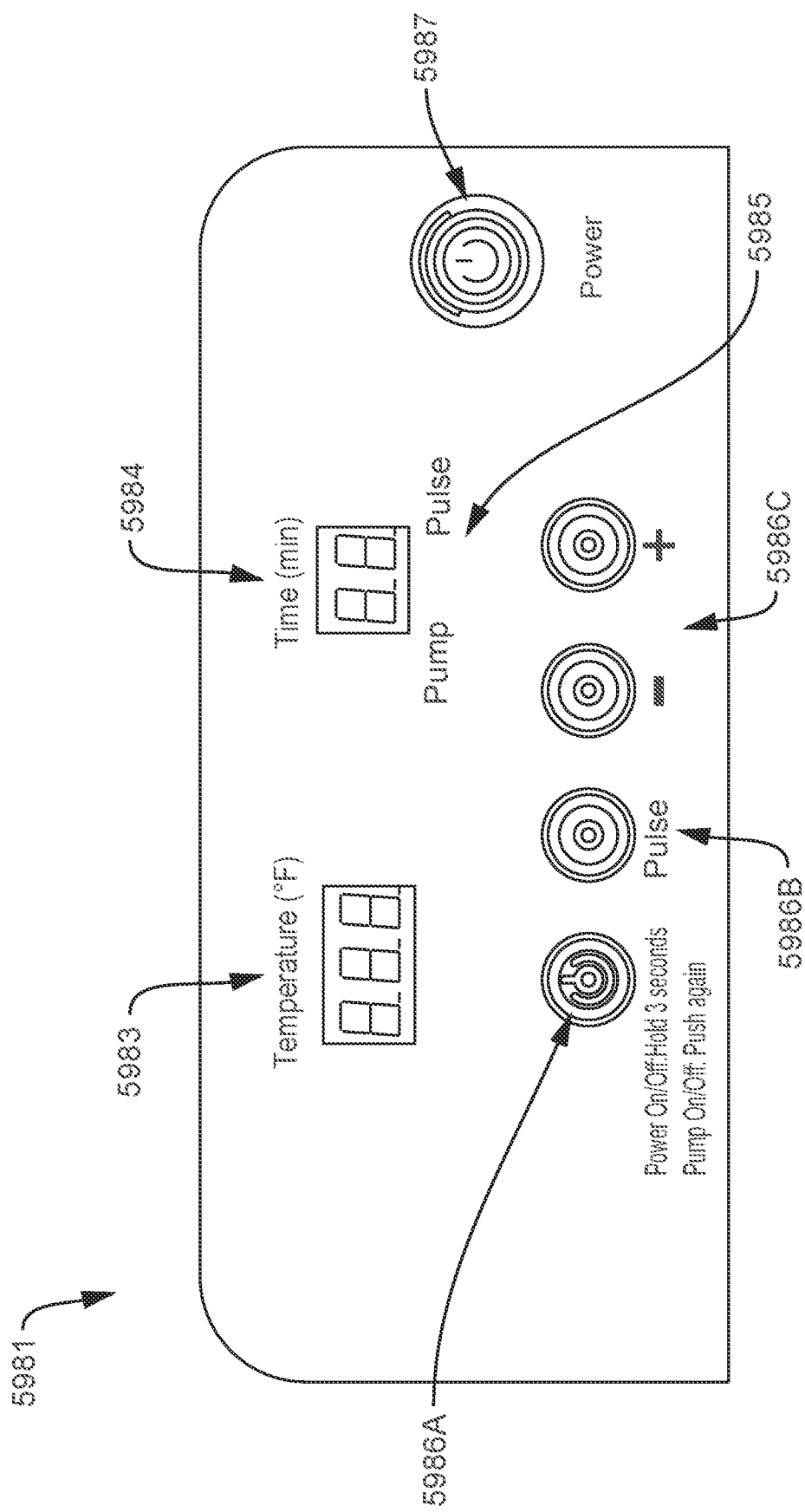
Figure 11N:
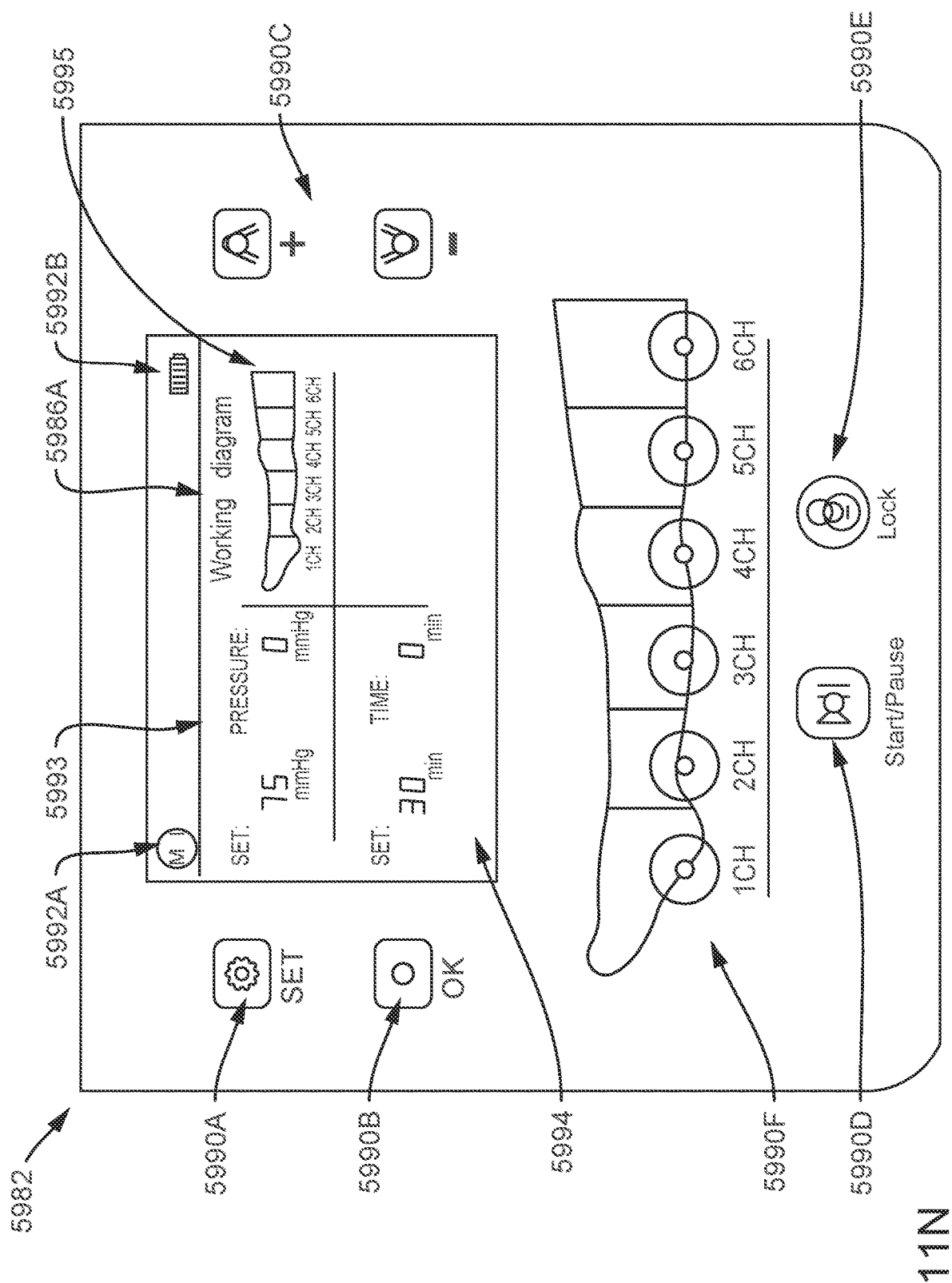
Figure 11O:
Figure 11P:
Figure 11Q:
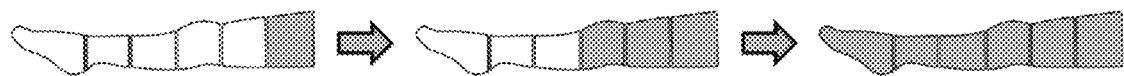
Figure 11R:
Figure 11S:
Figure 11T:
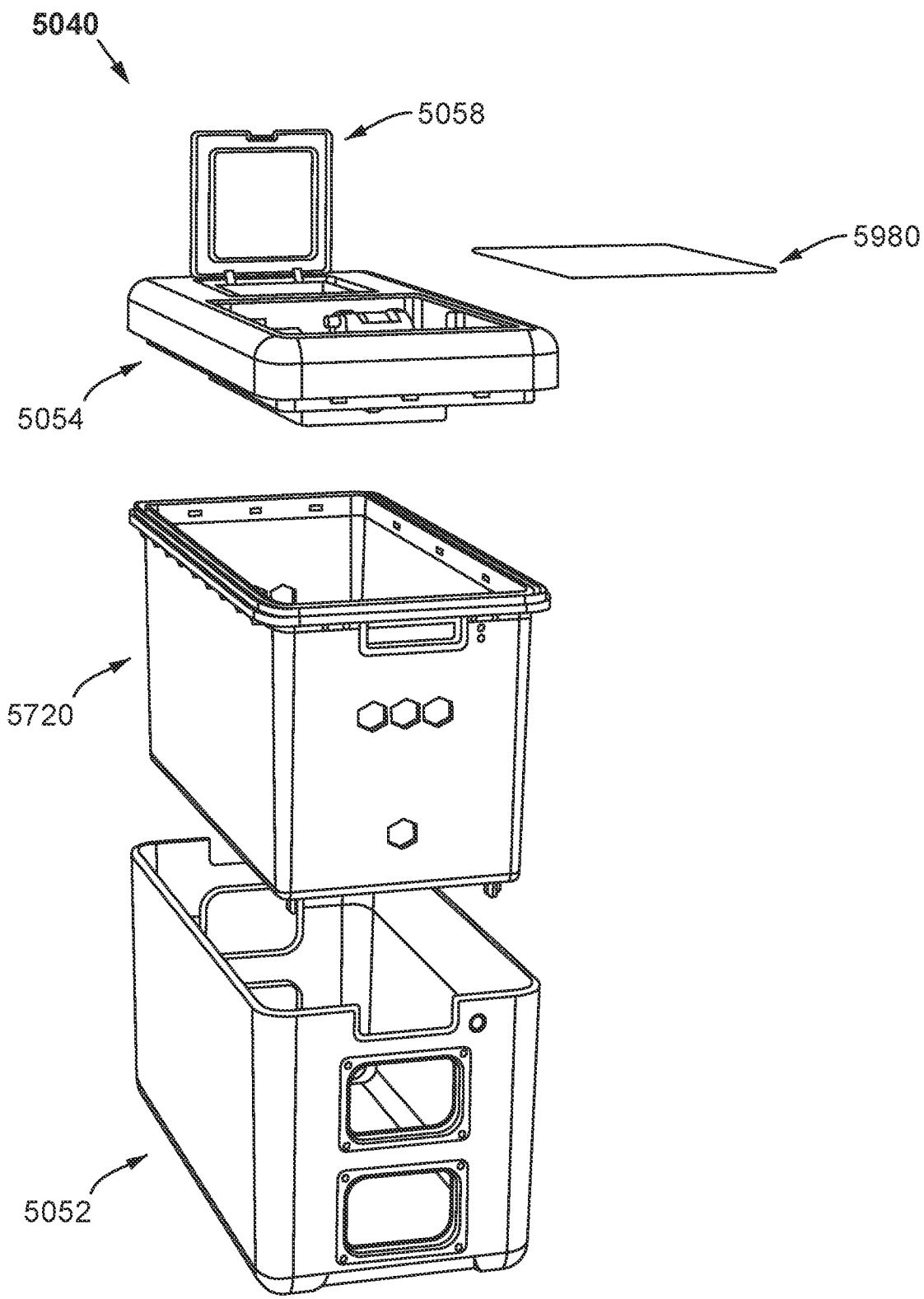

An embodiment of a treatment system is shown in FIGS. 11A to 11T. As shown in FIG. 11A, treatment system 5000 includes a control unit 5040 and two treatment delivery components 5020. Although shown with two treatment delivery components, system 5000 could include a single treatment delivery component. In this embodiment each treatment delivery component 5020 is configured to treat a lower limb (leg) of a user, and includes a leg portion 5022 that is configured to be disposed around the leg (thigh, knee, and calf), and a foot portion 5024 that is configured to be disposed around the foot (ankle and foot) of the user. The boundary between the leg portion 5022 and the foot portion 5024 is shown with a dashed line in FIG. 11A, but is shown only for ease of reference, and is not a precise boundary. Also shown in FIG. 11A is a pressure conduit 5250 for the pressure delivery component of each treatment delivery component 5020, as described in more detail below. Although this embodiment is configured to treat a lower limb of a user, other than the specific shape of treatment delivery component 5020 and arrangement of specific elements of treatment delivery component 5020, and some specific displays and controls for control until 5040, all of the features and functions described with reference to this embodiment would be applicable to treatment delivery components and control units configured to be used to treat other treatment portions TP, as are described above.

One of the treatment delivery components 5020 is shown in more detail in FIGS. 11B and 11C. FIG. 11B shows outer shell 5100 and pressure applicator 5210. In this embodiment, these two components are fixedly connected to each other. For example, a multi-layer construction, such as two layers of a material, each having fabric on the outside and plastic (airtight) on the inside may be inside (airtight), may be fused together to define the pressure applicator's pressure elements 5212 between the insides of each layer. In other embodiments, the pressure elements may be formed as discrete bladders, e.g., formed of elastomeric material, and the bladders may be disposed within pockets or sleeves formed of fabric material.

Outer shell 5100 includes a body portion 5110, which includes a leg portion 5112 and foot portion 5114 (corresponding to leg portion 5022 and foot portion 5024 of treatment delivery component 5020), again shown with a dashed line representing the boundary between the two portions only for ease of illustration. Outer shell 5100 also includes fastener portion 5120, which in this embodiment is implemented as a zipper, with cooperating portions on each edge of body portion 5110, extending along the entirety of leg portion 5112 and onto the upper part of foot portion 5114. Body portion 5110 is shown in FIGS. 11B and 11C as being in an open configuration, but for ease of illustration is shown fully opened, and flat. However, foot portion 5114 is fixed together around its perimeter along seam 5116 (e.g., by stitching, as can be seen in FIG. 11G) up to the lower end of the zipper of fastener portion 5112, and is thus configured to receive the foot of the user by having the foot slid into it, rather than receiving the foot and then being closed around the foot, as with the leg portion and the user's leg. The edges of the foot portion are not joined together at the center of the foot portion, i.e., where the heel of the user's foot would be disposed, leaving a gap that defines a passage 5130.

In this embodiment, pressure delivery component 5200 includes a pressure applicator 5210 with six pressure elements 5212 (five are shown here), each implemented as an expandable bladder. Each pressure element 5212 includes a pressure port 5214 through which pressurized fluid can be introduced into pressure element 5212 to change it from a collapsed configuration to an expanded configuration, and to increase its pressure, and from which pressurized fluid can be released or withdrawn to reduce its pressure and to change it from an expanded configuration to a collapsed configuration. In this embodiment, the pressurized fluid is a gas, e.g., air. Although not shown in FIG. 11B, each pressure port 5214 can be fluidically coupled to a respective fluid passage 5252 of pressure conduit 5250, and thus to pressure source 1600.

In this embodiment, pressure applicator 5210 includes optional thermal applicator couplers 5220, by which thermal applicator 5310 can be releasably coupled to pressure applicator 5210. In this embodiment, thermal applicator couplers 5220 are implemented as one half of a hook and loop fastener arrangement, with the mating (hook or loop) portion of the fastener arrangement disposed on one side of thermal applicator 5310 (as shown in FIG. 11C).

As shown in FIG. 11C, treatment delivery component 5020 includes a thermal delivery component 5300, with a thermal applicator 5310, a thermal conduit 5350, and a thermal connector 5360. In this embodiment, thermal applicator 5310 is implemented with a thermal element 5312 that is a flexible pad formed by fusing or otherwise securing two layers of polymer or other material together around their perimeter (defining the edges of thermal element 5312 and enclosing its overall volume) with elongate fused portions defining flow diverters 5313 that can direct the flow of fluid though thermal element 5312. The two layers can also be fused together at numerous small diameter spots to keep the pad relatively thin, rather than ballooning up when fluid is forced into and through it, and to more uniformly distribute the flow of thermal fluid through the interior of pressure element 5312. Thermal fluid can be introduced into, and withdrawn from, the interior of thermal element 5312 via thermal conduit 5350, which in this embodiment includes two fluid passages—one to introduce the thermal fluid and one to withdraw the thermal fluid. The two fluid passages couple to the interior of thermal element 5312 on opposite side of a central flow diverter 5313, so that fluid will circulate through the entire interior volume of the thermal element 5312. Thermal conduit 5350 terminates at thermal connector 5360. FIG. 11C shows thermal applicator 5310 disposed on, and releasably secured to, pressure applicator 5210, coupled by thermal applicator couplers 5220. In some embodiments, the side of thermal applicator couplers 5220 on thermal applicator 5310 may cover all or a large portion of the surface of thermal applicator 5310, such as by fixing a large area of hook or loop, that can be releasably secured to a relative narrow, elongate area of the mating loop or hook material fixed to the pressure applicator 5210. Thermal conduit 5350 is shown disposed in passage 5130 through foot portion 5114 of body portion 5110 of outer shell 5100. The arrows in FIG. 11E indicate that the edges of body portion can be approximated to enclose a user's leg, and releasably secured by fastener portion 5120.

Treatment delivery component 5020 is shown in cross-section (along line 11D-11D in FIG. 11A) in FIGS. 11D and 11E, secured to the treatment portion TP (leg) of the user. As shown in FIGS. 11D and 11E, body portion 5110 of outer shell 5100 is connected at its edges by fastener portion 1120 (zipper), and pressure element 5212 (bladder) of pressure applicator 5210 is secured to body portion 5110. Thermal applicator 5310 is secured (at its side portions 5316) to pressure applicator 5210 by thermal applicator couplers 5220 (hook-and-loop fasteners). In the configuration shown in FIG. 11D, pressure element 5212 is partially expanded, and has urged thermal applicator towards treatment portion TP (as indicated by the arrows), but there remains a gap or space between thermal applicator 5310 and treatment portion TP. In the configuration shown in FIG. 11E, pressure element 5212 is further expanded, and has pressed or urged central portion 5314 of thermal applicator 5310 into apposition with treatment portion TP (as indicated by the arrows), and has pressed side portions 1316 of thermal applicator 5310 together, "wasting" those portions of thermal applicator 5310. Thus, treatment delivery component 5020 has been adapted to the size of treatment portion TP (the user's leg) and is ready for delivery of thermal treatment by thermal applicator 5310, and/or pressure treatment by pressure element 5212 (and the other pressure elements 5212 of pressure applicator 5210), such as by further increasing the pressure of the gas within pressure element 5212 above the pressure required to establish apposition of thermal applicator 5310 with treatment portion TP.

FIG. 11F illustrates treatment delivery component 5020 in the same cross section as shown in FIGS. 11D and 11E, but disposed on a treatment portion TP (leg of user) having a smaller circumference than the treatment portion TP shown in FIGS. 11D and 11E. This view illustrates the size adapting functionality provided by pressure applicator 5210 (and pressure element 5212). Also shown in FIG. 11F is that pressure element 11F can be configured to expand to a greater degree upon pressurization on the upper side (as viewed in FIG. 11F) than the lower side of treatment delivery element 5020. Also shown in FIG. 11F is that the central, elongate fused portion or flow diverter 5313 of thermal applicator 5310 locally reduces the bending stiffness of thermal applicator 5310, so that thermal applicator 5310 preferentially folds or creases along the line of fused portion of flow diverter 5313 when the pressure element 5212 is expanded. This can fine tune the compliance of the thermal applicator 5310 to treatment portion TP, and avoid undesirable buckling or folding of thermal applicator 5310 that could interfere with complete apposition, and reduce the effectiveness of the thermal treatment delivery. More than one lengthwise-oriented fused portion can be formed to create more preferential fold lines. This approach can complement the "wasting" technique to maximize apposition and minimize buckling or folding.

Although the foregoing figures do not illustrate a liner, treatment delivery component 5020 could include a liner, as described above with respect to other embodiments.

Although treatment delivery component 5020 may be configured to adapt to a large range of sizes of treatment portion TP, e.g., of varying diameter of circumference, in some embodiments treatment delivery component 5020 may be configured to accommodate treatment portions having a range of axial sizes (e.g., length of leg), and it may be desirable to have different models or sizes of treatment delivery component 5020, e.g., short, regular, and tall, to accommodate different ranges of sizes of treatment portion TP.

FIGS. 11G to 11I are close-up views of the heel part of foot 5024 portion of treatment delivery component 5020— FIGS. 11G and 11H from the exterior, and FIG. 11I from the interior. Passage 5130 in outer shell 5100 can be seen in each figure. As shown in FIGS. 11G and 11H, thermal conduit 5350 is disposed in passage 5130, with thermal connector 5360 disposed on the exterior of treatment delivery component 5020. As best seen in FIG. 11G, in this embodiment outer shell 5100 includes conduit management 5140, which includes a conduit sleeve 5142 and conduit loop 5144 through which pressure conduct 5250 is disposed. Conduit management 5140 helps to protect thermal conduit 5250 from damage and/or entanglement with objects in the setting in which treatment system 5000 is used. It can also be seen in FIG. 11G that thermal conduit 5250 includes five separate fluid passages 5252, each of which is fluidically coupled to a respective pressure element 5212 via pressure port 5214, as described above.

Control unit 5040 is shown in more detail in FIGS. 11J to 11T. As shown in FIG. 11J, control unit 5040 includes a housing 5050 and a pressure coupling 5650 and thermal coupling 5750 on a front surface of housing 5050. As discussed above, in this embodiment, thermal treatment component 5300 employs thermal liquid, e.g., water. Correspondingly, thermal source 5700 includes a liquid reservoir 5720 and a liquid pump 5730 (not shown in these figures), which can supply thermal liquid to, and receive thermal liquid from, a thermal coupler 5750, disposed on the front face of housing 5050. Although not shown in these figures, in some embodiments control unit 5040 can include a second thermal coupling 5750, also fluidically coupled to liquid pump 5730 and liquid reservoir 5720, so that control unit 5040 can deliver thermal fluid simultaneously, or sequentially, to two treatment delivery components 5020, and thus to provide treatment to two users, or to two treatment portions of a single user. Thermal connector 5360 can be releasably coupled to thermal coupler 5750, establishing fluidic communication between thermal source 5700 and thermal applicator 5310 via thermal conduit 5350. Liquid reservoir 5720 may be filled with water that is below body temperature (such as ice water, for cryotherapy) and/or that is above body temperature (such as hot water, for heat therapy). Housing 5050 also includes an access lid 5058 that covers liquid reservoir 5720—water (cold or hot) can be introduced into liquid reservoir 5720 by opening access lid 5058. Thermal source 5700 also includes a drain 5760 by which reservoir 5720 can be drained of thermal liquid (e.g., water) after a treatment session.

As also discussed above, in this embodiment pressure treatment component 5200 employs pressurized gas (e.g., air) supplied by pressure source 5600. Correspondingly, a pressure coupler 5650 is disposed on the front face of housing 5050, which includes a gas pump 5630 (not shown), to which pressure connector 5260 can be releasably coupled, establishing fluidic communication between pressure source 5600 and pressure applicator 5210 via pressure conduit 5250. FIG. 11L shows a close-up view of pressure coupler 5650 and pressure connector 5260 at the end of pressure conduit 5250. As shown in FIG. 11L, pressure connector 5260 terminates in a set of male connectors 5261, each of which is in fluid communication with a respective fluid passage 5252 and can be mated to a respective female receptacle 5651 on pressure coupler 5650.

Control until 5040 also includes a user interface 5950 that includes an integrated display and user input 5980 (corresponding to display 1960 and user input 1970 of user interface 1950 of treatment system 1000, described above) disposed on an upper surface of housing 5050. In this embodiment, display and user input 5980 includes a thermal panel 5981 (which provides inputs for control of the function of the liquid pump 5730 and displays information about operation of the thermal treatment component 5300) and a pressure panel 5982 (which provides inputs for control of the function of the gas pump 5630 and displays information about operation of the pressure treatment component 5200).

As shown in FIG. 11M, thermal panel 5981 includes a temperature display 5983 and time display 5984, on which processor 5910 can cause to be displayed, respectively, a temperature relevant to thermal treatment (such as the temperature of the thermal liquid in the liquid reservoir 5720) and a time relevant to thermal treatment (such as the remaining time for the thermal treatment session). Thermal panel 5981 can also include indicators 5985 for the status of the pump (on or off) and whether the thermal system is operating in a pulse mode. Thermal panel 5981 also includes user inputs including power button 5986A (to turn on or off the thermal source 5700 (e.g., liquid pump 5730)), pulse button 5986B (to turn on or off a pulse mode of delivery), increase/decrease buttons 5986C (to increase or decrease, for example, program time), and main power button 5987 (to turn on or off the entire control unit 5900). The pulse mode of delivery may include operating the liquid pump on a duty cycle of, for example, two minutes on (pumping) and 30 seconds off.

As shown in FIG. 11N, pressure panel 5982 includes numerous user inputs. These can include: a) a mode set button 5990A (by which the user can select different operating modes for control unit 5040), b) pressure/time selection button 5990B (by which the user can select a time/pressure for operation), c) increase/decrease time/pressure buttons 5990C (to change a time/pressure to be selected for operation), d) start/pause button 1990D (to start or pause the pressure treatment operation); e) lock button 5990E (to lock the user interface against user inputs), and f) channel selection buttons 5990F (by which a user can selectively enable or disable each of the pressure elements 5212 (or chambers) from being actuated during a pressure treatment session. As also shown in FIG. 11N, pressure panel 5982 includes several displays. These can include: a) mode display 5992A (which can show which pressure treatment mode has been selected, e.g., mode 1 through mode 5); b) battery level display 5992B (which can show the state of charge of a battery power supply for control unit 5040), c) pressure display 5993 (which can show the set, or target, pressure for pressure treatment, and the current actual pressure in the pressure element(s) 5212 of pressure applicator 5210, or the output pressure of pressure source 5600), d) time display 5994 (which can show the set, or target, time for pressure treatment, and the current elapsed, or remaining, time in the pressure treatment session, and e) pressure element working display 5995 (which can display which pressure element(s) 5212 are currently pressurized, as described below in more detail with references to FIGS. 11O to 11S).

As noted above, pressure treatment can be delivered in different pressure treatment modes, which may be selected by the user (with mode set button 5990A). In this embodiment, five modes are available, which are illustrated in FIGS. 11O to 11S. One mode is sequential compression, from bottom (foot) to top. As shown schematically in FIG. 11O, in this mode pressure elements (or chambers) 5212 can be pressurized sequentially, beginning with the element at the foot (CH-1), with each pressure element 5212 remaining pressurized as the next element (moving away from the foot) is pressurized. After the last of the pressure elements 5212 are pressurized, all of the elements are depressurized, and the cycle can repeat. As noted above, the progress of the treatment session, i.e., the state of each pressure element 5212 (pressurized or not pressurized) can be displayed on pressure element working display 5995. Another mode is uniform compression. As shown schematically in FIG. 11P, in this mode all of the pressure elements 5212 are pressurized concurrently, and all are depressurized concurrently. Another mode is sequential compression, from bottom to top. As shown schematically in FIG. 11Q, in this mode the pressure elements 5212 are pressurized sequentially, as in the first mode, but in reverse order. Another mode is a variation on the sequential compression of bottom to top, but each pressure element 5212 is pressurized in turn, and is depressurized when the next pressure element in the sequence is pressured. This mode is shown schematically in FIG. 11R. Another mode is similar to the preceding mode, except that pressure elements 5212 are pressurized sequentially in pairs, as shown schematically in FIG. 11S. Other pressure treatment modes are possible—the modes described above are only exemplary. The user may select the magnitude of the pressure to be delivered, such as, for example, between 20 and 150 mmHg (gauge pressure). The user may also select the duration of a therapy session, such as, for example, between 20 and 200 minutes.

Some of the main components of control unit 5040 is shown in an exploded view in FIG. 11T. As can be seen in FIG. 11T, housing 5050 of control unit 5040 can include a lower housing portion 5052 and an upper housing portion 5054. Most of the volume within control unit 5040, between lower housing portion 5052 and upper housing portion 5054, is occupied by liquid reservoir 5720, into which a user can pour thermal fluid via the opening in upper housing portion 5054 selectively covered by access lid 5058. Display/input 5980 is disposed on the upper surface of upper housing portion 5054, and covers a cavity within which other components of control unit 5040 can be disposed (e.g., pressure source 5650, liquid pump 5730).

Many of the components of control unit 5040 (including pressure source 1600, liquid pump 1730, controller 1900, and user interface 1950 may be operated using electrical power. Such power may be provided by an internal battery or an external power supply, such as a plug to a wall outlet.

Consistent with the process described above with reference to FIG. 8, a user may use treatment system 5000 by disposing a leg in treatment delivery component 5020, and then close outer shell 5100 with fastener portion 5120 (i.e., zip up the zipper), such as while seated on the floor or a couch, chair etc. The user can then power on controller 5020, select a treatment session duration, thermal treatment mode, pressure treatment mode, etc., to receive the selected treatment.

Although treatment delivery component 5020 is configured to treat essentially the entire leg of a user, all of the structures, components, and techniques described above could be used with a device that extends over a much more finite axial length, such as all or a portion of the thigh, or just a knee, ankle, etc. In some embodiments, a pressure applicator could extend over the entire leg (or other body part) and a thermal applicator or other treatment applicator could extend over only a portion of the leg, or vice versa. Thus, for example, in treatment delivery component 5020, pressure applicator 5210 extends over the entire leg (including the foot), but thermal application 5310 ends above the foot.

Figure 12A:
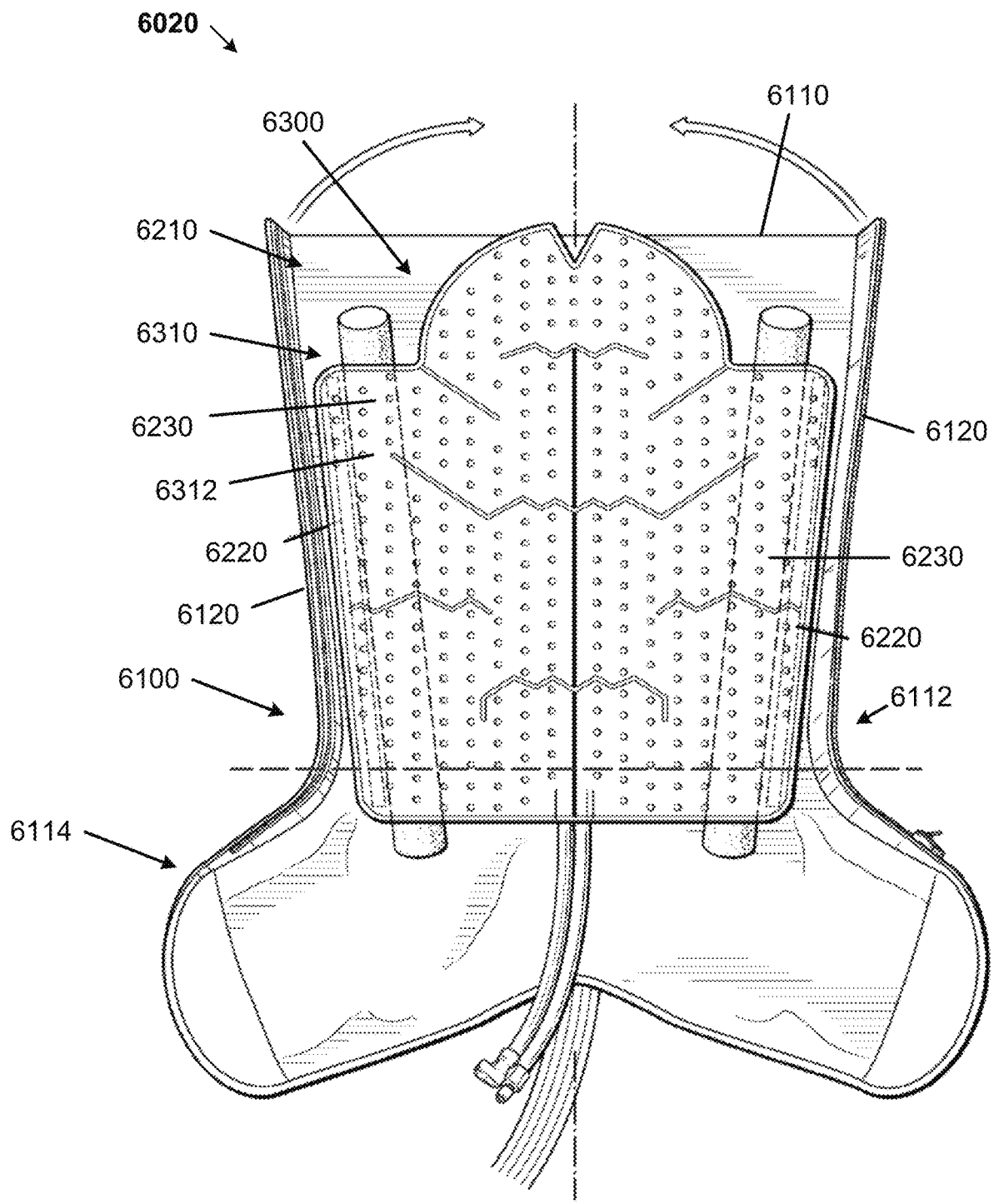
FIGS. 12A and 12B are illustrations of a treatment delivery component, according to an embodiment.
Figure 12B:
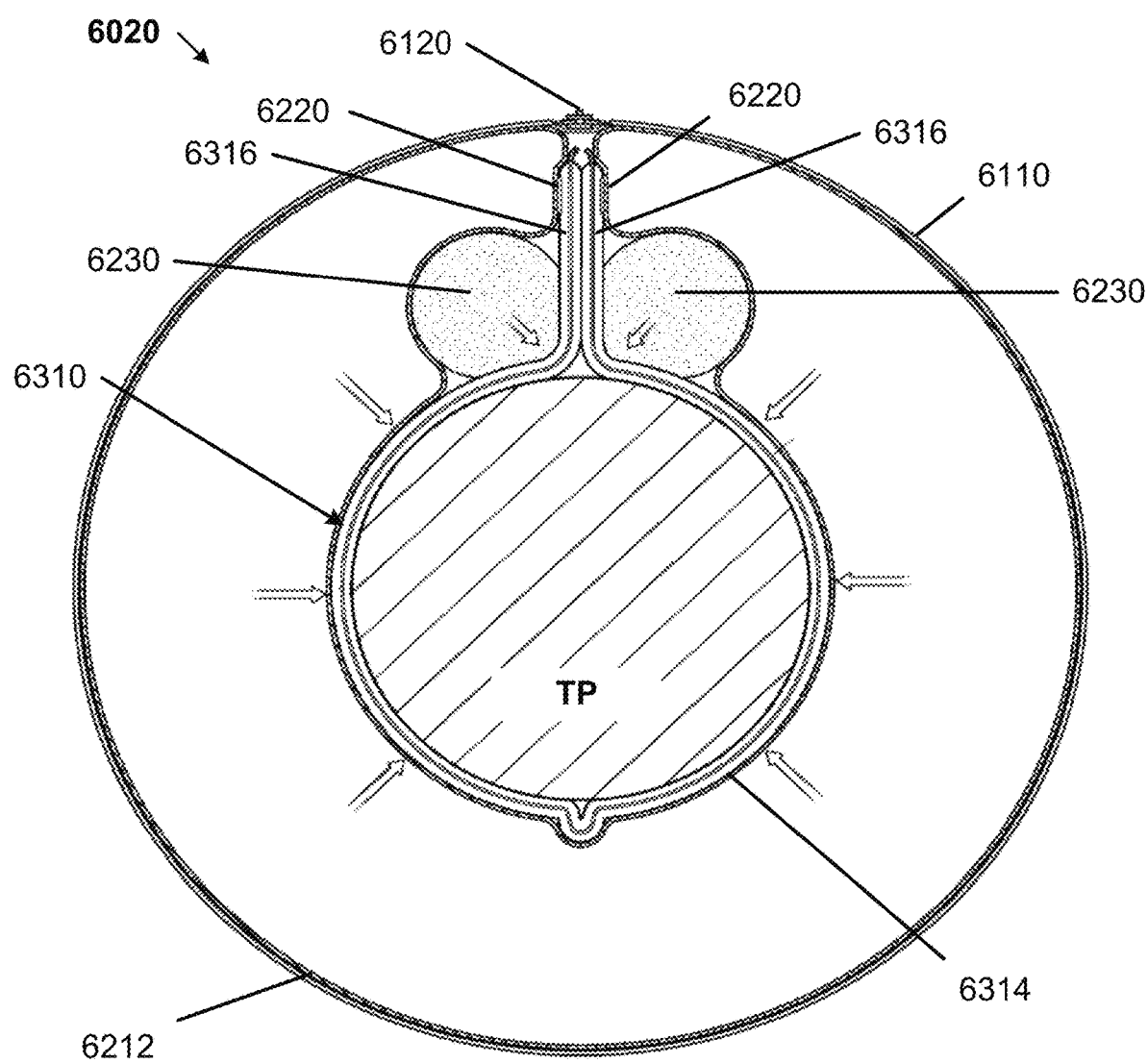

Although the size adaptability/pad "wasting" functionality is described above with respect to treatment delivery components 4020 and 5020 as being achieved only with pressure applicator 4210 and 5210, respectively, in other embodiments this functionality can be achieved in whole or in part with a mechanism that is separate from the pressure applicator. One such embodiment is shown in FIGS. 12A and 12B. In this embodiment, treatment delivery component 6020 is similar to treatment delivery component 5020, except that it also includes longitudinally oriented bolsters 6230. Elements that are the same as those in delivery component 5020 are not discussed in detail here.

As shown in FIG. 12A, treatment delivery component 6020 includes a thermal delivery component 6300, with a thermal applicator 6310 disposed on, and releasably secured to, pressure applicator 6210, coupled by thermal applicator couplers 6220. As with treatment delivery component 5020, outer shell 6100 and pressure applicator 6210 are fixedly connected to each other, and pressure applicator 6210 includes multiple pressure elements 6212. Outer shell 6100 also includes fastener portion 6120, which in this embodiment is also implemented as a zipper, with cooperating portions on each edge of body portion 6110. Bolsters 6230 are shown disposed between pressure applicator 6210 and thermal applicator 6310, with one disposed adjacent each side portion 6316. Bolsters 6230 thus fill some of the volume between outer shell 6100 and treatment portion TP that would otherwise need to be filled by pressure elements 6312 in their expanded configuration to adapt treatment delivery component 6020 to treatment portion TP to provide proper apposition of central portion 6314 of thermal applicator 6310 with treatment portion TP and to press side portions 6316 against each other, to "waste" those portions of thermal applicator 6310.

Bolsters 6230 are used in this embodiment to complement pressure elements 6212 to waste thermal applicator 6310, and accommodate a user with a relatively small treatment portion TP. For users with relatively larger treatment portions TP, bolsters 6230 may not be necessary, or may impede the adaptation of treatment delivery component 6020 to treatment portion TP (e.g., if the size of treatment portion TP is close to the maximum size capacity of treatment delivery component 6020). For very small users, it may be desirable to insert more than one bolsters 6230 (two, three, or more) adjacent each side portion 6316. It may thus be advantageous for bolsters 6230 to be separable from treatment delivery component, so that a user may insert one or more bolsters 6230 if treatment portion TP is relatively small, or dispense with their use if treatment portion TP is relatively large. In some embodiments, a single bolster 6230 may be used, i.e., adjacent to only one side portion 6316.

The dimensions of each bolster 6230 may vary depending on the desired volume for bolsters 6230 relative to the total volume within outer shell 6100. If two (or more) bolsters are used, they may be of different sizes, and a user may select from a range of sizes of bolsters for a given treatment portion, desired therapy session parameters, etc. Although shown in FIG. 12B as being circular in cross-section, bolsters 6230 may be of any desired cross-sectional geometry, e.g., rectangular, triangular, oval, etc. Although shown in FIG. 12A as being of constant diameter along their length, bolsters 6230 may have varying diameters (or size or perimeter of non-circular cross-section) along their length. For example, it may be desirable for the bolster to have a larger cross-sectional area near the foot (where treatment portion TP would have a smaller cross sectional area) and larger near the top of the leg. As shown in FIG. 12A, each bolster 6230 may extend essentially the entire length of pressure applicator 6210, i.e., between every pressure element 6212 and thermal applicator 6310. In other embodiments, bolsters 6230 may be between only one or some of pressure elements 6212 and thermal applicator 6310. In other embodiments, treatment delivery component 6020 may include two or more bolsters on each side of thermal applicator 6310, rather than a single bolster 6230.

The mechanical properties (e.g., compressibility, flexural stiffness) of bolsters 6230 may be selected to achieve desired functionality. For example, it may be preferable for bolster 6230 to be sufficiently stiff (in compression) to provide desired thermal applicator wasting for a small user, but sufficiently compressible to allow adaptation to a relatively larger user (and treatment portion TP). Bolster 6230 may therefore be formed of, for example, a foamed polymer having a suitable density to yield the desired stiffness/compressibility. In some embodiments, bolster 6230 may be hollow, or otherwise be heterogeneous in cross-section (e.g., with two or more layers of material with differing mechanical properties).

Bolsters 6230 may simply be inserted between pressure applicator 6210 and thermal applicator 6310 and retained in place by friction/pressure. In some embodiments, bolsters 6230 may be retained in a desired location by being fastened to one or both of pressure applicator 6210 and thermal applicator 6310 by fasteners, e.g., hook and loop fasteners. The position of bolster(s) 6230 relative to thermal applicator 6310 could also be adjusted so that pressure applicator 6310 can be used for different sizes of treatment portion TP. Indicia such as lines could be marked on the back of treatment applicator 6310 to indicate where to attach bolster 6230 to treatment applicator 6310 to aid the user in positioning bolster 6230.

Figure 13A:
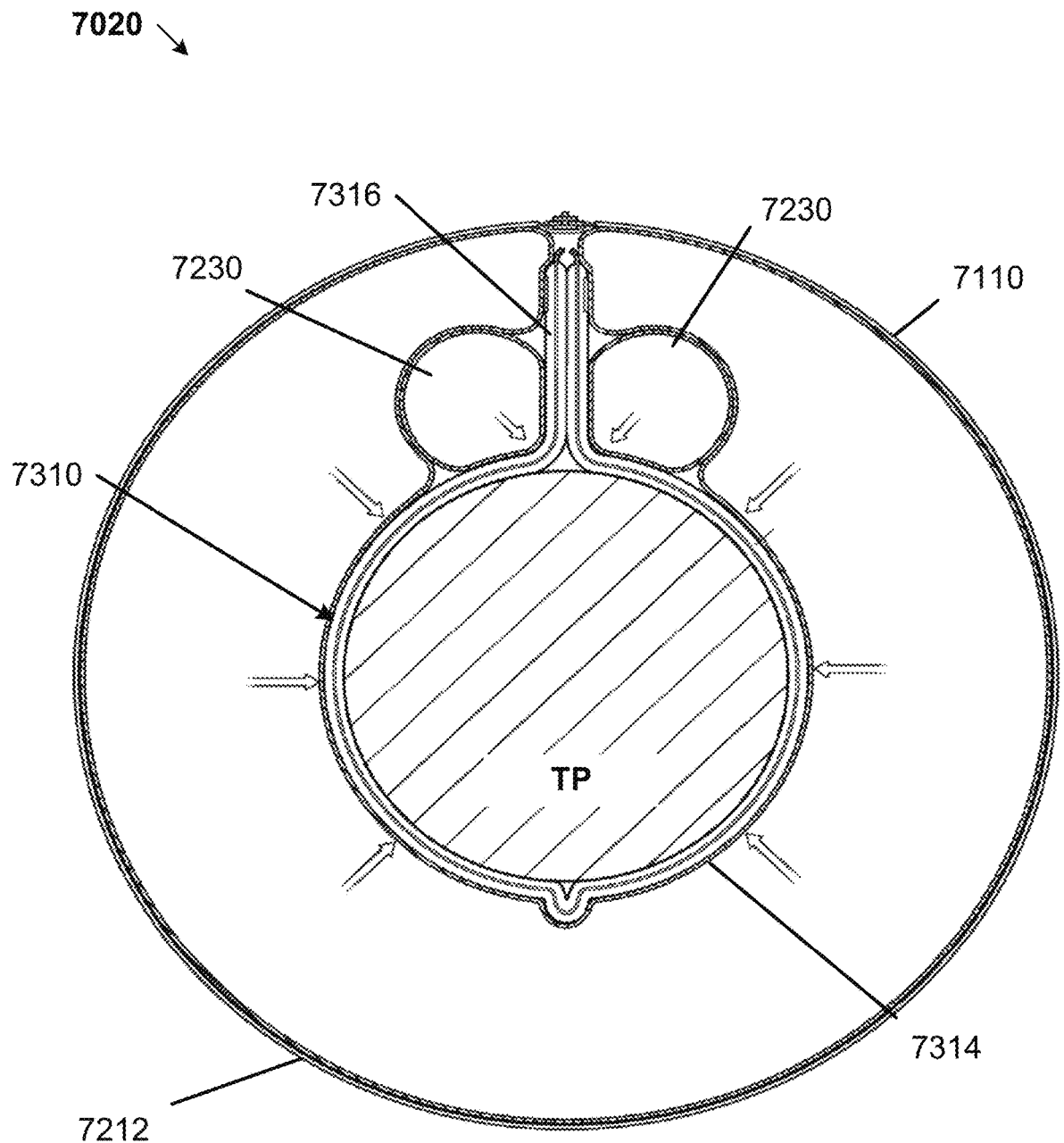
FIGS. 13A and 13B are cross-sectional views of treatment delivery components, according to embodiments.

In some embodiments the bolsters can be inflatable structures that may be actuated by the same pressure source used to actuate the pressure elements, or by some other means. One such embodiment is shown in FIG. 13A. Treatment delivery component 7020 includes bolsters 7230, which are implemented as inflatable tubes or bladders. Pressurized gas to inflate or expand bolsters 7020 may be supplied by the same pressure source that supplies pressurized gas to pressure elements 7212, or may be supplied by a separate source. The controller may be operated to inflate or expand bolsters 7320 to a selected pressure, or a user my control their inflation until thermal applicator 7310 feels appropriately tight on treatment portion TP. Bolsters 7320 may be inflated or expanded before, after, or concurrently with initial inflation of pressure elements 7212 until proper adaptation of treatment delivery component 7020, and apposition of central portion 7314 of thermal applicator 7310 is achieved, before delivery of selected thermal and/or pressure treatment modalities. As with bolsters 6230, bolsters 7230 may have various cross sectional shapes, may vary in cross sectional shape and/or area along the length of bolsters 7320, may be continuous or segmented, may be of any desired number (one, two, or more), may extend the full length of thermal applicator 7310 or only part of its length, etc.

Although referred to in the preceding embodiments as bolsters, with a focus on the functionality of wasting the thermal applicator, each inflatable bolster can also be considered to be another pressure applicator, can thus in addition to wasting the thermal applicator, the bolster can deliver pressure treatment. Inflatable bolsters with an axially elongate configuration can provide pressure treatment to an elongated part of a treatment portion, e.g., to the full length of a user's thigh or calf, and in a circumferentially finite portion, e.g., only to the front of the thigh (such as the quadriceps), alone or in conjunction with circumferentially oriented and more axially finite pressure elements. As noted above, the inflatable, or expandable bolsters, or axially elongate pressure elements, can be asymmetric with respect to the treatment portion or the other components of the treatment delivery component. Similarly, as shown in FIG. 11F, each pressure element can also be circumferentially asymmetric, e.g., to expand to a greater degree on one side of treatment portion TP and a lesser degree on the opposite side. Such asymmetry can be created by the geometry or dimensions of the bladder or envelop of material used to form the pressure element. In some embodiments, as described above with reference to FIGS. 3N and 3O.

One or more inflatable bolsters such as bolster 7230 could also be used independently of a pressure applicator such as pressure applicator 7210, e.g., to tension a thermal applicator or other treatment applicator circumferentially around a treatment portion.

Figure 13B:
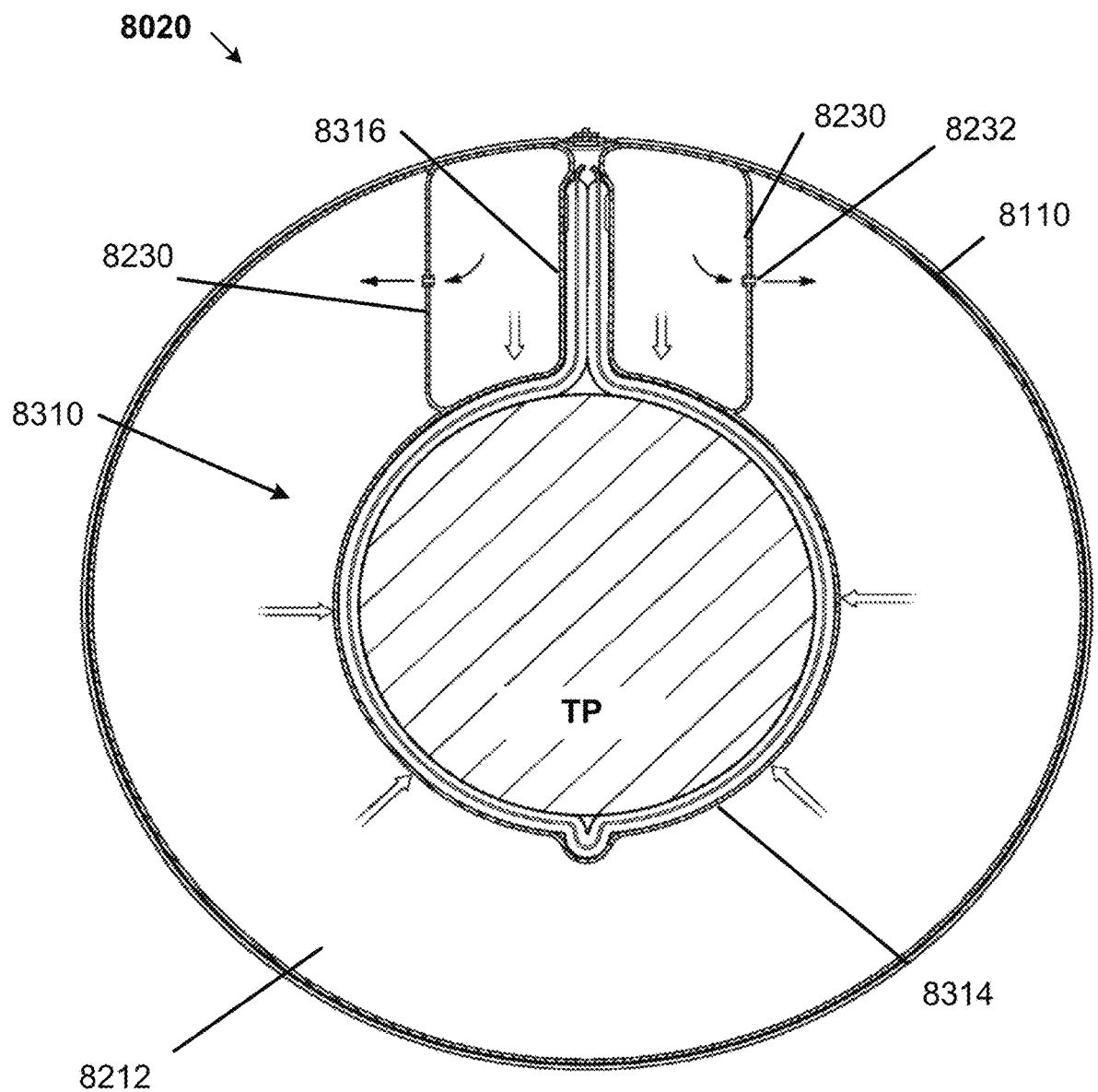

Another embodiment of an inflatable bolster is shown in FIG. 13B. Treatment delivery component 8020 is very similar to treatment delivery component 7020 shown in FIG. 13A, so elements that are the same are not discussed in detail here. In this embodiment, bolsters 8230 are also inflatable, but have a generally rectangular, rather than circular, cross-section. Each bolster 8230 also includes a connecting port 8232 that provides fluidic communication between the interiors of bolsters 8230 and each pressure element 8212. Only one pressure element is shown in the view in FIG. 13B, but this view is a cross-section through one axial location of treatment delivery component 8020, which can have multiple, axially-distributed pressure elements 8212, in the same manner as treatment delivery element 5020, described above. Pressurized gas from the pressure source can be introduced first into bolsters 8230 to expand them and adapt treatment delivery element 8020 to treatment portion TP, and from bolsters 8230 can flow into pressure elements 8212.

Figure 14A:
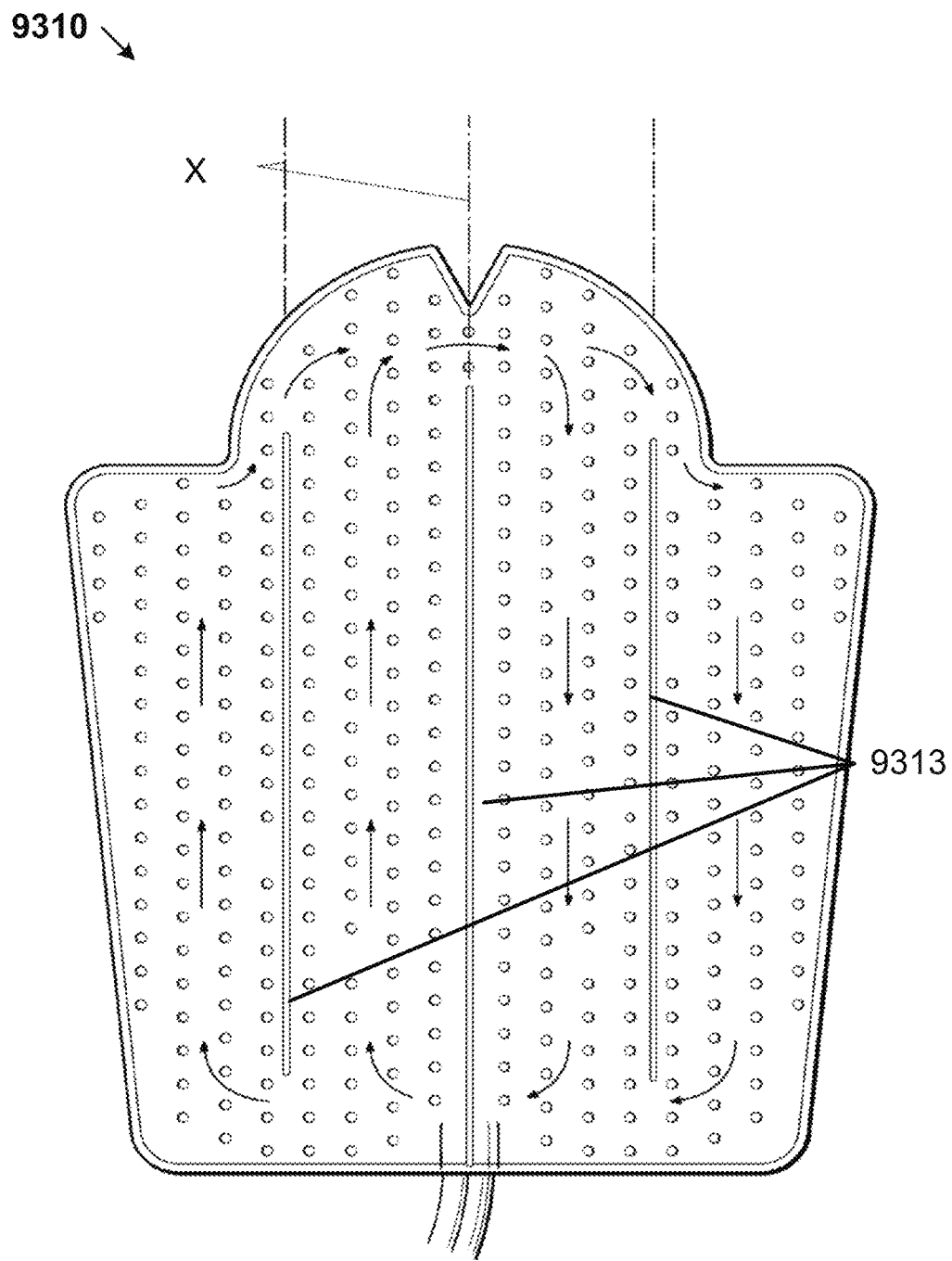
FIG. 14A is a plan view of a thermal applicator.
Figure 14B:
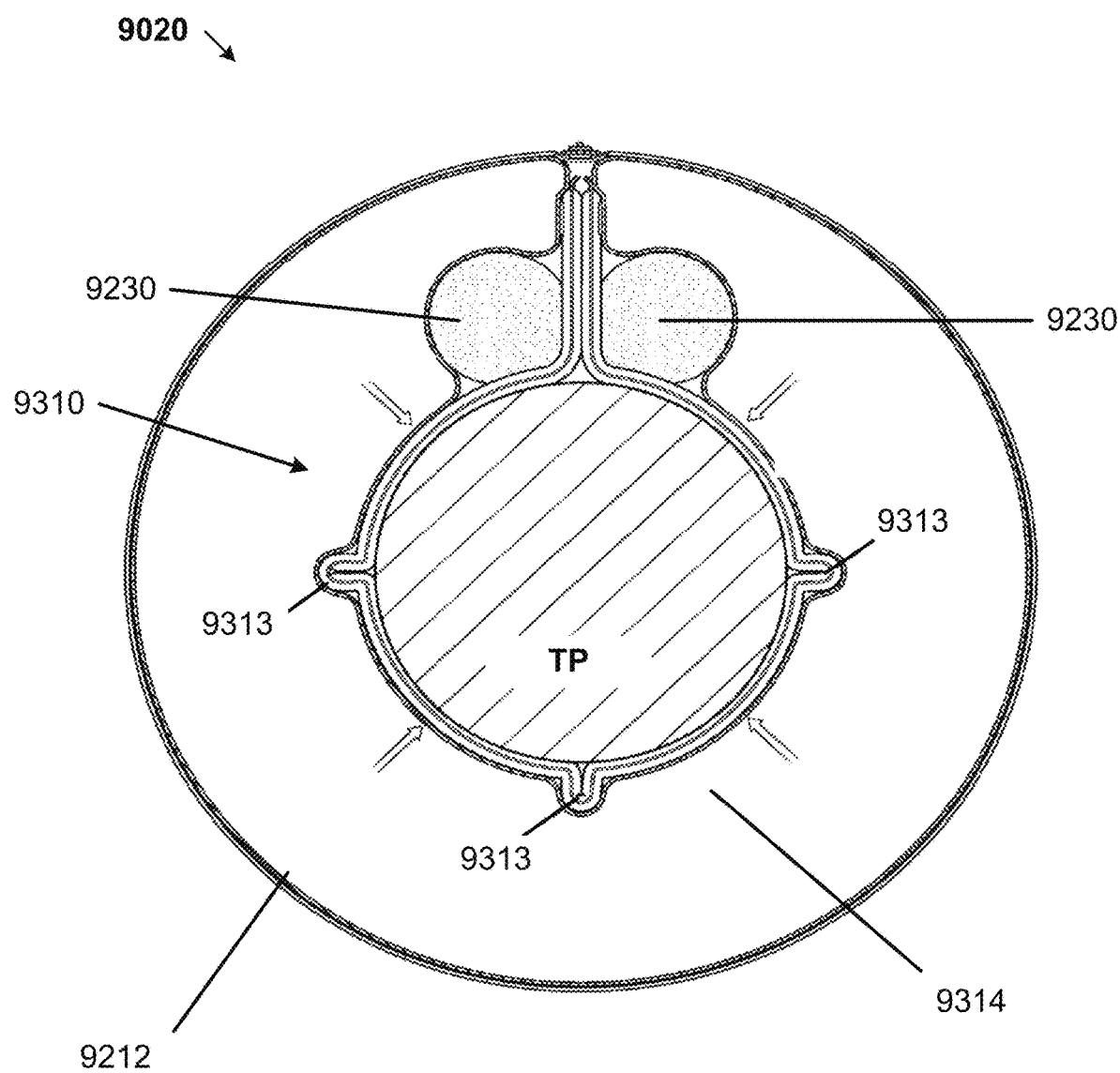
FIG. 14B is a cross-sectional view of a treatment delivery component including the thermal applicator of FIG. 14A, according to an embodiment.

As discussed above, the thermal applicator can be formed with elongated fused portions that function both as flow diverters for the thermal fluid that can circulate through its interior, and also form a preferential folding location, the arrangement of which can aid in conformation or apposition of the thermal applicator with the treatment portion of the user body. This functionality can be combined with that of the bolsters, as is illustrated in FIGS. 14A and 14B. Thermal applicator 9310 includes three longitudinally-extending flow diverters 9313, which can create preferential fold lines indicated in FIG. 14A by the dashed lines labeled with an X. As can be seen in FIG. 14B, these fold lines can further facilitate or enhance the apposition of central portion 9314 of thermal applicator 9310 with treatment portion TP provide by bolsters 9230 (which may be the same as any of the bolster embodiments describe above). Many variations on this approach to the use of flow diverters 9313 are possible. There could be any number of seams or plications formed by flow diverters. Although shown as longitudinal in FIGS. 14A and 14B, flow diverters could also be arranged laterally, for horizontal folding or plication. The width of the fused portion defining the flow diverters can also vary in width—a wider fused seam will accommodate more plication. Moreover, the flow diverters 9313 may facilitate uniform distribution of the thermal fluid through the internal volume of the thermal applicator 9310 to provide heat treatment to substantially the entire surface of the treatment portion that is the target of the thermal treatment, as well as providing a preferential flow direction for the thermal fluid to enter and exit the thermal applicator 9310.

Figure 15:
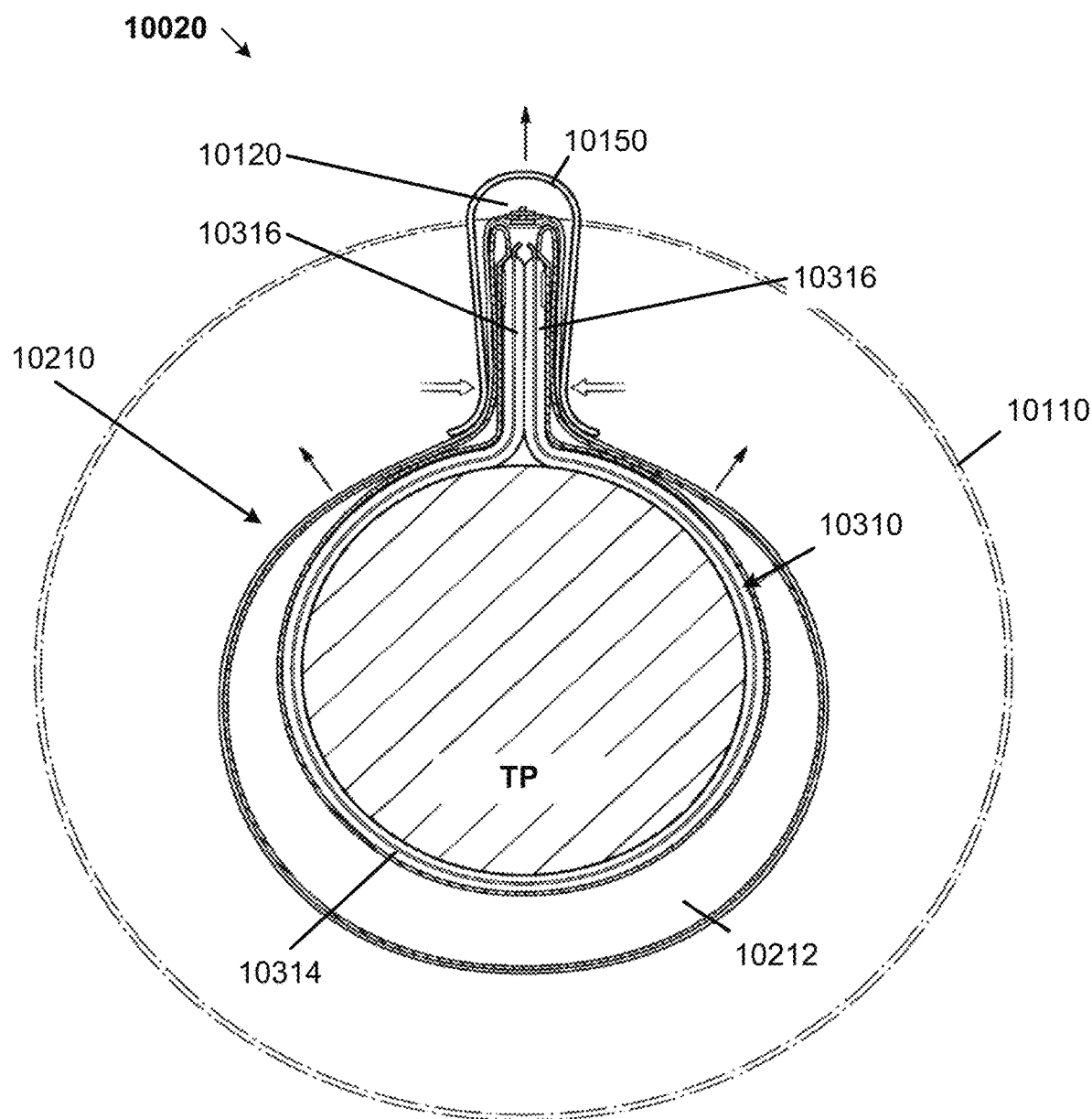
FIG. 15 is a cross-sectional view of a treatment delivery component, according to an embodiment.

Mechanisms other than bolsters may be used to "waste" the thermal applicator and adapt the treatment delivery component to the treatment portion. One alternative mechanism is shown in FIG. 15. Treatment delivery component 10020 is very similar to treatment delivery component 5020 described above, so elements that are the same are not discussed in detail here. Treatment delivery component 10020 can include multiple waste clamps or clips 10150, which can be applied to treatment delivery component 10020 after it has been enclosed around treatment portion TP, across the edges of body portion 10110 where they are joined by fastener portion 10120 (e.g., zipper). The user can gather together the side portions 10316 into apposition with each other, and drawing central portion 10314 of thermal applicator 10310 into apposition with treatment portion TP, pinching together as well the overlying portions of body portion 10110 and pressure applicator 10210. Pressure elements 10212 can then be expanded by introduction of pressurized gas, and as their volume increases, waste clip 10150 can be urged away from treatment portion TP and ultimately off of treatment delivery component 10020. Waste clips 10150 can vary in size for application to different axial portions of treatment delivery components 10020 to accommodate different amounts of wasting required with different cross-sectional areas of treatment portion TP (e.g., more wasting at the ankle than at the thigh of a leg). Waste clips 10150 can be formed of any suitable material that is resilient, can provide the needed clamping force, slidably disengage from treatment delivery component 10020 as pressure elements 10212 expand, etc.

Figure 16:
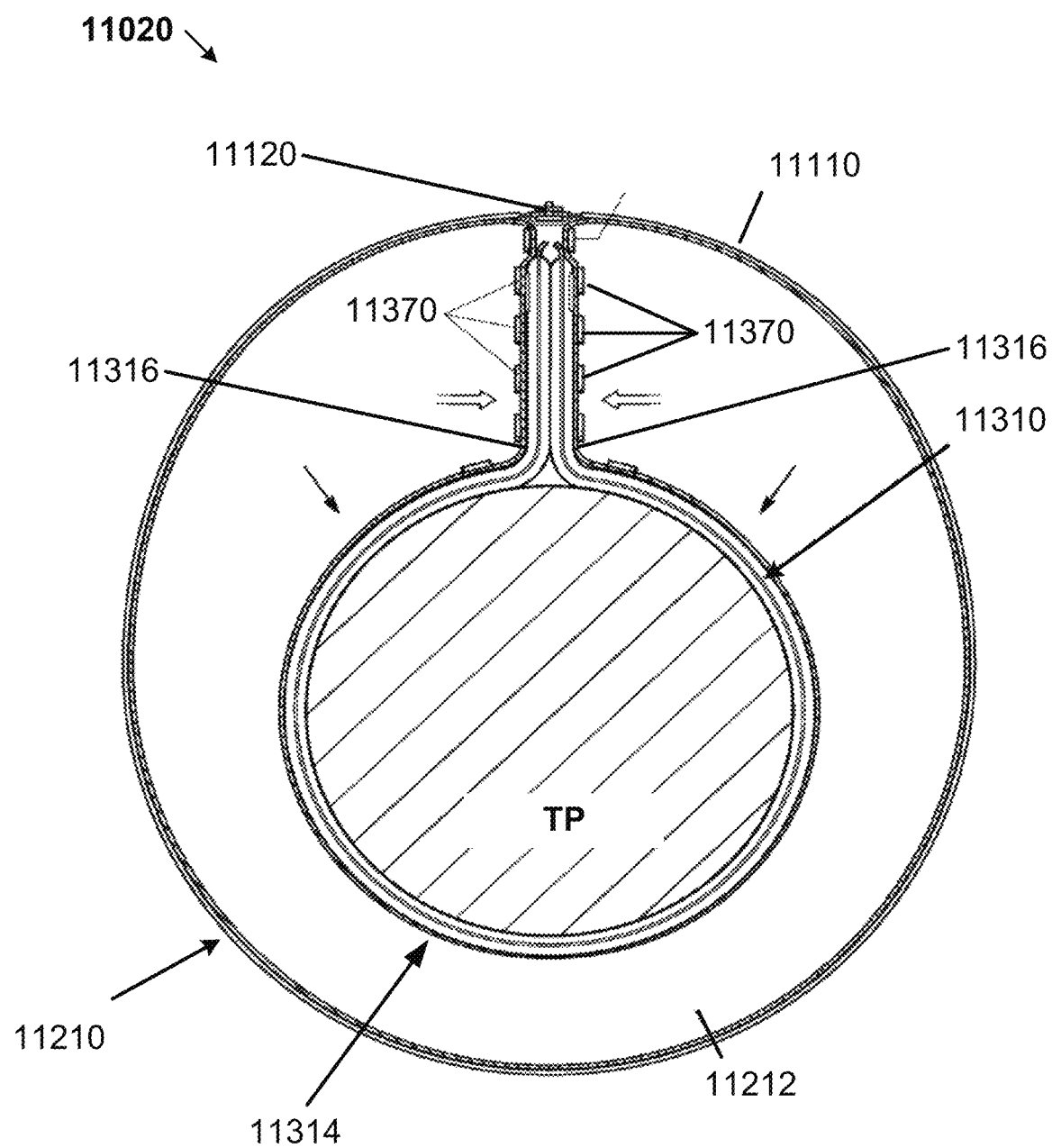
FIG. 16 is a cross-sectional view of a treatment delivery component, according to an embodiment.

In another embodiment, shown in FIG. 16, the externally-applied clamping force provided by waste clips can be replaced by magnetic attraction force. In this embodiment, treatment delivery component 11020 includes a thermal applicator 11310 with side portions 11316 and central portion 11314. Thermal applicator 11310 also includes include a set of waste magnets arranged in mating, mutually magnetically attractive pairs on the laterally outer portions thereof. Each pair of waste magnets 11370 can be attracted towards each other (as indicated by the larger arrows in FIG. 16) with sufficient force to approximate the inner surfaces of side portions 11316, and aid in effective apposition of central portion 11314 with treatment portion TP (as indicated by the smaller arrows in FIG. 16). The number of pairs of waste magnets 11370 that are engaged to waste side portions 11316 depends on the size of treatment portion TP—the smaller the treatment portion TP, the more pairs of waste magnets 11370 are required to waste side portions 11316. Although waste magnets 11370 are shown in FIG. 16 as disposed on an outer (back) surface of thermal applicator 11310, in other embodiments they can be disposed in an inner (front) surface, or incorporated into, thermal applicator 11310. As will be apparent from the illustrations of other embodiments, FIG. 16 is a cross-section through one axial location of treatment delivery component 11020—multiple sets of waste magnets 11370 can be disposed at other axial locations, and each axial location may have more or fewer pairs of magnets (e.g., fewer at the top of a leg and more at a bottom of a leg). A user can adapt treatment delivery component 11020 to a treatment portion TP by approximating the side portions 11316 of thermal applicator 11310 sufficiently closely for the magnetic attraction of mating pairs of magnets to draw the side portions fully together. The user may then approximate the edges of body portion 11110 and fasten them together with fastener portion (e.g., zipper) 11120, and then initiate treatment via the control unit.

Figure 17A:
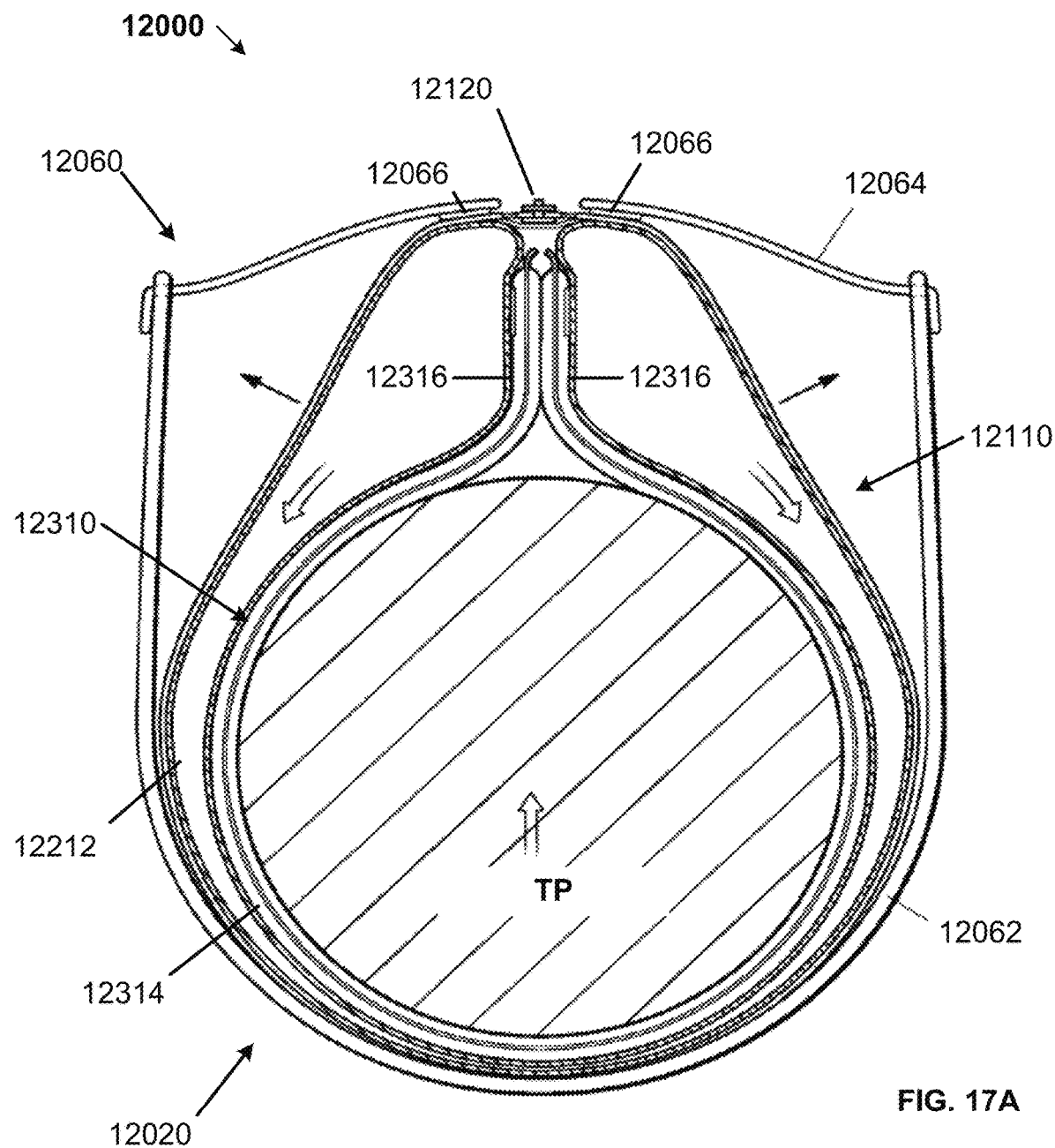
FIGS. 17A and 17B are illustrations of a treatment delivery component support, according to an embodiment.
Figure 17B:
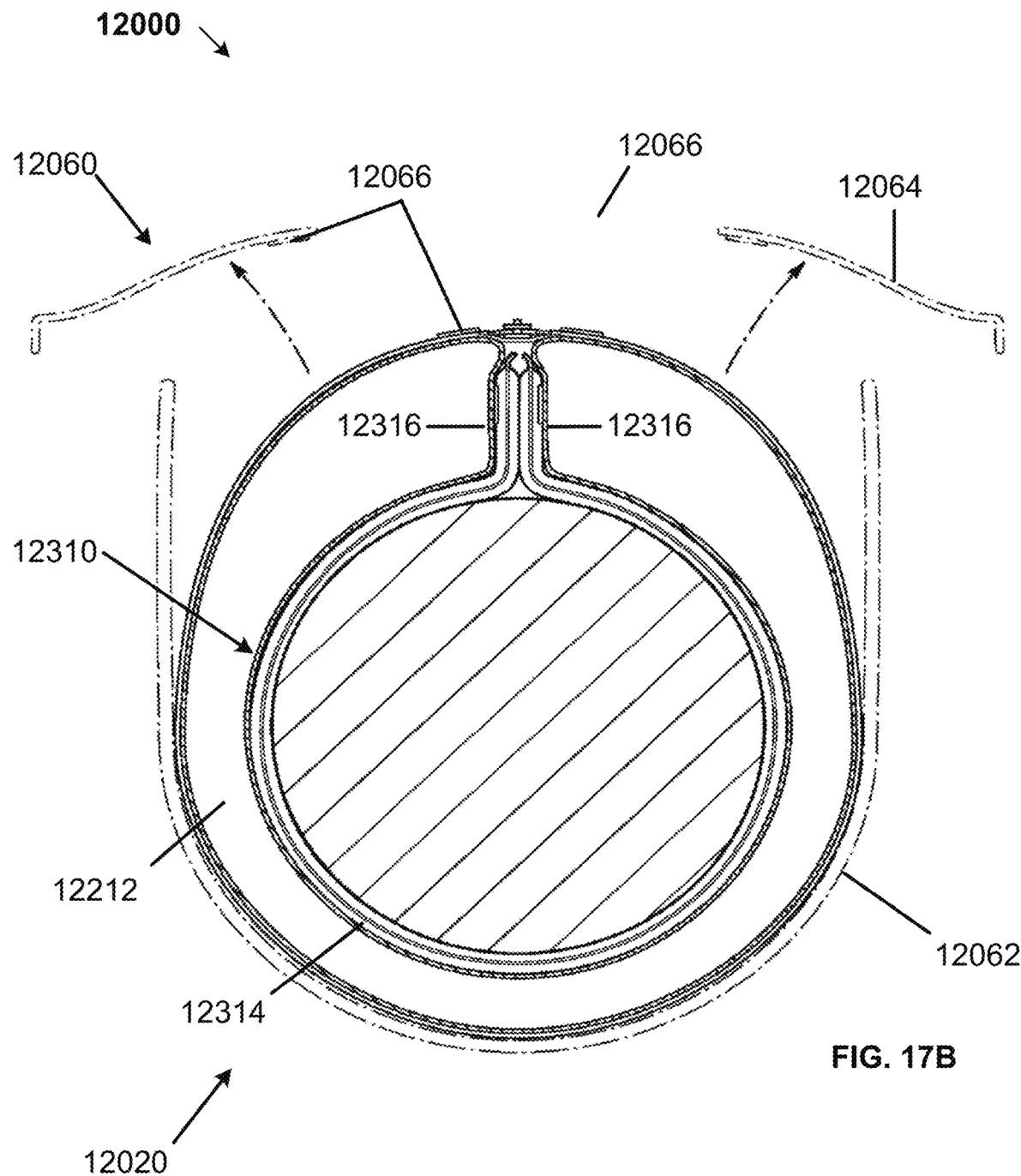

Other approaches besides the wasting described above can be employed to ensure good apposition of the central portion of the thermal applicator and avoid folds or creases that can compromise delivery of thermal treatment, e.g., by inhibiting of disrupting the flow of thermal fluid through the thermal applicator. One such approach is shown in FIGS. 17A and 17B. In this embodiment, treatment system 12000 includes treatment delivery component 12020 and a support frame 12060. Treatment delivery component 12020 is essentially the same as treatment delivery component 5020 described in more detail above. Both body portion 12110 and thermal applicator 12310 (as well as pressure applicator 12210) are relatively flexible, and therefore are not self-supporting, but tend to collapse or fall towards the ground when the user disposes treatment portion TP into treatment delivery component 12020. Support frame 12060 is configured to support treatment delivery component 12020, and in particular body portion 12110 and thermal applicator 12310 during the process of the user donning treatment delivery component 12020.

Support frame 12060 includes a U-shaped main frame 12062, and a pair of support arms 12064 releasably coupleable to the top or open end of main frame 12062. Support arms 12064 are also releasably connectable to body portion 12110 by support frame fasteners 12066 (e.g., hook-and-loop fastener). A user can dispose treatment delivery component 12020 into main frame 12062, attach support arms 12064 to main frame 12062, dispose treatment portion TP into the interior of treatment delivery component 12020 (i.e., on top of center portion 12314 of thermal delivery component 12310), lift up the edges of body portion 12110 and secure them together with fastener 12120, and engage them with support frame fasteners 12066. The edges of body portion 12110, and by extension the side portions 12316 of thermal delivery component 12310, are thus suspended from support frame, and central portion 12314 is free of any creases or folds. Pressure delivery component 12110 can then be actuated, and thus pressure element 12212 can be expanded, bringing center portion 12314 into good apposition with treatment portion TP and wasting side portions 12316, as shown in FIG. 17A. With treatment delivery portion 12020 properly adapted to treatment portion TP, support frame 12060 can then be removed from treatment delivery portion 12020, as shown in FIG. 17B, such as by releasing support frame fasteners 12066, removing support arms 12064 from main frame 12062 (as indicated by the dashed arrows), and removing main frame 12062 from around treatment delivery component 12020.

As described in detail above, treatment systems can be configured to deliver other treatment modalities (in addition to, or instead of, pressure and/or thermal treatment). One such treatment system is illustrated in cross-section in FIG. 18. Treatment delivery component 13020 is essentially the same as treatment delivery component 7020 described above, except for the addition of an other treatment delivery component, with an other treatment applicator 13410. In this embodiment, other treatment applicator 13410 is configured to deliver electrical stimulation, such as TENS, NEMS, PEMF. As described above, TENS treatment may be desirable for a variety of conditions, including for many painful conditions such as back pain, for muscle recovery, or to treat problems like phantom limb pain. NEMS can be used to increase strength and range of motion, and offset effects of muscle disuse (e.g., after surgery or coma to retrain or reeducate muscles to function normally and build strength). PEMF can be used to deliver electromagnetic or magnetic fields to treat, for example, chronic inflammation in joints or tissue, chronic fatigue symptoms or chronic fatigue syndrome, peripheral neuropathy, osteopenia or osteoporosis, poor wound healing, by enhancing body's natural recovery process, correcting cell dysfunction, and/or reducing inflammation. Other treatment applicator 13410 therefore includes individual electrodes 13412 that can deliver electrical stimulation to treatment portion TP when disposed in operative contact with the surface of treatment portion TP and receive electrical energy from a suitable source (as described above). To improve contact with the surface of treatment portion TP, electrodes 13412 could be located and spaced individually with wires or electrical leads (not shown in FIG. 18) passing from along the inside thermal applicator 13310 pad to its surface, or with wires attached to electrodes 13412 that pass through thermal applicator 13310 then to its outside. The wires or electrical leads could pass between the pressure applicator 13210 and the outer surface of other treatment applicator 13410 (or thermal treatment applicator 13310), and then through an opening in the outer shell of treatment delivery component 13020, as with pressure conduits and or thermal conduits, as described above.

In this embodiment, other treatment applicator 13410 is coupled to, or incorporated with, thermal applicator 13310, but in other embodiments (as described above), other treatment applicator 13410 can be separate from thermal applicator 13310, or used as part of a treatment delivery component that does not include a thermal applicator. Thus, electrodes 13412 could be disposed on the surface of a separate fabric or membrane. They could also be mounted on solid surfaces or on mesh structures which can separate the electrodes but allow for contact with the skin. The meshes could be constructed from fabric, elastic, metal or plastic or any other mounting structure. Pads or surfaces with electrodes could be compressed against the skin. The electrodes could be attached to wires that carry them to a controller device that would power and/or regulate the energy delivered. They could travel out of the boot from either end and may accompany the fluid tubes if these are used. The wires could also pass through a seam in the boot construction.

In this embodiment, other treatment applicator 13410 is coupled to, or incorporated with, thermal applicator 13310, in particular central portion 13314 thereof. No electrodes are shown in side portions 13316 of thermal applicator 13310, but electrodes could be disposed across the full width of thermal applicator 13310, and only electrodes that are in contact with treatment portion TP may receive electrical energy.

As with other embodiments illustrated above, FIG. 18 illustrates a cross section of treatment delivery component 13020 at one axial location, but treatment delivery component can have a similar configuration at other axial locations, e.g., include multiple rows of electrode 13412.

Figure 18:
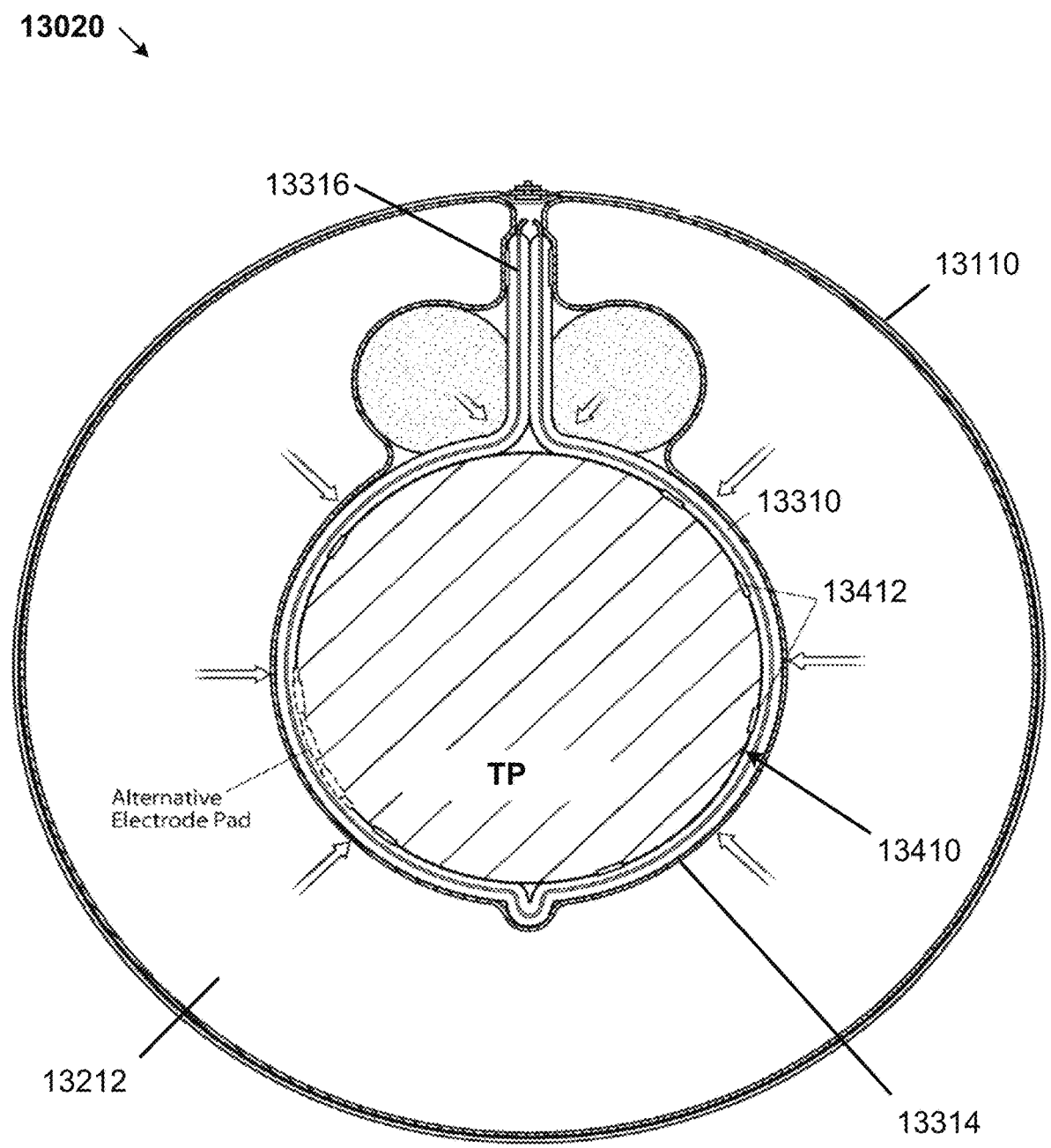
FIG. 18 is a cross-sectional view of a treatment delivery component, according to an embodiment.

Any of the wasting techniques described above are beneficial not just for thermal applicators, but also for other treatment applicators such as the TENS, NEMS, and/or PEMF delivery device shown in FIG. 18. The benefits of good, uniform apposition with treatment portion TP, without creases, folds, or other disruptions to uniform application of the treatment applicator can be even more useful for treatment modalities such as TENS, NEMS, and/or PEMF in which the spacing of the electrodes (or magnetic field generators) may be optimized for the treatment, and the spacing is preferably maintained during adaptation of the treatment delivery component to the treatment portion.

Electrodes 13412 could be replaced by electrical heating elements, such as the elements commonly used in heating pads and blankets. This would allow treatment portion TP to be heated electrically, while being cooled with cold thermal fluid in thermal treatment applicator 13310. This would allow for a simpler control unit, by eliminating the need for supplying hot thermal fluid, reducing weight and cost.

As noted above, other treatment modalities can involve the use of magnets. Thus, in some embodiments, electrodes 13412 could be replaced by permanent magnets or by electromagnets powered by wires or electrical leads connected to a power source in the control unit of the treatment system.

As discussed above, a treatment delivery component can be configured to treat any one or more of different treatment portions of a user's body. The embodiments illustrated schematically in FIGS. 1 to 10F may be applicable to any treatment portion. And although the embodiment illustrated FIGS. 11A to 11T is described with reference to a leg as the treatment portion, the structures and functions described may be applied to, or adapted to be applied to, other treatment portions of a user's body. Other embodiments that are configured specifically for other treatment portions of a user's body are described below, but any of the illustrated structures and functions may be adapted to user with other treatment portions. These embodiments also illustrate a benefit of the modular construction of the treatment delivery component, e.g., that the thermal delivery component can be releasably coupled to the outer shell, pressure delivery component, and/or liner. With this approach to construction, the outer shell, pressure delivery component, and/or liner can be configured to interoperate with a thermal delivery component that may be sourced from a third party manufacturer, i.e., the manufacturer of the treatment delivery component may source the thermal delivery component separately, and/or may direct a user to secure the thermal delivery component directly from the third party. Relatedly, the control unit can be configured to operate with, or include adapters to enable it to operate with, third party thermal delivery components, e.g., with the thermal connector thereof. A user may thereby also gain increased usability and functionality from a system that includes a control unit that can operate with different outer shells, pressure delivery components, and liners, and with thermal delivery components obtained from the supplier of the other components, or directly from a third party. In some embodiments, the modularity and interoperability can extend to having the control unit control the operation of the pressure delivery component (and used with the outer shell and liner), while a third part control unit can control the operation of the thermal delivery component. This can be economically advantageous for a user who already owns a thermal treatment system, and wishes to add the functionality of the pressure delivery component, for pressure therapy and/or for the benefits of improved adaptation and operation of the thermal delivery component described above.

A treatment delivery component configured for application to an ankle of a user is shown in FIGS. 19A to 19G. Treatment delivery component 14020 is constructed with an integrated outer shell, pressure applicator, and liner, which can receive a thermal delivery component. For ease of illustration, not all elements of these components are specifically identified in the figures. Body portion 14110 defines with pressure applicator 14210 and/or liner (not separately shown) a liner pocket 14520, into which thermal applicator 14310 (shown in dashed lines in FIG. 19B, disposed in liner pocket 14520) can be disposed, and the thermal conduit (not shown) can be disposed through passage 14130. Thermal applicator 14310 can be retained in liner pocket 14520 by closing liner pocket 14520 with thermal applicator couplers 14220 (e.g., hook and loop fasteners).

Figure 19A:
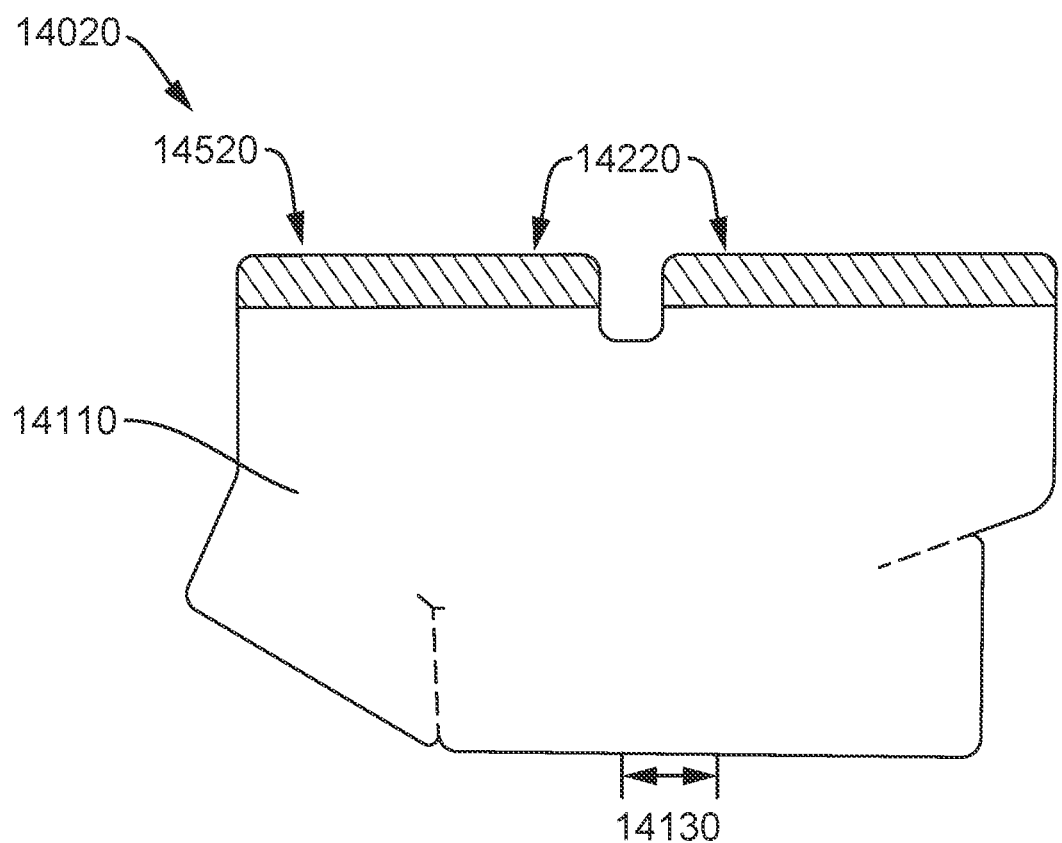
FIGS. 19A to 19G are illustrations of a treatment delivery component configured for use with an ankle of a user, according to an embodiment.
Figure 19B:
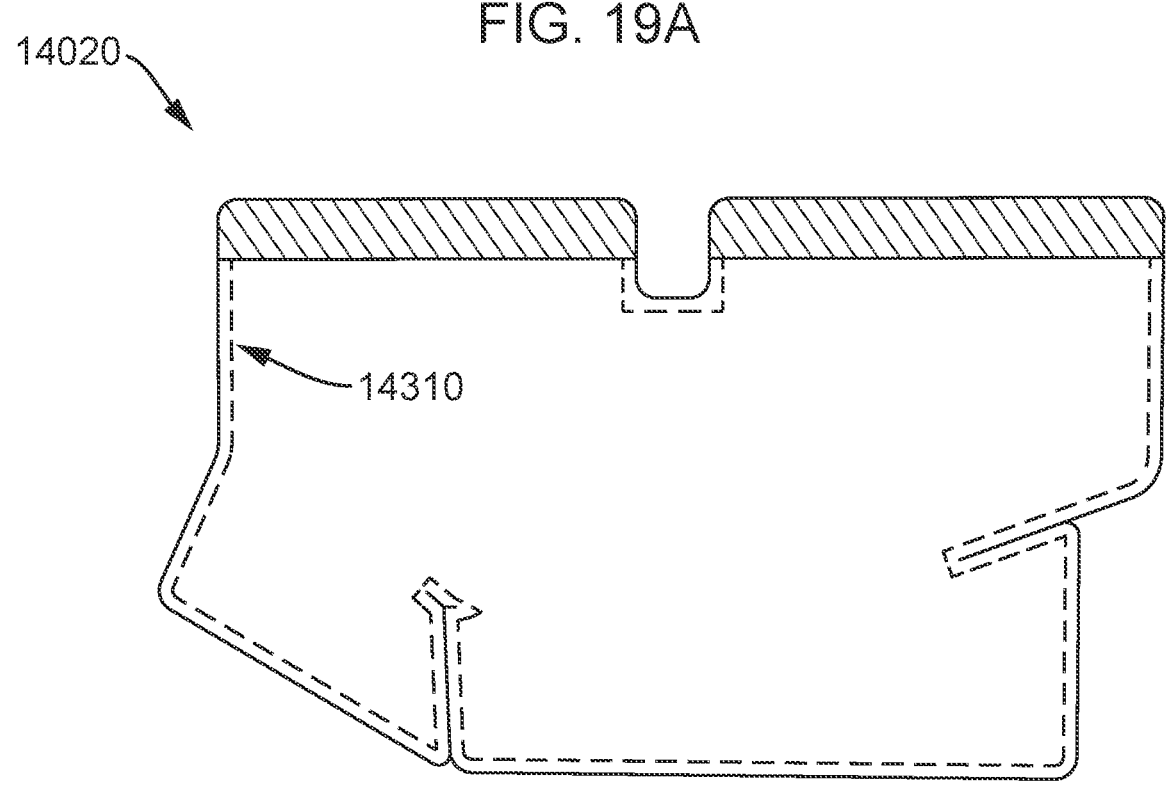
Figure 19C:
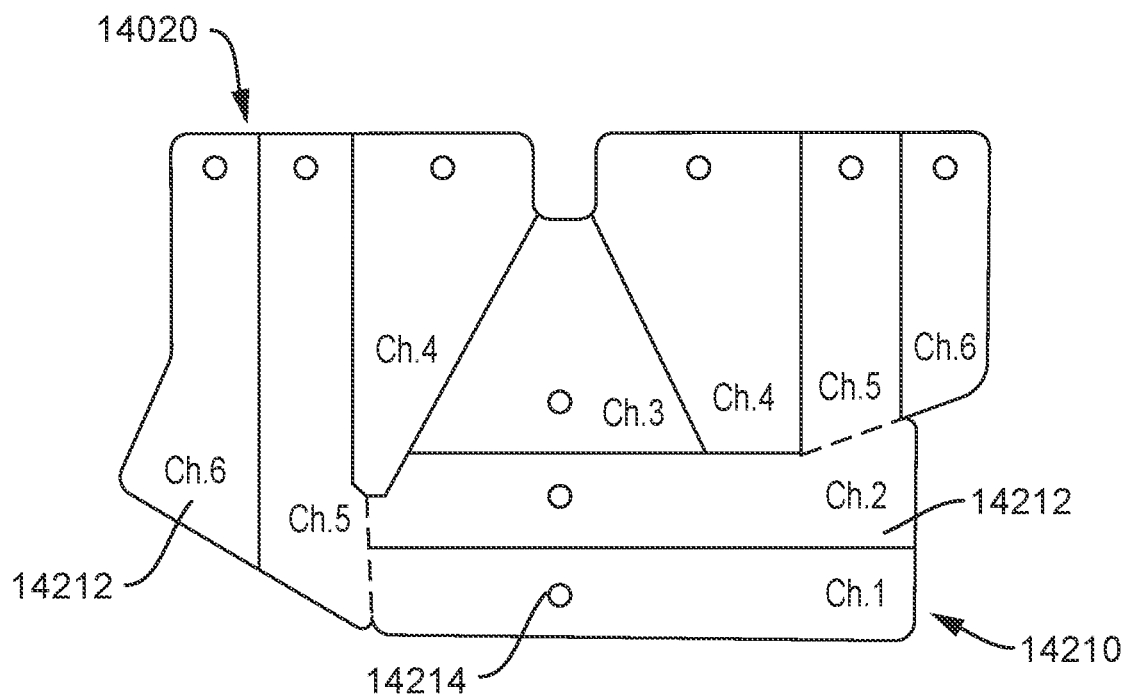
Figure 19D:
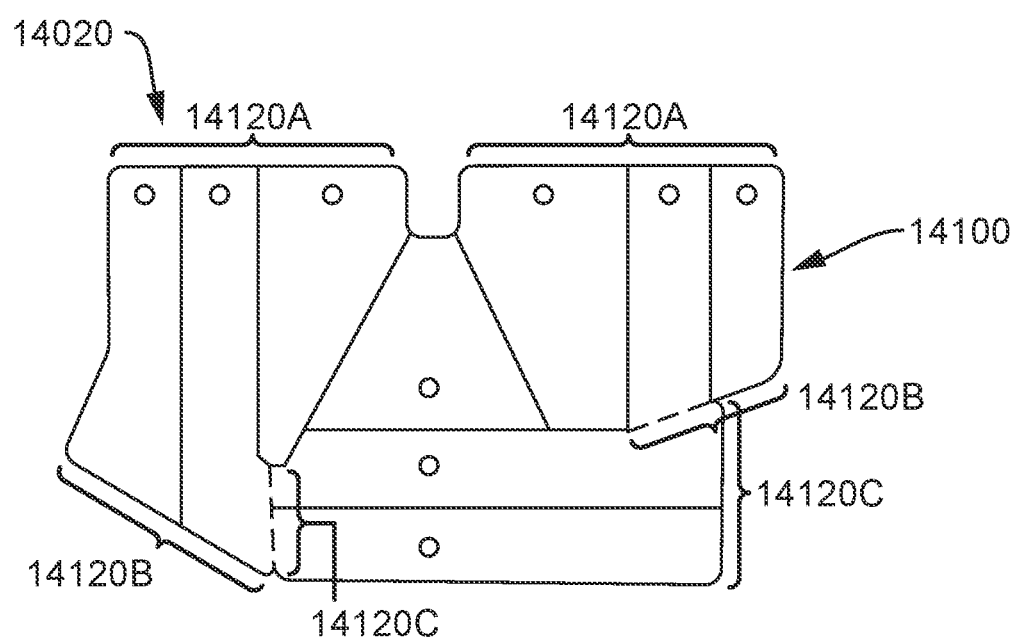
Figure 19E:
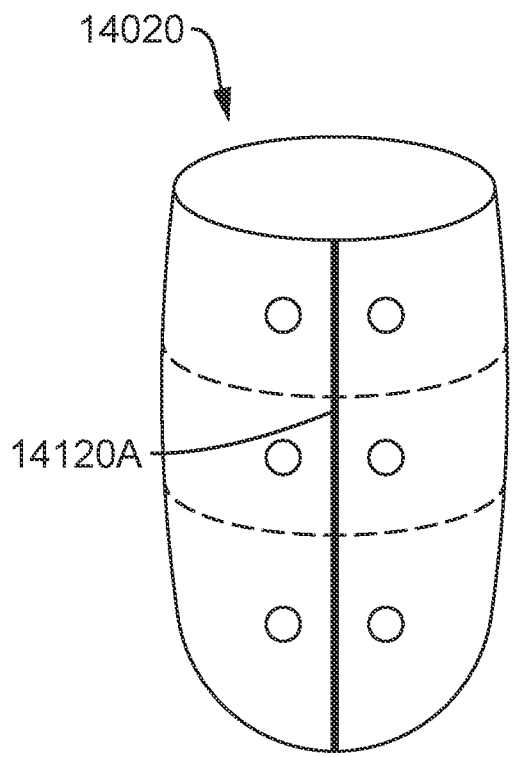
Figure 19F:
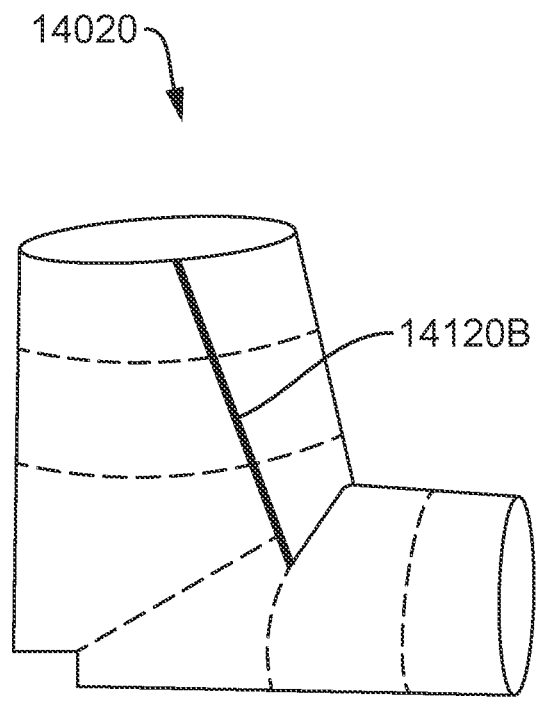
Figure 19G:
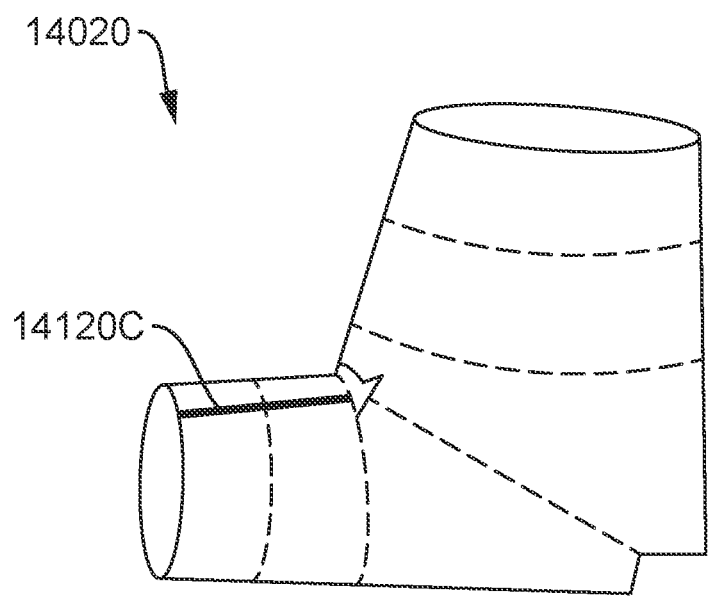

As shown in FIGS. 19C and 19D, pressure applicator 14210 includes six pressure elements 14212 (also labeled as chambers, or Ch. 1 to Ch. 6), each of which includes a pressure port 14214 to each of which a fluid passage of a pressure conduit (not shown) can be coupled, as described above for other embodiments. As with other embodiments, each pressure element 14212 can be actuated (expanded or collapsed) by a control unit independently. As shown in FIG. 19D, outer shell 14100 can include three mating sets of fastener portions 14120A, 14120B, and 14102C. These mating sets of fastener portions can be fastened together to secure treatment delivery component 14020 around the ankle of the user, in the configuration shown in FIGS. 19E-G.

A treatment delivery component configured for application to a shoulder of a user is shown in FIGS. 20A to 20D. Treatment delivery component 15020 is constructed with an integrated outer shell, pressure applicator, and liner, which can receive a thermal delivery component. For ease of illustration, not all elements of these components are specifically identified in the figures. Body portion 15110 defines with pressure applicator 15210 and/or liner (not separately shown) a liner pocket 15520, into which thermal applicator 15310 (shown in dashed lines in FIG. 20A, disposed in liner pocket 15520) can be disposed. Thermal applicator 15310 can be retained in liner pocket 15520 by closing liner pocket 15520 with thermal applicator couplers 15220 (e.g., hook and loop fasteners).

Figure 20A:
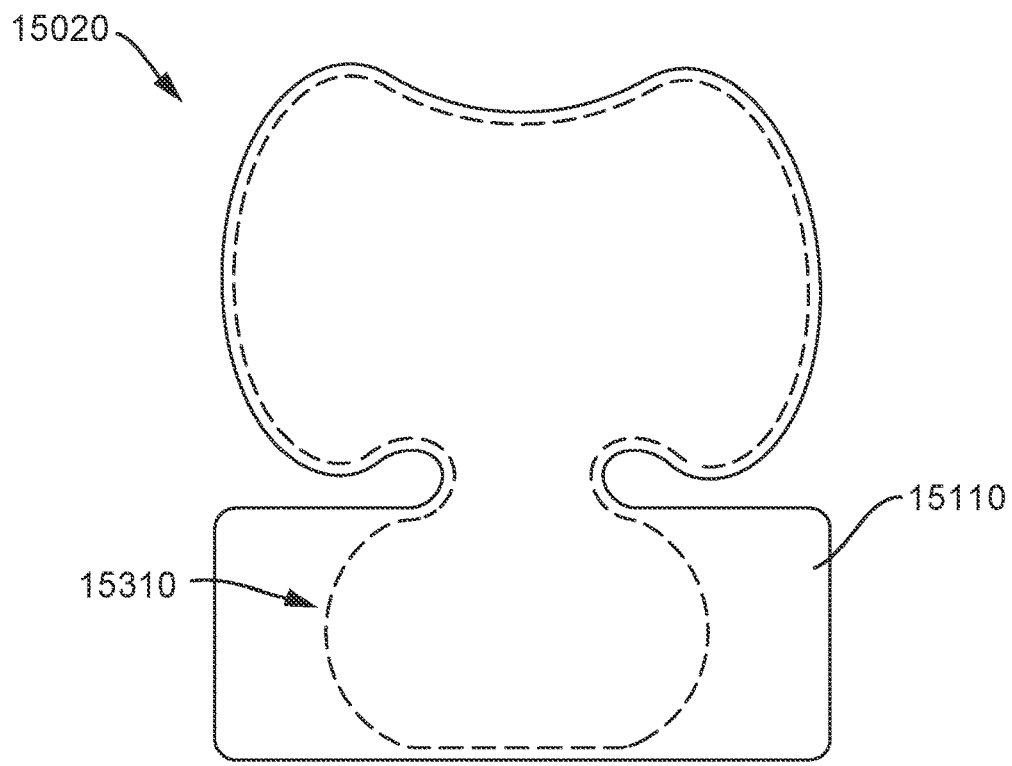
FIGS. 20A to 20D are illustrations of a treatment delivery component configured for use with a shoulder of a user, according to an embodiment.
Figure 20B:
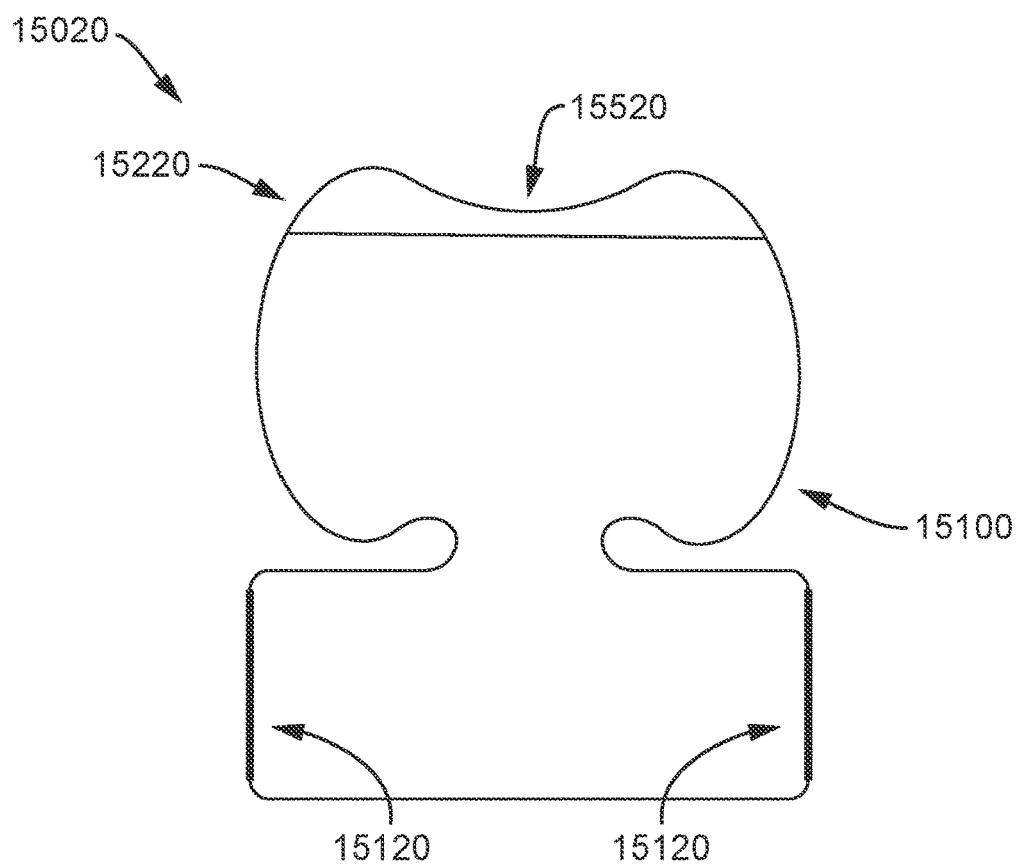
Figure 20C:
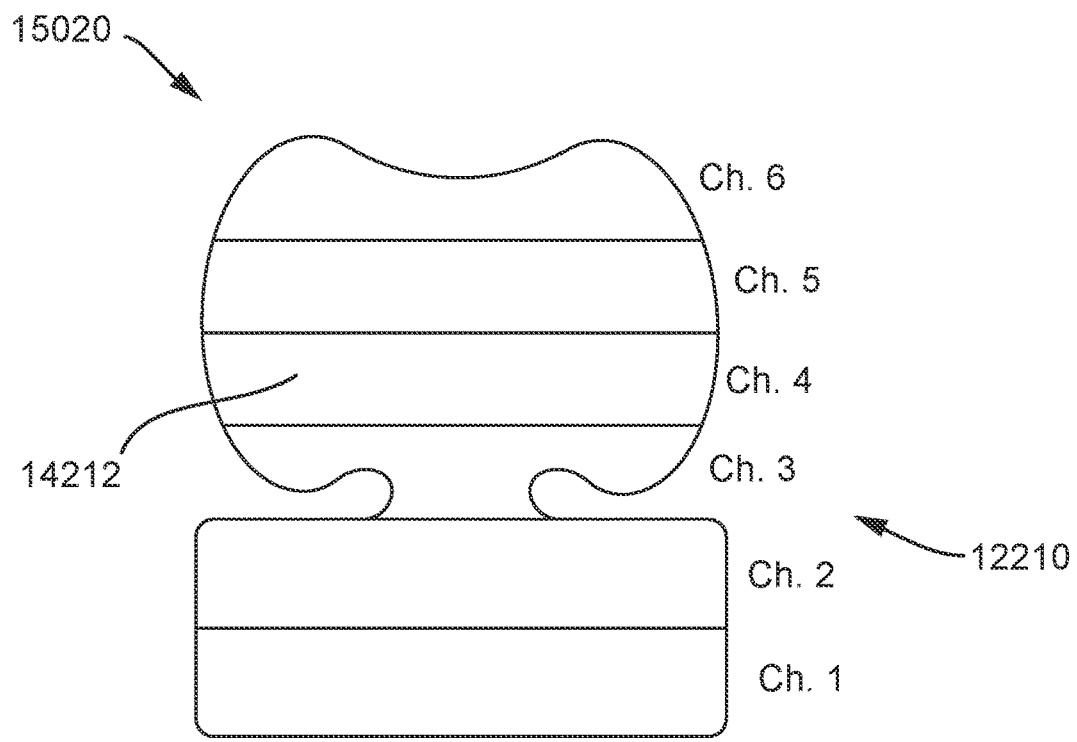
Figure 20D:
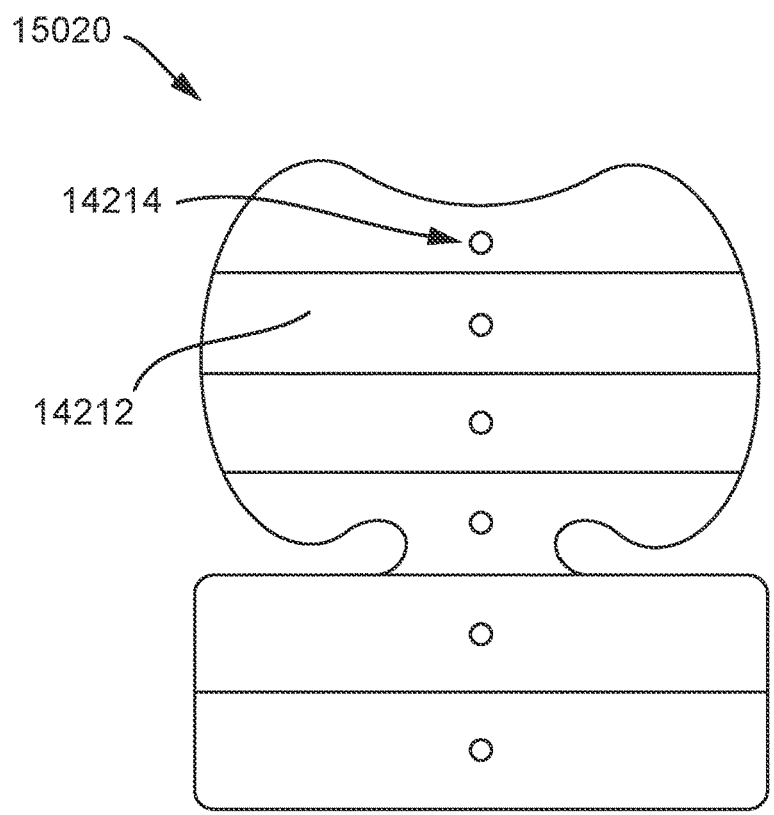

As shown in FIGS. 20C and 20D, pressure applicator 15210 includes six pressure elements 15212 (also labeled as chambers, or Ch. 1 to Ch. 6), each of which includes a pressure port 15214 to each of which a fluid passage of a pressure conduit (not shown) can be coupled, as described above for other embodiments. As with other embodiments, each pressure element 15212 can be actuated (expanded or collapsed) by a control unit independently. As shown in FIG. 20B, outer shell 14100 can include a mating set of fastener portions 15120. This mating set of fastener portions can be fastened together to secure treatment delivery component 15020 around the shoulder of the user.

Figure 21A:
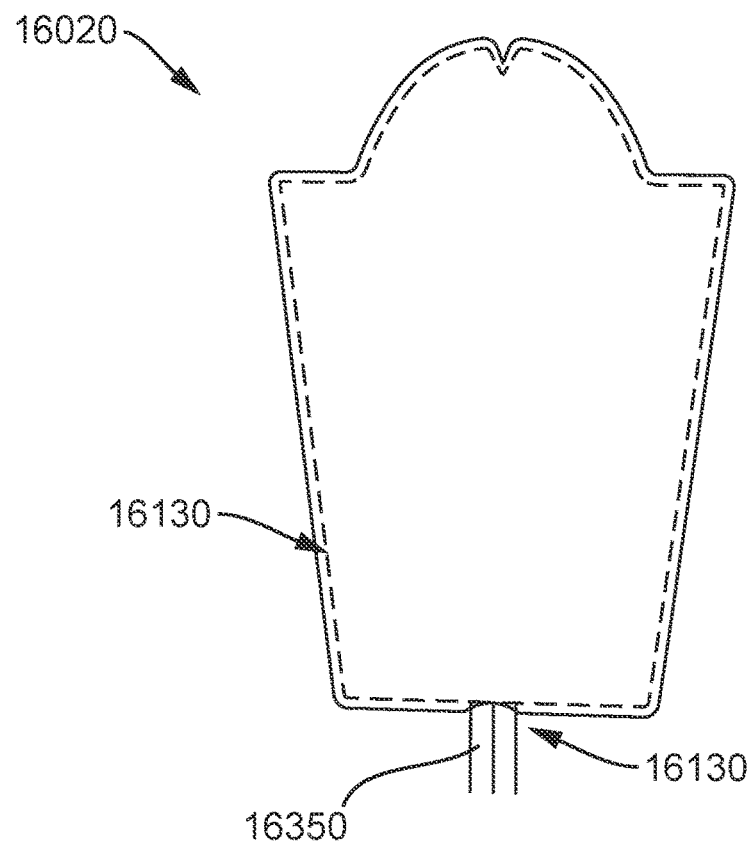
FIGS. 21A to 21C are illustrations of a treatment delivery component configured for use with an arm of a user, according to an embodiment.
Figure 21B:
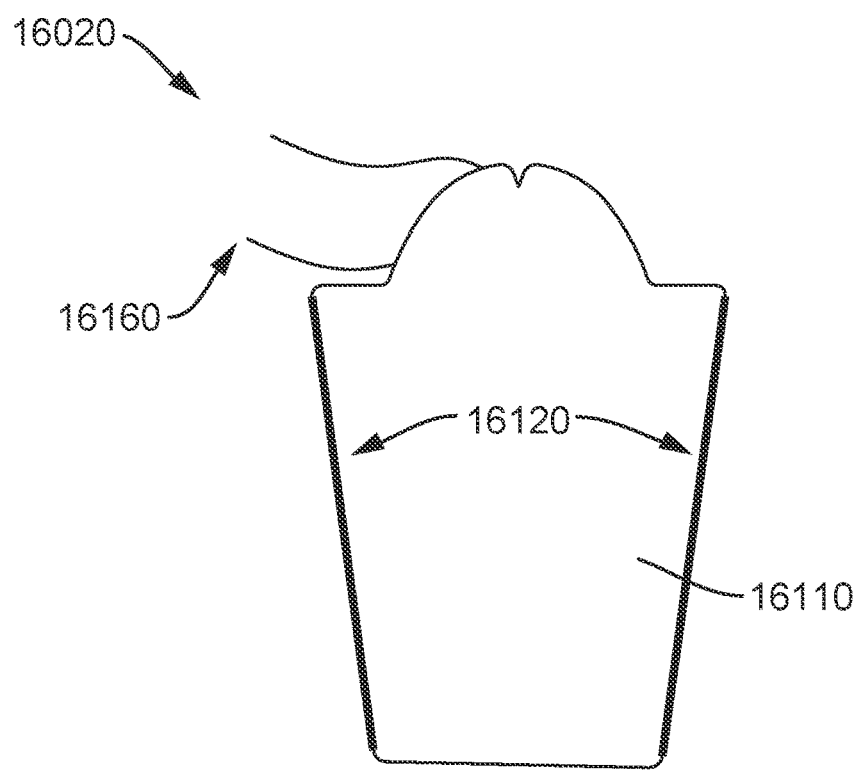
Figure 21C:
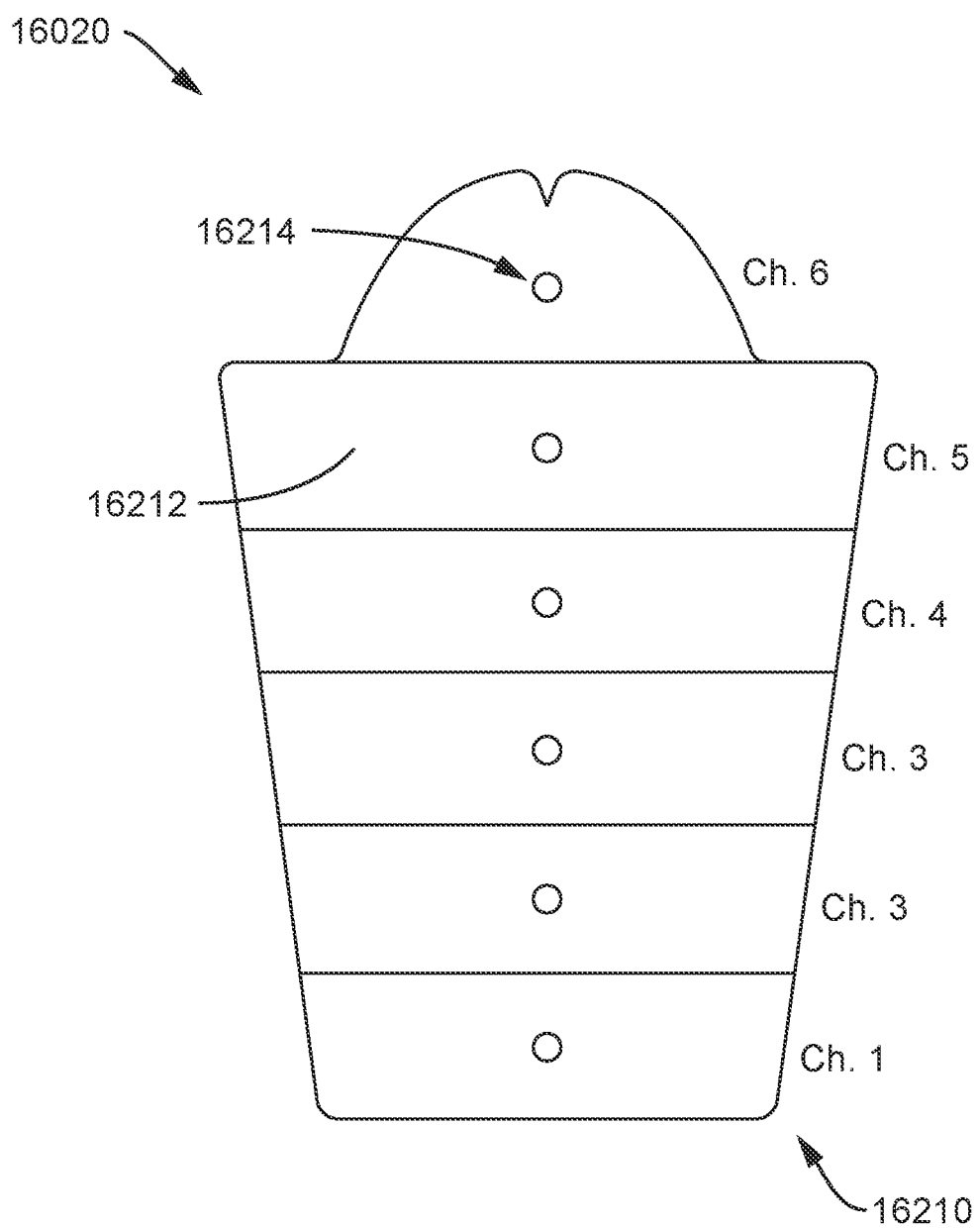

A treatment delivery component configured for application to an arm of a user is shown in FIGS. 21A to 21C. Treatment delivery component 16020 is constructed with an integrated outer shell, pressure applicator, and liner, which can receive a thermal delivery component. For ease of illustration, not all elements of these components are specifically identified in the figures. Body portion 16110 defines with pressure applicator 16210 and/or liner (not separately shown) a liner pocket into which thermal applicator 16310 (shown in dashed lines in FIG. 20A, disposed in liner pocket 15520) can be disposed, and thermal conduit 16350 can be disposed through passage 16130.

As shown in FIG. 21C, pressure applicator 16210 includes six pressure elements 16212 (also labeled as chambers, or Ch. 1 to Ch. 6), each of which includes a pressure port 16214 to each of which a fluid passage of a pressure conduit (not shown) can be coupled, as described above for other embodiments. As with other embodiments, each pressure element 16212 can be actuated (expanded or collapsed) by a control unit independently. As shown in FIG. 21B, outer shell 16100 can include a mating set of fastener portions 16120 (e.g., zippers). This mating set of fastener portions can be fastened together to secure treatment delivery component 16020 around the arm of the user. Treatment delivery component 16020 can further be secured to the user's body with straps 16160, which may be secured around the user's chest.

A treatment delivery component configured for application to a knee of a user is shown in FIGS. 22A to 22D. Treatment delivery component 17020 is constructed with an integrated outer shell, pressure applicator, and liner, which can receive a thermal delivery component. For ease of illustration, not all elements of these components are specifically identified in the figures. Body portion 17110 defines with pressure applicator 17210 and/or liner (not separately shown) a liner pocket into which thermal applicator 17310 (shown in FIG. 22A and dashed lines in FIG. 22B) can be disposed, and thermal conduit 17350 can be disposed through passage 17130.

Figure 22A:
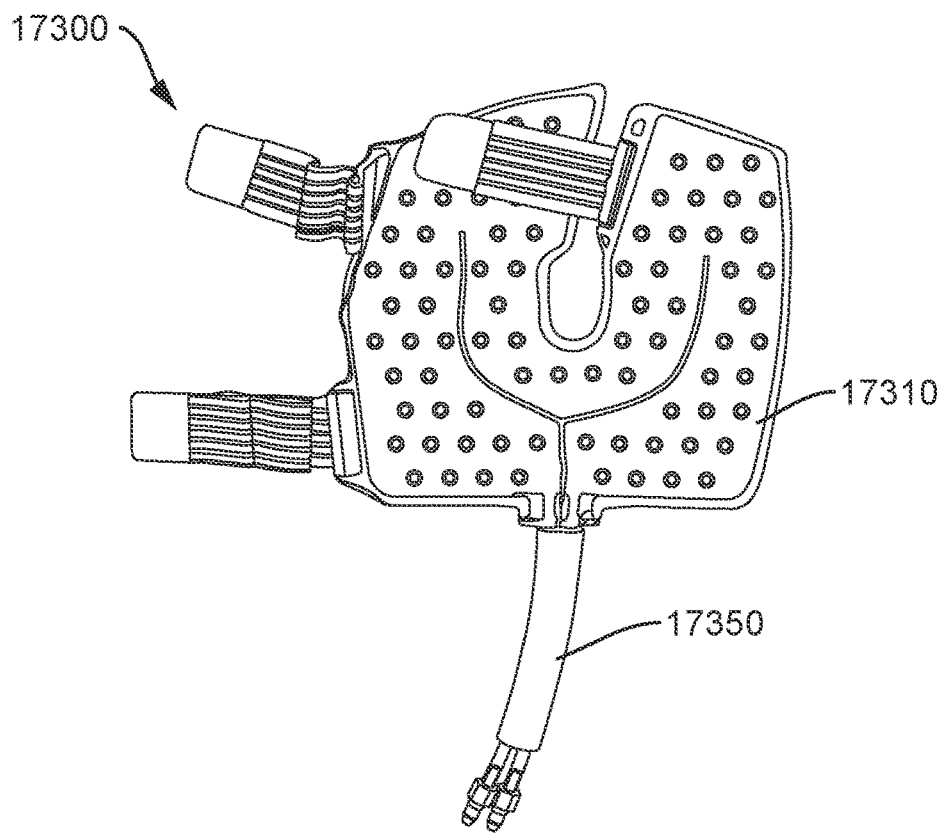
FIGS. 22A to 22D are illustrations of a treatment delivery component configured for use with a knee of a user, according to an embodiment.
Figure 22B:
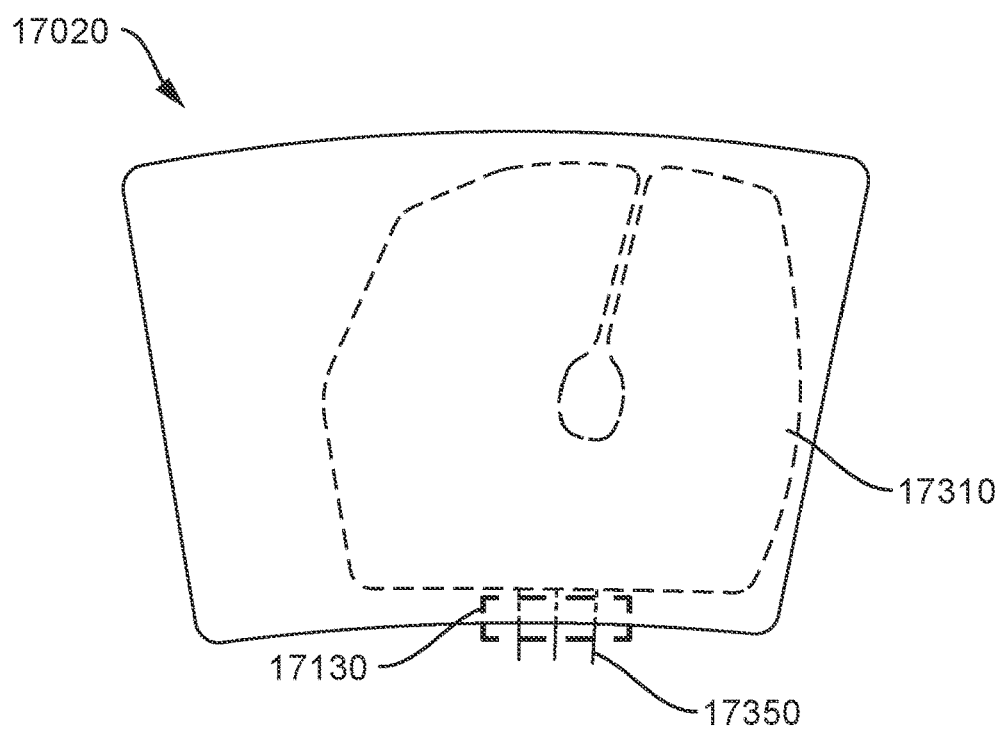
Figure 22C:
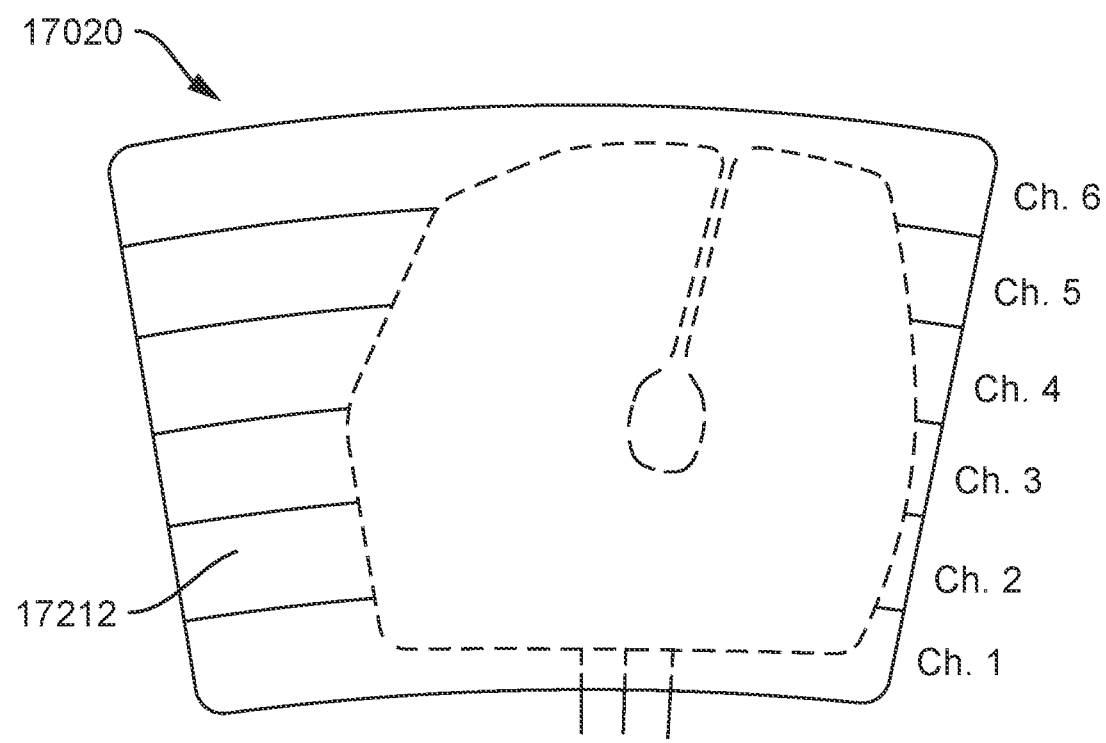
Figure 22D:
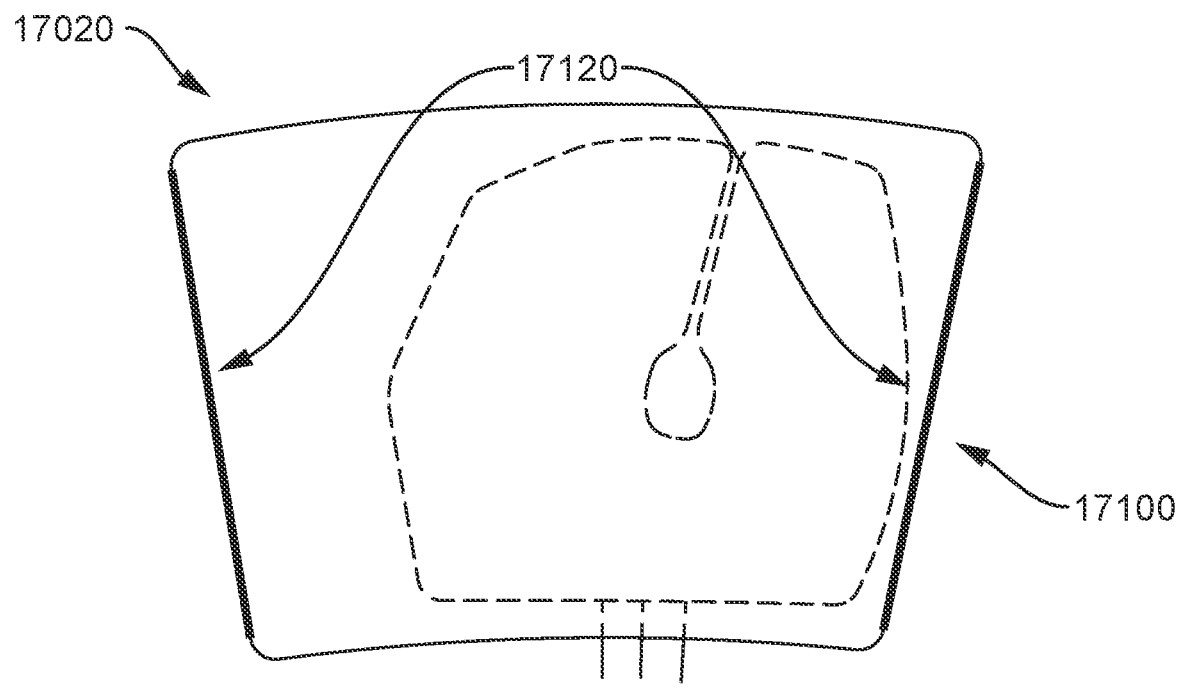

As shown in FIGS. 22C and 22D, pressure applicator 17210 includes six pressure elements 17212 (also labeled as chambers, or Ch. 1 to Ch. 6). As with other embodiments, each pressure element 14212 can be actuated (expanded or collapsed) by a control unit independently. As shown in FIG. 22D, outer shell 14100 can include a mating set of fastener portions 17120, which can be fastened together to secure treatment delivery component 17020 around the knee of the user.

Figure 23A:
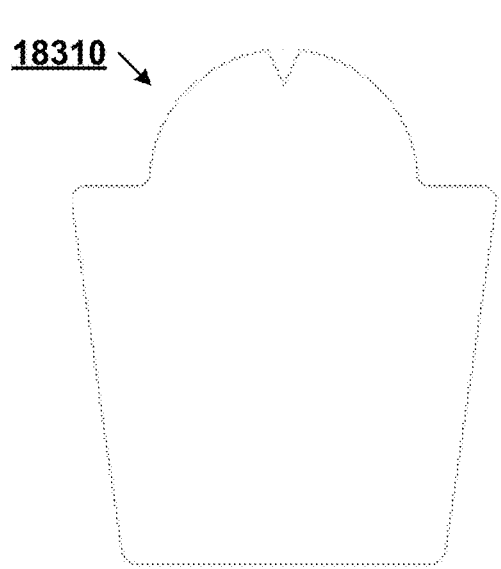
FIGS. 23A to 23D are illustrations of a treatment delivery component configured for use with an arm of a user, according to an embodiment.
Figure 23B:
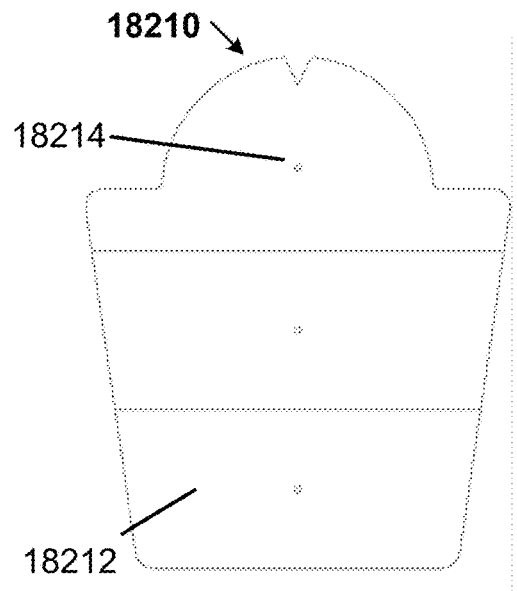
Figure 23C:
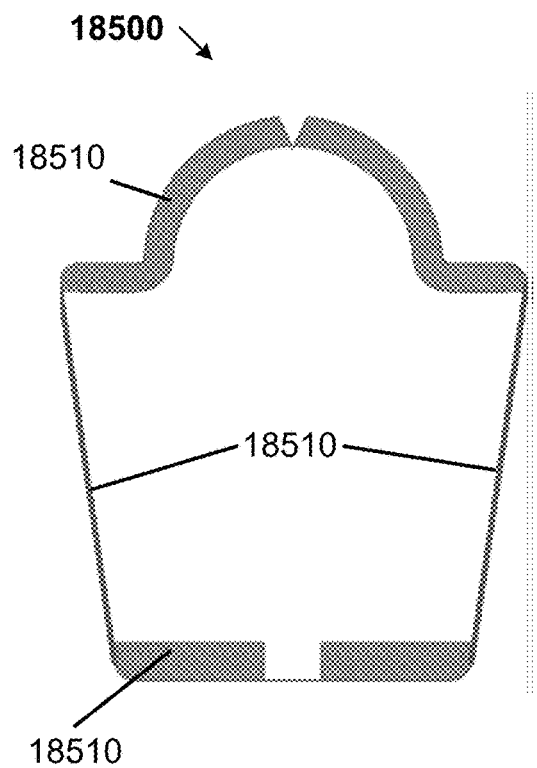
Figure 23D:
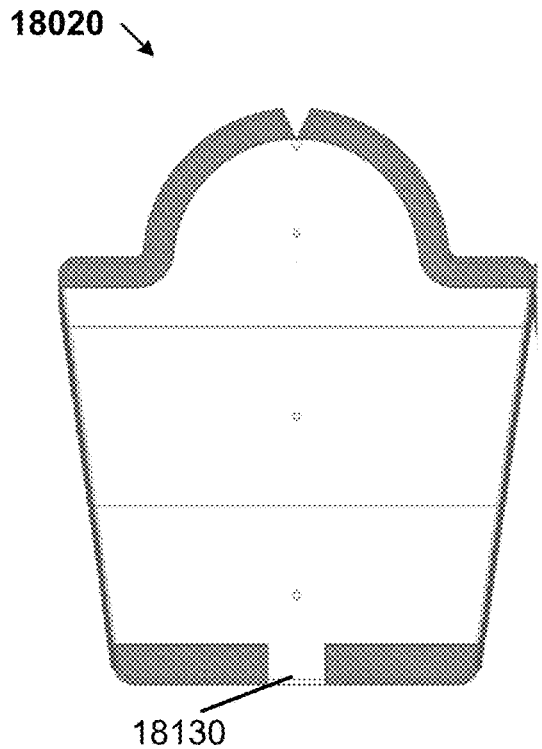

A treatment delivery component configured for application to an arm of a user is shown in FIGS. 23A to 23D. Treatment delivery component 18020 includes a thermal applicator 18310 (FIG. 23A), a pressure applicator 18210 (with three pressure elements 18212 and respective pressure ports 18214, and which also functions as the outer shell for treatment delivery component 18020) (FIG. 23B), and liner 18500 (with liner couplers 18510, e.g., zippers along the lateral edges, and hook and loop fasteners along the top and bottom, by which liner 18500 can be releasable attached to pressure applicator 18210 to form a liner pocket and retain thermal applicator 18310) (FIG. 23C). Treatment delivery component is shown assembled in FIG. 23D, ready to receive a liner. Passage 18130 is also shown in FIG. 23D.

Figure 24A:
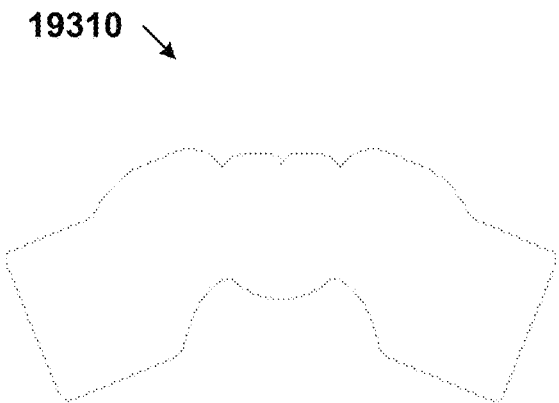
FIGS. 24A to 24D are illustrations of a treatment delivery component configured for use with a torso of a user, according to an embodiment.
Figure 24B:
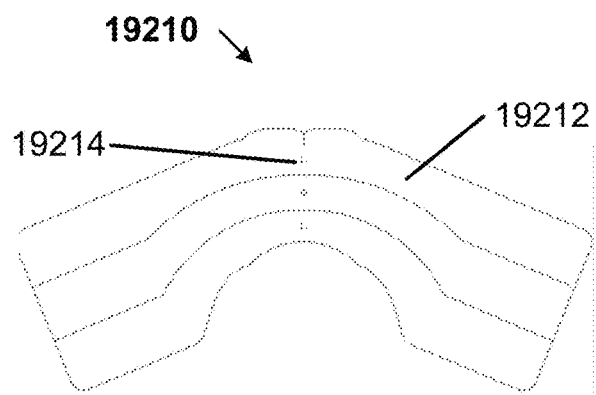
Figure 24C:
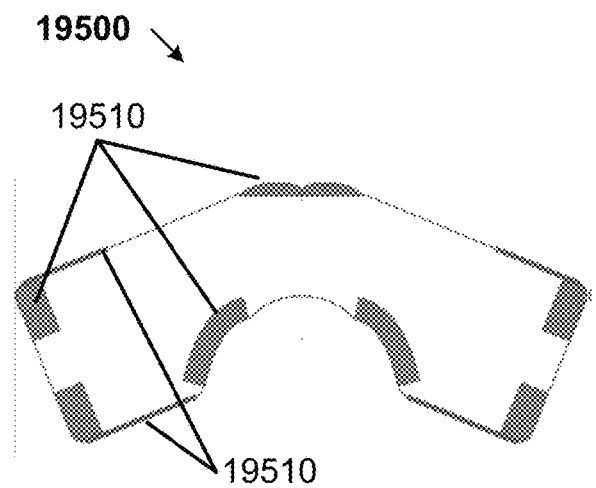
Figure 24D:
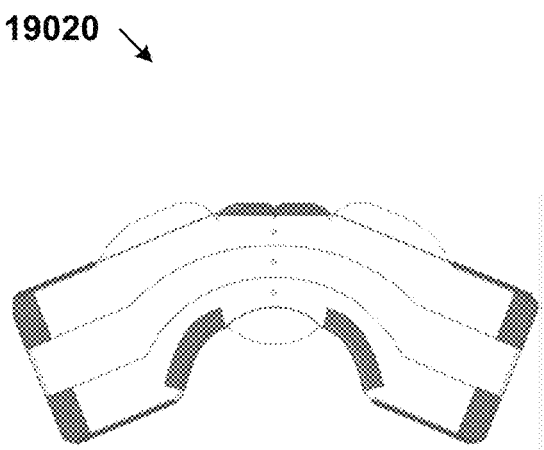

A treatment delivery component configured for application to a torso of a user is shown in FIGS. 24A to 24D. Treatment delivery component 19020 includes a thermal applicator 19310 (FIG. 24A), a pressure applicator 19210 (with three pressure elements 19212 and respective pressure ports 19214, and which also functions as the outer shell for treatment delivery component 19020) (FIG. 24B), and liner 19500 (with liner couplers 18910, e.g., zippers along the lateral edges, and hook and loop fasteners along the top and bottom, by which liner 19500 can be releasable attached to pressure applicator 19210 to form a liner pocket and retain thermal applicator 19310) (FIG. 24C). Treatment delivery component is shown assembled in FIG. 24D.

In other embodiments, a treatment delivery component could be configured for application to the head of a user. Such an embodiment could be a head cap (which could be circular or oval) with a thermal applicator and a pressure applicator, with a circumferential attachment of the thermal applicator pad to part of the head such as the forehead. The thermal applicator could curve upward and overlap the margin of the pressure applicator so that when the pressure applicator is actuated, the thermal applicator is stretched out and tightened against the head.

While various embodiments have been described herein, textually and/or graphically, it should be understood that they have been presented by way of example only, and not limitation. Likewise, it should be understood that the specific terminology used herein is for the purpose of describing particular embodiments and/or features or components thereof and is not intended to be limiting. Various modifications, changes, enhancements, and/or variations in form and/or detail may be made without departing from the scope of the disclosure and/or without altering the function and/or advantages thereof unless expressly stated otherwise. Functionally equivalent embodiments, implementations, and/or methods, in addition to those enumerated herein, will be apparent to those skilled in the art from the foregoing descriptions and are intended to fall within the scope of the disclosure.

For example, while numerous embodiments of treatment systems are described herein as being used with particular devices and/or in particular situations, it should be understood that they have been presented by way of example only and not limitation. The embodiments and/or devices described herein are not intended to be limited to any specific implementation unless expressly stated otherwise. For example, in some implementations, treatment systems 1000, 3000, 4000, 5000, 6000, 7000, 8000, 9000, 10000, 11000, 12000, 13000, 14000, 15000, 16000, 17000, 18000, and 19000, may be used with or without a programmable controller, or used to provide any other treatment not described herein.

Where schematics, embodiments, and/or implementations described above indicate certain components arranged and/or configured in certain orientations or positions, the arrangement of components may be modified, adjusted, optimized, etc. The specific size and/or specific shape of the various components can be different from the embodiments shown and/or can be otherwise modified, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Although various embodiments have been described as having particular characteristics, functions, components, elements, and/or features, other embodiments are possible having any combination and/or sub-combination of the characteristics, functions, components, elements, and/or features from any of the embodiments described herein, except mutually exclusive combinations or when clearly stated otherwise.

Where methods described above indicate certain events occurring in certain order, the ordering of certain events may be modified. Additionally, certain of the events may be performed concurrently in a parallel process when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

What is claimed:

1. Method comprising:
configuring a treatment delivery component of a treatment system for delivery of:
a pressure treatment modality by a pressure delivery component having a pressure applicator and a pressure conduit coupled to the pressure applicator, and
a thermal treatment modality by a thermal delivery component having a thermal applicator and a thermal conduit coupled to the thermal applicator,
to a treatment portion of a user's body, the treatment portion having a circumference or lateral extent,
the treatment delivery component including an outer shell coupled to the pressure applicator, the configuring including releasably coupling the thermal applicator to one or more of the outer shell and the pressure applicator;
the treatment system having a control unit, the control unit having a pressure source and a thermal source,
the pressure applicator including a pressure element that is changeable, in response to receiving pressurized fluid from the pressure source via the pressure conduit, from a collapsed configuration to an expanded configuration having a greater volume than the collapsed configuration,
the thermal applicator having a central portion having a first width and first and second side portions that, together with the central portion, have a second width, the second width being greater than the circumference or lateral extent of the treatment portion;
disposing the treatment delivery component in operative relationship with the treatment portion with the thermal applicator adjacent to a surface of the treatment portion;
coupling the treatment delivery component to the control unit, the coupling including coupling to the pressure source the pressure conduit and coupling to the thermal source the thermal conduit,
pressing the thermal applicator against the treatment portion by delivering to the pressure applicator pressurized fluid to change the pressure element from the collapsed configuration to the expanded configuration within a space between the outer shell and the thermal applicator, the pressing the thermal applicator against the treatment portion including pressing the central portion of the thermal applicator to the treatment portion and urging at least a portion of the inner surfaces of each of the first and second side portions towards and into contact with each other; and
delivering the pressure treatment modality to the treatment portion by the pressure delivery component; and
delivering the thermal treatment modality to the treatment portion by the thermal delivery component.

2. The method of claim 1, wherein the outer shell includes a passage therethrough, the configuring including disposing the thermal conduit through the passage.

3. The method of claim 1, wherein the treatment delivery component further includes a liner releasably coupleable to one or more of the outer shell, the thermal applicator, and the pressure delivery component, the disposing the treatment delivery component including disposing the liner between the thermal applicator and the surface of the treatment portion, the urging at least a portion of the inner surface of each of the first and second side portions including pressing portions of the liner into contact with each other between the first and second side portions of the thermal applicator.

4. The method of claim 3, wherein the liner forms with one or more of the outer shell and the pressure delivery component a liner pocket, the configuring including disposing the thermal applicator in the liner pocket.

5. The method of claim 1, wherein the pressing the thermal applicator against the treatment portion includes delivering the pressurized fluid to the pressure element at a first pressure, and wherein the delivering the pressure treatment modality includes delivering the pressurized fluid to the pressure element at a second pressure higher than the first pressure.

6. The method of claim 1, wherein the outer shell has a body portion shaped to enclose a body part of a user and having elongated, longitudinally oriented, opposed edges, and the pressure applicator includes a plurality of expandable pressure elements, the pressure elements fluidically coupled to a pressure conduit, at least some of the plurality of pressure elements being elongated laterally on the body portion, so that they extend at least partially circumferentially around the body part when the treatment delivery component is disposed on the body part.

7. The method of claim 1, wherein the outer shell has a body portion shaped to enclose a body part of a user and having elongated, longitudinally oriented, opposed edges, and the pressure applicator includes a plurality of expandable pressure elements, the pressure elements fluidically coupled to a pressure conduit, at least some of the plurality of pressure elements are elongated longitudinally on the body portion, so that they extend lengthwise along the body part when the treatment delivery component is disposed on the body part.

8. Apparatus comprising:
a treatment delivery component including:
an outer shell having a body portion shaped to enclose a body part of a user and having elongated, longitudinally oriented, opposed edges, the opposed edges having mating portions of a zipper by which the opposed edges can be secured together to secure the body portion around the body part;
a liner shaped to enclose a substantial portion of the body part, the liner having outer edges that are releasably coupleable to the opposed edges of the body portion proximate to the mating portions of the zipper, the liner having a lower edge coupleable to the body portion near a lower portion thereof, the liner defining in part a liner pocket that is accessible from an upper edge of the liner and into which a treatment component can be introduced into the liner pocket; and a thermal applicator configured to selectively apply thermal treatment to the body part via an inner surface of the thermal applicator with thermal liquid received from a liquid conduit coupled to the thermal applicator, the thermal applicator having a central portion having a first width and a first side portion and a second side portion that, together with the central portion, have a second width, the thermal applicator being couplable to the outer shell near the opposed edges by the first side portion and the second side portion; and a pressure applicator fixedly coupled to the body portion and including a plurality of expandable pressure elements, the pressure elements fluidically coupled to a pressure conduit, the pressure applicator operable to apply pressure to the thermal applicator to enhance apposition of the central portion of the thermal applicator to the treatment portion and, for a treatment portion having a circumference or lateral extent less than the second width of the thermal applicator, to urge at least a portion of the inner surfaces of each of the first side portion and the second side portion towards and into contact with each other with portions of the liner therebetween.

9. The apparatus of claim 8, wherein the liner is removable from the body portion.

10. The apparatus of claim 8, wherein at least some of the plurality of pressure elements are elongated laterally on the body portion, so that they extend at least partially circumferentially around the body part when the treatment delivery component is disposed on the body part.

11. The apparatus of claim 8, wherein at least some of the plurality of pressure elements are elongated longitudinally on the body portion, so that they extend lengthwise along the body part when the treatment delivery component is disposed on the body part.

12. The apparatus of claim 8, wherein the thermal applicator is removably disposable in the liner pocket.

13. The apparatus of claim 8, further comprising an electrical delivery component having an electrical applicator configured to selectively apply electrical treatment to the body part with electrical energy received from an electrical conduit coupled to the electrical applicator.

14. The apparatus of claim 13, wherein the electrical applicator is removably disposable in the liner pocket, the pressure applicator operable to apply pressure to the electrical applicator to enhance apposition of the electrical applicator to the body part.

15. The apparatus of claim 13, wherein the electrical applicator is integrated with the liner.

16. Apparatus comprising:
a treatment delivery component including:
an outer shell having a body portion shaped to enclose a body part of a user and having elongated, longitudinally oriented, opposed edges, the opposed edges having mating portions of a zipper by which the opposed edges can be secured together to secure the body portion around the body part;
a pressure applicator fixedly coupled to the body portion and including a plurality of expandable pressure elements, the pressure elements fluidically coupled to a pressure conduit; and
a thermal applicator configured to selectively apply thermal treatment to the body part via an inner surface of the thermal applicator with thermal liquid received from a liquid conduit coupled to the thermal applicator, the thermal applicator having a central portion having a first width and a first side portion and a second side portion that, together with the central portion, have a second width, the thermal applicator being releasably couplable to the outer shell near the opposed edges by the first side portion and the second side portion,
the pressure applicator operable to apply pressure to the thermal applicator to enhance apposition of the central portion of the thermal applicator to the treatment portion and, for a treatment portion having a circumference or lateral extent less than the second width of the thermal applicator, to urge at least a portion of the inner surfaces of each of the first side portion and the second side portion towards and into contact with each other.

17. The apparatus of claim 16, further comprising:
a liner shaped to enclose a substantial portion of the body part, the liner having outer edges that are releasably coupleable to the opposed edges of the body portion proximate to the mating portions of the zipper, the liner having portions disposable between the inner surfaces of the first side portion and the second side portion and to be pressed into contact with each other therebetween.

18. The apparatus of claim 17, wherein the liner is removable from the body portion.

19. The apparatus of claim 17, wherein the liner has a lower edge coupleable to the body portion near a lower portion thereof, the liner defining in part a liner pocket that is accessible from an upper edge of the liner and into which the thermal applicator can be introduced into the liner pocket.

20. The apparatus of claim 16, further comprising:
an electrical applicator configured to selectively apply electrical treatment to the body part via an inner surface of the electrical applicator with electrical energy received from an electrical conduit coupled to the electrical applicator, the electrical applicator having a central portion having a first width and a first side portion and a second side portion that, together with the central portion, have a second width, the electrical applicator being releasably couplable to the outer shell near the opposed edges by the first side portion and the second side portion,
the pressure applicator operable to apply pressure to the electrical applicator to enhance apposition of the central portion of the electrical applicator to the treatment portion and, for a treatment portion having a circumference or lateral extent less than the second width of the electrical applicator, to urge at least a portion of the inner surfaces of each of the first side portion and the second side portion towards each other.

21. The apparatus of claim 16, wherein at least some of the plurality of pressure elements are elongated laterally on the body portion, so that they extend at least partially circumferentially around the body part when the treatment delivery component is disposed on the body part.

22. The apparatus of claim 16, wherein at least some of the plurality of pressure elements are elongated longitudinally on the body portion, so that they extend lengthwise along the body part when the treatment delivery component is disposed on the body part.

23. The apparatus of claim 16, an electrical delivery component having an electrical applicator configured to selectively apply electrical treatment to the body part with electrical energy received from an electrical conduit coupled to the electrical applicator.

* * * * *